US010722578B2

(12) United States Patent
Mosse et al.

(10) Patent No.: US 10,722,578 B2
(45) Date of Patent: *Jul. 28, 2020

(54) METHODS AND COMPOSITIONS FOR TREATING NEUROBLASTOMA

(71) Applicant: The Children's Hospital of Philadelphia, Philadelphia, PA (US)

(72) Inventors: Yael P. Mosse, Wynewood, PA (US); Erica L. Carpenter, Wyndmoor, PA (US)

(73) Assignee: THE CHILDREN'S HOSPITAL OF PHILADELPHIA, Philadelphia, PA (US)

(*) Notice: Subject to any disclaimer, the term of this patent is extended or adjusted under 35 U.S.C. 154(b) by 11 days.

This patent is subject to a terminal disclaimer.

(21) Appl. No.: 14/607,573

(22) Filed: Jan. 28, 2015

(65) Prior Publication Data

US 2015/0132317 A1 May 14, 2015

Related U.S. Application Data

(63) Continuation of application No. 13/072,090, filed on Mar. 25, 2011, now abandoned, which is a continuation-in-part of application No. 12/853,834, filed on Aug. 10, 2010, now abandoned, which is a continuation-in-part of application No. PCT/US2009/034288, filed on Feb. 17, 2009.

(60) Provisional application No. 61/123,775, filed on Apr. 11, 2008, provisional application No. 61/029,212, filed on Feb. 15, 2008.

(51) Int. Cl.
| | |
|---|---|
| *A61K 39/00* | (2006.01) |
| *A61K 31/00* | (2006.01) |
| *A61K 39/395* | (2006.01) |
| *C12Q 1/6886* | (2018.01) |
| *A61K 31/4545* | (2006.01) |
| *C07K 16/40* | (2006.01) |

(52) U.S. Cl.
CPC ...... *A61K 39/3955* (2013.01); *A61K 31/4545* (2013.01); *C07K 16/40* (2013.01); *C12Q 1/6886* (2013.01); *A61K 2039/505* (2013.01); *C07K 2317/73* (2013.01); *C07K 2317/732* (2013.01); *C12Q 2600/106* (2013.01); *C12Q 2600/136* (2013.01); *C12Q 2600/172* (2013.01)

(58) Field of Classification Search
None
See application file for complete search history.

(56) References Cited

U.S. PATENT DOCUMENTS

2007/0032515 A1 2/2007 Anand et al.
2007/0254295 A1 11/2007 Harvey et al.
2008/0118512 A1* 5/2008 Auf Der Maur .. C07K 16/2896
424/139.1
2008/0300273 A1 12/2008 Christensen et al.
2011/0256546 A1* 10/2011 Morris ................... C07K 14/71
435/6.14

FOREIGN PATENT DOCUMENTS

WO 2007066187 6/2007

OTHER PUBLICATIONS

George et al, Nature 455:975-8, Oct. 16, 2008.*
Janoueic-Ierosey et al, Nature, 455:968-971, 2008.*
Loren, C.E., et al., A crucial role for the Anaplastic lymphoma kinase receptor tyrosine kinase in gut development in *Drosophila melanogaster*, EMBO Rep., 2003, 781-6, 4(8).
Mosse, Y.P., et al., Identification of ALK as a major familial neuroblastoma predisposition gene, Nature, 2008, 930-5, 455(7215).
Mosse, Y.P., et al., Inhibition of ALK signaling for cancer therapy, Clin Cancer Res., 2009, 5609-14, 15(18).
Moog-Lutz, C., et al., Activation and Inhibition of Anaplastic Lymphoma Kinase Receptor Tyrosine Kinase by Monoclonal Antibodies and Absence of Agonist Activity of Pleiotrophin, J Biol Chem., 2005, 26039-26048, 280(28).
Mujoo et al., Disialoganglioside GD2 on human neuroblastoma cells: target antigen for monoclonal antibody-mediated cytolysis and suppression of tumor growth, Cancer Research, 1987,1098-104, 47(4).
Heuckmann et al., ALK mutations conferring differential resistance to structurally diverse ALK inhibitors, Cancer Therapy: Preclinical, 2011, 7394-401, 17(23).
George, R.E., et al., "Activating Mutations in ALK Provide a Therapeutic Target in Neuroblastoma" Nature (2008) 455:975-978.
Chen, Y., et al., "Oncogenic Mutations of ALK Kinase in Neuroblastoma" Nature (2008) 455:971-974.
Caren, H., et al., "High Incidence of DNA Mutations and Gene Amplifications of the ALK Gene in Advanced Sporadic Neuroblastoma Tumours" Biochem. J. (2008) 416:153-159.
Miyake, I., et al., "Activation of anaplastic lyphoma kinase is responsible for hyperphosphorylation of ShcC in neuroblastoma cell lines" Oncogene (2002) 21:5823-5834.
Schonherr, C., et al. "Activating ALK mutations found in neuroblastoma are inhibited by Crizotinib and NVP-TAE684" Biochem. J. (2011) 440:405-413.
Stoica, G.E., et al., "Midkine Binds to Anaplastic Lymphoma Kinase (ALK) and Acts as a Growth Factor for Different Cell Types" J. Biol. Chem. (2002) 277(39):35990-35998.

* cited by examiner

*Primary Examiner* — Lei Yao

(74) *Attorney, Agent, or Firm* — Robert C. Netter, Jr.; Dann, Dorfman, Herrell & Skillman

(57) ABSTRACT

Methods and compositions for treating neuroblastoma are disclosed.

9 Claims, 40 Drawing Sheets

Specification includes a Sequence Listing.

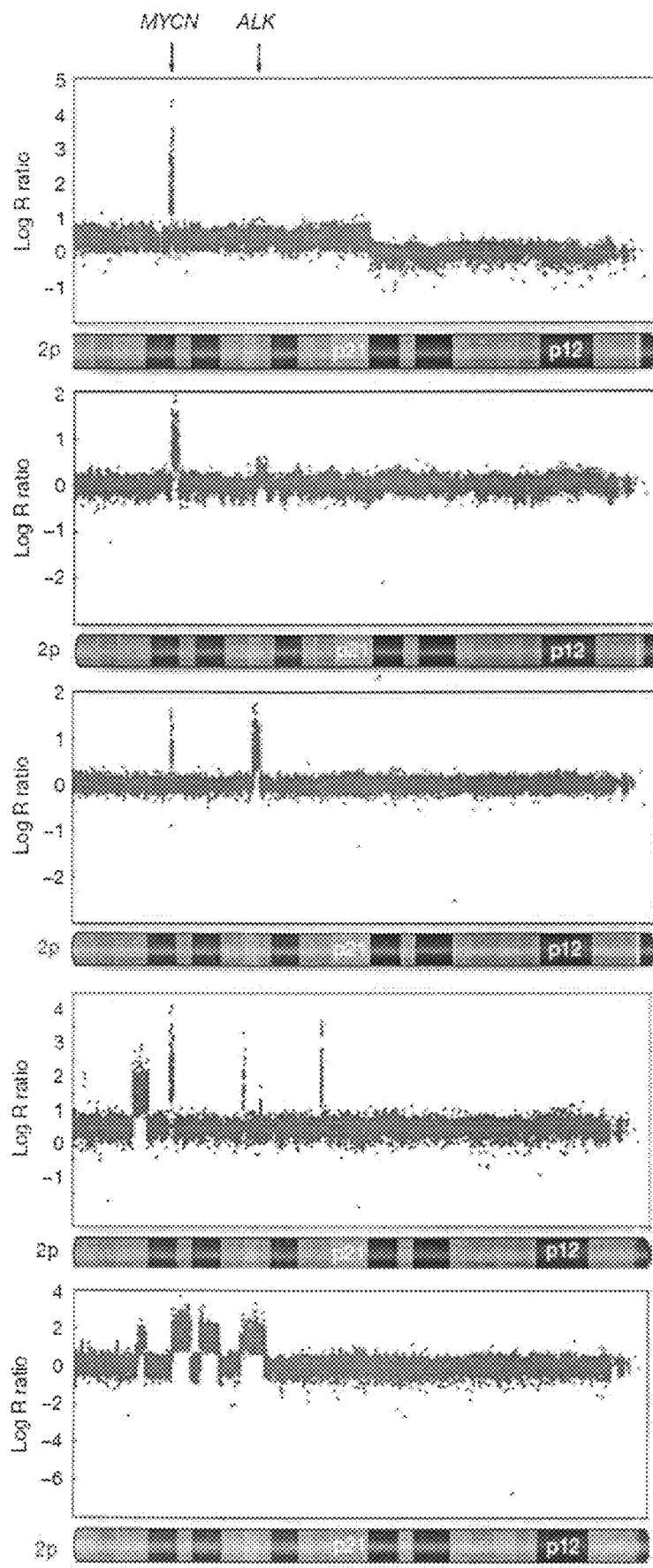

```
MGAIGLLWLLPLLLSTAAVGSGMGTGQRAGSPAAGPPLQPREPLSYSRLQ    50
RKSLAVDFVVPSLFRVYARDLLLPPSSSELKAGRPEARGSLALDCAPLLR   100
LLGPAPGVSWTAGSPAPAEARTLSRVLKGGSVRKLRRAKQLVLELGEEAI   150
LEGCVGPPGEAAVGLLQFNLSELFSWWIRQGEGRLRIRLMPEKKASEVGR   200
EGRLSAAIRASQPRLLFQIFGTGHSSLESPTNMPSPSPDYFTWNLTWIMK   250
DSFPFLSHRSRYGLECSFDFPCELEYSPPLHDLRNQSWSWRRIPSEEASQ   300
MDLLDGPGAERSKEMPRGSFLLLNTSADSKHTILSPWMRSSSEHCTLAVS   350
VHRHLQPSGRYIAQLLPHNEAAREILLMPTPGKHGWTVLQGRIGRPDNPF   400
RVALEYISSGNRSLSAVDFFALKNCSEGTSPGSKMALQSSFTCWNGTVLQ   450
LGQACDFHQDCAQGEDESQMCRKLPVGFYCNFEDGFCGWTQGTLSPHTPQ   500
WQVRTLKDARFQDHQDHALLLSTTDVPASESATVTSATFPAPIKSSPCEL   550
RMSWLIRGVLRGNVSLVLVENKTGKEQGRMVWHVAAYEGLSLWQWMVLPL   600
LDVSDRFWLQMVAWWGQGSRAIVAFDNISISLDCYLTISGEDKILQNTAP   650
KSRNLFERNPNKELKPGENSPRQTPIFDPTVHWLFTTCGASGPHGPTQAQ   700
CNNAYQNSNLSVEVGSEGPLKGIQIWKVPATDTYSISGYGAAGGKGGKNT   750
MMRSHGVSVLGIFNLEKDDMLYILVGQQGEDACPSTNQLIQKVCIGENNV   800
IEEEIRVNRSVHEWAGGGGGGGGATYVFKMKDGVPVPLIIAAGGGGRAYG   850
AKTDTFHPERLENNSSVLGLNGNSGAAGGGGGWNDNTSLLWAGKSLQEGA   900
TGGHSCPQAMKKWGWETRGGFGGGGGGCSSGGGGGGYIGGNAASNNDPEM   950
DGEDGVSFISPLGILYTPALKVMEGHGEVNIKHYLNCSHCEVDECHMDPE  1000
SHKVICFCDHGTVLAEDGVSCIVSPTPEPHLPLSLILSVVTSALVAALVL  1050
AFSGIMIVYRRKHQELQAMQMELQSPEYKLSKLRTSTIMTDYNPNYCFAG  1100
KTSSISDLKEVPRKNITLIRGLGHGAFGEVYEGQVSGMPNDPSPLQVAVK  1150
TLPEVCSEQDELDFLMEALIISKFNHQNIVRCIGVSLQSLPRFILLELMA  1200
GGDLKSFLRETRPRPSQPSSLAMLDLLHVARDIACGCQYLEENHFIHRDI  1250
AARNCLLTCPGPGRVAKIGDFGMARDIYRASYYRKGGCAMLPVKWMPPEA  1300
FMEGIFTSKTDTWSFGVLLWEIFSLGYMPYPSKSNQEVLEFVTSGGRMDP  1350
PKNCPGPVYRIMTQCWQHPEDRPNFAIILERIEYCTQDPDVINTALPIE   1400
YGPLVEEEEKVPVRPKDPEGVPPLLVSQQAKREEERSPAAPPPLPTTSSG  1450
KAAKKPTAAEISVRVPRGPAVEGGHVNMAFSQSNPPSELHKVHGSRNKPT  1500
SLWNPTYGSWFTEKPTKKNNPIAKKEPHDRGNLGLEGSCTVPPNVATGRL  1550
PGASLLLEPSSLTANMKEVPLFRLRHFPCGNVNYGYQQQGLPLEAATAPG  1600
AGHYEDTILKSNSMNQPGP                                 1620
```

Figure 9A

```
atg ggagccatcg ggctcctgtg gctcctgccg ctgctgcttt ccacggcagc tgtgggctcc gggatgggga ccggccagcg
cgcgggctcc ccagctgcgg ggccgccgct gcagcccgg gagccactca gctactcgcg cctgcagagg aagagtctgg
cagttgactt cgtggtgccc tcgctcttcc gtgtctacgc ccgggaccta ctgctgccac catcctcctc ggagctgaag
gctggcaggc ccgaggcccg cggctcgcta gtctggact gcgcccgct gctcaggttg ctggggccgg cgccggggt
ctcctggacc gccggttcac cagccccggc agaggcccgg acgctgtcca gggtgctgaa gggcggctcc gtgcgcaagc
tccggcgtgc caagcagttg gtgctggagc tgggcgagga ggcgatcttg ggcggtttgcg tcgggccccc cggggaggcg
gctgtggggc tgctccagtt caatctcagc gagctgttca gttggtggat tcgccaaggc gaagggcgac tgaggatccg
cctgatgccc gagaagaagg cgtcggaagt gggcagagag ggaaggctgt ccgcggcaat tcgcgcctcc cagcccgcc
ttctcttcca gatcttcggg actggtcata gctccttgga atcaccaaca acatgcctt ctccttctcc tgattatttt
acatggaatc tcacctggat aatgaaagac tccttccctt tcctgtctca tcgcagccga tatggtctgg agtgcagctt
tgacttcccc tgtgagctgg agtattcccc tccactgcat gacctcagga accagagctg gtcctggcgc cgcatccct
ccgaggaggc ctcccagatg gacttgctgg atgggcctgg ggcagagcgt tctaaggaga tgcccagagg ctcctttctc
ctttctcaaca cctcagctga ctccaagcac accatcctga gtccgtggat gaggagcagc agtgagcact gcacactggc
cgtctcggtg cacaggcacc tgcagcctc tggaaggtac attgcccagc tgctgcccca caacgaggct gcaagagaga
tcctcctgat gcccactcca gggaagcatg gttggacagt gctccaggga agaatcgggc gtccagacaa cccatttcga
gtggccctgg aatacatctc cagtggaaac cgcagcttgt ctgcagtgga cttctttgcc ctgaagaact gcagtgaagg
aacatcccca ggctccaaga tggccctgca gagctcctc acttgttgga atgggacagt cctccagctt gggcaggcct
gtgacttcca ccaggactgt gcccagggag aagatgagag ccagatgtgc cggaaactgc ctgtgggttt ttactgcaac
tttgaagatg gcttctgtgg ctggacccaa ggcacactgt caccccacac tcctcaatgg caggtcagga ccctaaagga
tgcccggttc caggaccacc aagaccatgc tctattgctc agtaccactg atgtcccgc ttctgaaagt gctacagtga
ccagtgctac gtttcctga ccgatcaaga gctctccatg tgagctcga atgtcctggc tcattcgtg agtcttgagg
ggaaacgtgt cttggtgct agtggagaac aaaacggga aggagcaagg caggatggtc tggcatgtcg ccgcctatga
aggcttgagc ctgtggcagt ggatggtgtt gcctctcctc gatgtgtctg acaggttctg gctgcagatg gtcgcatggt
gggacaagg atccagagcc atcgtggctt ttgacaatat ctccatcagc ctggactgct acctcaccat tagcggagag
gacaagatcc tgcagaatac agcacccaaa tcaagaaacc tgtttgagag aaacccaaac aaggagctga aaccgggga
aaattcacca agacagaccc ccatctttga ccctacagtt cattggctgt tcaccacatg tggggccagc gggccccatg
gccccaccca ggcacagtgc aacaacgcct accagaactc caacctgagc gtggaggtgg ggagcgaggg cccctgaaa
ggcatccaga tctggaaggt gccagccaac ggatccggg ctacggagct gctggcggga aaggcgggaa
gaacaccatg atgcggtgcc acggcgtgtc tgtgctggc atcttcaacc tggagaagga tgacatgctg tacatcctgg
ttgggcagca gggagaggac gcctgcccca gtacaaacca gttaatccag aaagtctgca ttggagagaa caatgtgata
gaagaagaaa tccgtgtgaa cagaagcgtg catgagtggg caggaggcgg aggaggaggg ggtggagcca cctacgtatt
taagatgaag gatggagtgc cggtgcccct gatcattgca gccggaggtg gtggcagggc ctacggggcc aagacagaca
cgttccaccc agagagactg gagaataact cctcggttct agggctaaac ggcaattccg gagccgcagg tggtggaggt
ggctggaatg ataacacttc cttgctctgg gccggaaaat cttttgcagga gggtgccacc ggaggacatt cctgccccca
ggccatgaag aagtgggggt ggagagcaag aggggtttc ggagggggtg cctcctcaggt ggaggaggcg
gaggatatat aggcggcaat gcagcctcaa acaatgaccc cgaaatggat ggggaagatg gggtttcctt catcagtcca
ctgggcatcc tgtacacccc agctttaaaa gtgatgaag gccacgggga agtgaatatt aagcattatc taaactgcag
tcactgtgag gtagacgaat gtcacatgga ccctgaaagc cacaaggtca tctgcttctg tgaccacggg acggtgctgg
ctgaggatgg cgtctcctgc attgtgtcac ccaccccgga gccacacctg ccactctcgc tgatcctctc tgtggtgacc
tctgccctcg tggccgccct ggtcctggct ttctccggca tcatgattgt gtaccgcgg aagaccagg agctgcaagc
catgcagatg gagctgcaga gccctgagta caagctgagc aagctccgca cctcgaccat catgaccgac tacaacccca
actactgctt tgctggcaag acctcctcca tcagtgacct gaaggagggtg ccgcggaaaa acatcacct cattcgggt
ctgggccatg gcgcctttg ggaggtgtat gaaggccagg tgtccggaat gccaacgac ccaagccccc tgcaagtggc
tgtgaagacg ctgcctgaag tgtgctctga acaggacgaa ctggatttcc tcatggaagc cctgatcatc agcaaattca
accaccagaa cattgttcgc tgcattgggg tgagcctgca atccctgccc cggttcatcc tgctggagct catgcgggg
ggagcctca gtccttcct ccgagagacc cgccctcgcc cgagccagcc ctcctcctg gcatgctgg accttctgca
cgtggctcgg gacattgcct gtggctgtca gtatttggag gaaaaccact tcatccaccg agacattgct gccagaaact
gcctcttgac ctgtccaggc cctgaagag tggccaagat tggagacttc gggatggccc gagacatcta cagggcgagc
tactatagaa agggaggctg tgccatgctg ccagttagtg gcagcccca agaggccttc atgaaggaa tattcacttc
taaaacagac acatggtcct ttggagtgct gctatgggaa atcttttctc ttggatatat gccataccc agcaaaagca
accaggaagt tctggagttt gtcaccagtg gaggccggat ggaccaccac aagaactgcc ctgggcctgt ataccggata
atgactcagt gctggcaaca tcagcctgaa gacaggccca actttgccat cattttggag aggattgaat actgcaccca
ggaccgggat gtaatcaaca ccgctttgcc gatagaatat ggtccacttg tggaagagga agagaaagtg cctgtgagc
ccaaggaccc tgaggggtt cctcctctcc tggtctctca acaggcaaaa cgggaggagg agcgcagccc agctgcccca
ccacctctgc ctaccacctc ctctggcaag gctgcaaaga aacccacagc tgcagatc tctgttcgag tccctagagg
gccggccgtg gaaggggac acgtgaatat ggcattctct cagtccaacc ctccttcgga gttgcaaag gtccacggat
ccagaaacaa gcccaccagc ttgtgaacc caacgtacgg ctcctggttt acagagaaac ccaccaaaaa gaataatcct
atagcaaaga aggagccaca cgacagggt aacctgggc tggaggaag ctgtactgtc ccacctaacg ttgcaactgg
gagacttccg ggggcctcac tgctcctaga gccctcttcg ctgactgcca atatgaagga ggtacctctg ttcaggctac
gtcacttccc ttgtgggaat gtcaattacg gctaccagca acagggcttg ccttagaag ccgctactgc ccctggagct
ggtcattacg aggataccat tctgaaaagc aagaatagca tgaaccagcc tgggccctga
```

Figure 9B

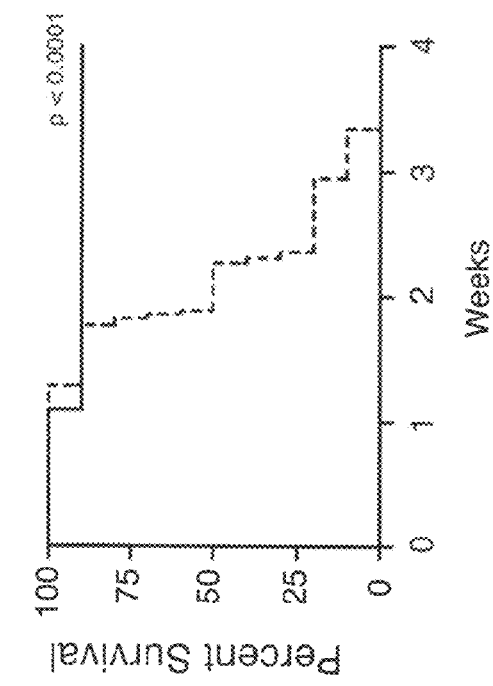
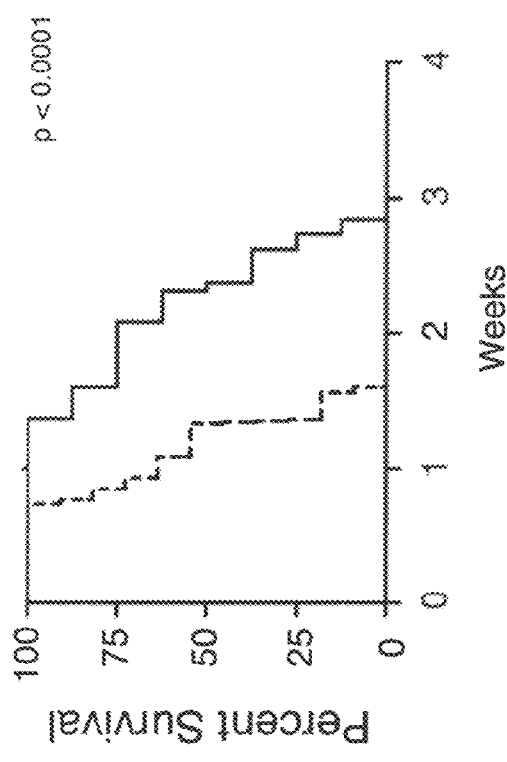
Figure 14A
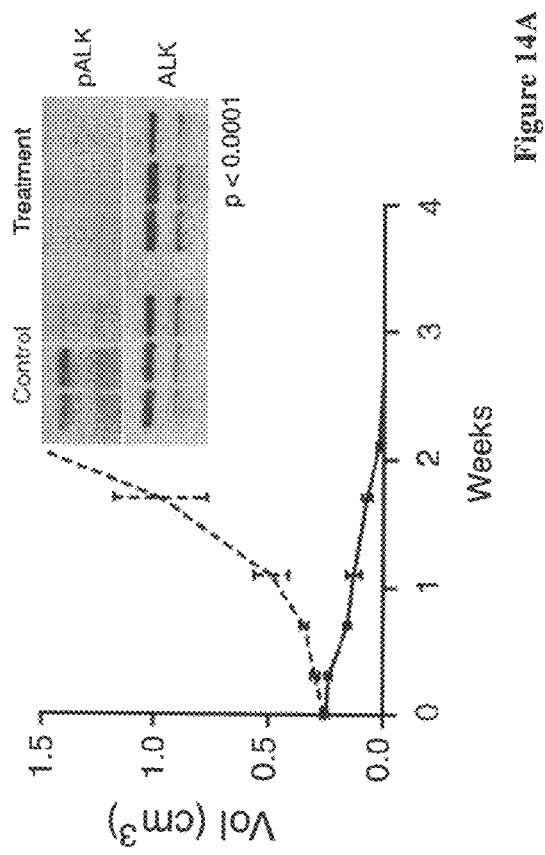
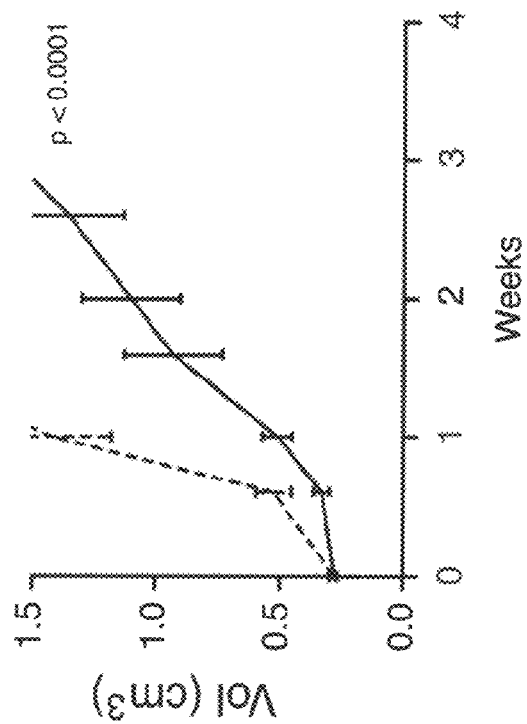
Figure 14B

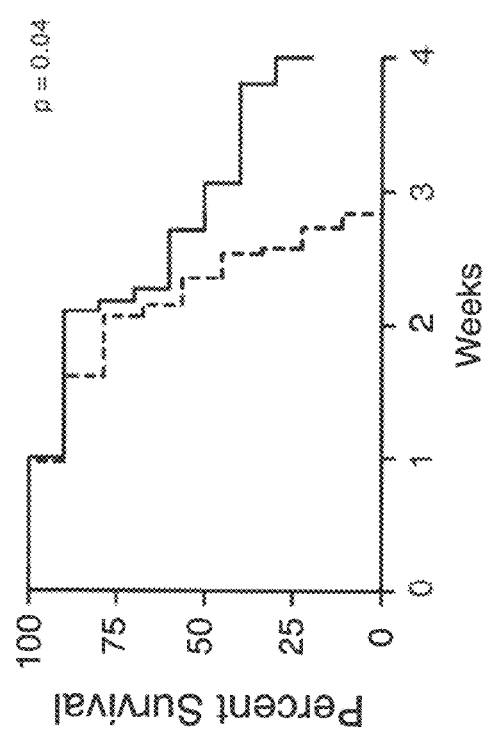
Figure 14C
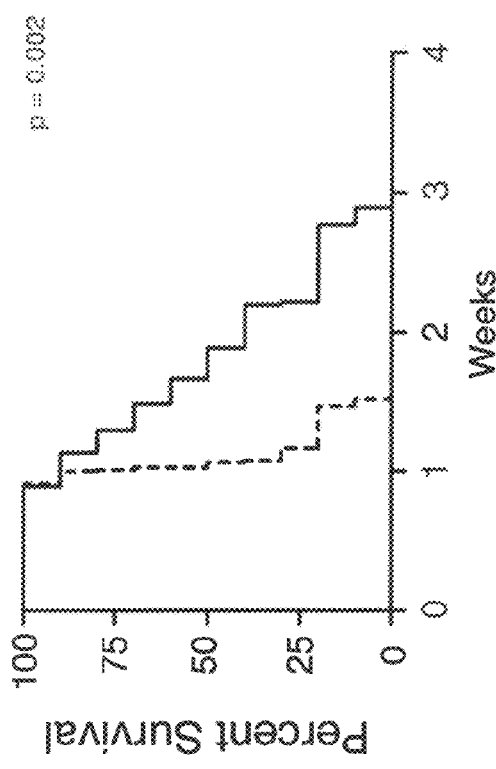
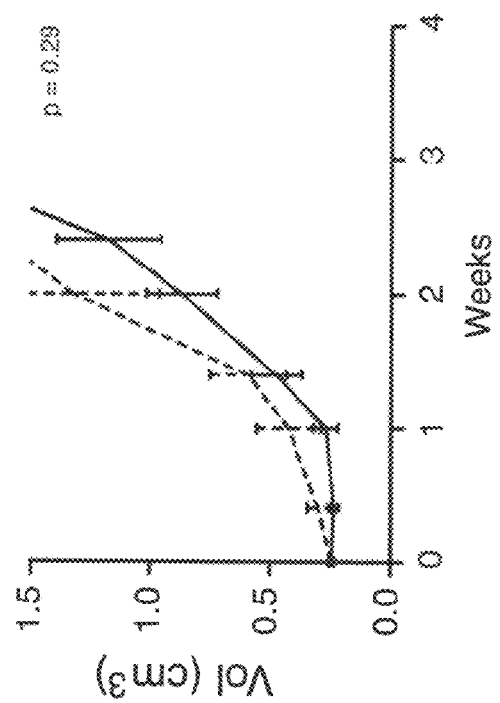
Figure 14D
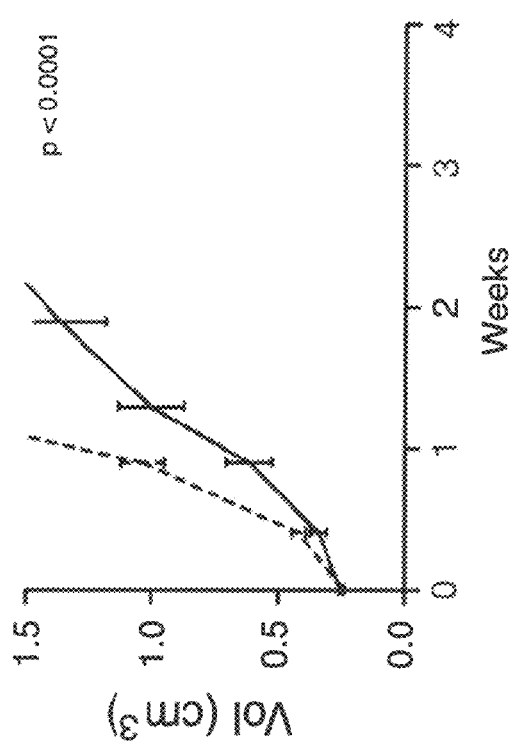

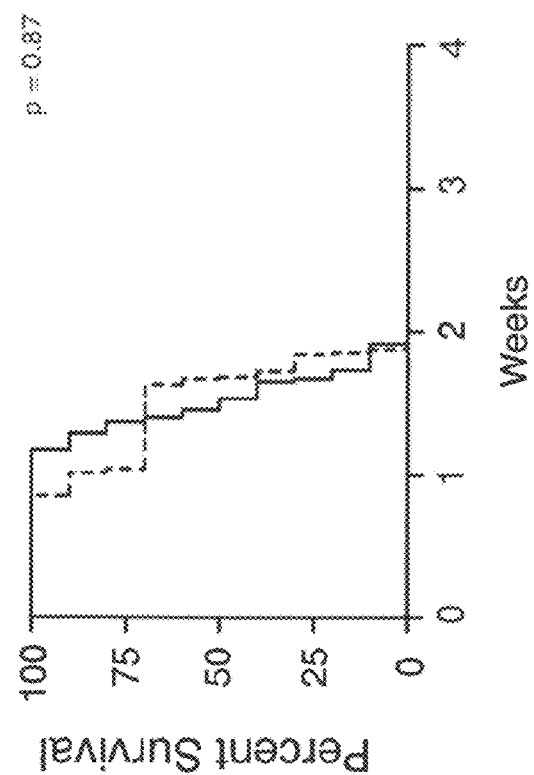
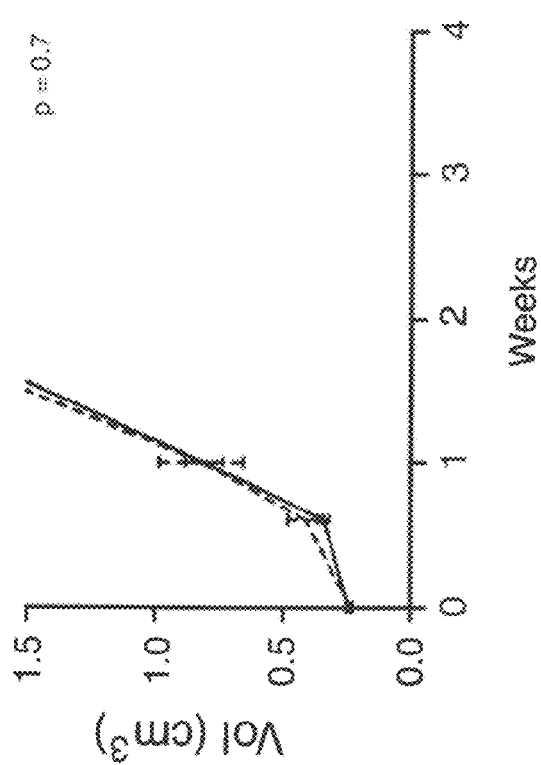
Figure 14E

METHODS AND COMPOSITIONS FOR TREATING NEUROBLASTOMA

This application is a continuation application of U.S. patent application Ser. No. 13/072,090, filed Mar. 25, 2011, now abandoned, which is a continuation-in-part of U.S. patent application Ser. No. 12/853,834, filed Aug. 10, 2010, now abandoned, which is a continuation-in-part of PCT/US2009/034288, filed on Feb. 17, 2009, which claims priority under 35 U.S.C. § 119(e) to U.S. Provisional Patent Application No. 61/029,212, filed on Feb. 15, 2008 and to U.S. Provisional Patent Application No. 61/123,775, filed on Apr. 11, 2008. The foregoing applications are incorporated by reference herein.

FIELD OF THE INVENTION

The present invention relates to the fields of neuroblastoma. More specifically, the invention provides compositions and methods for the identification, diagnosis, and treatment of neuroblastoma.

BACKGROUND OF THE INVENTION

Several publications and patent documents are cited throughout the specification in order to describe the state of the art to which this invention pertains. Each of these citations is incorporated herein by reference as though set forth in full.

Neuroblastoma is a cancer of early childhood that arises from the developing autonomic nervous system. It is the most common malignancy diagnosed in the first year of life and shows a wide range of clinical phenotypes with some patients having tumors that regress spontaneously, whereas the majority of patients have aggressive metastatic disease (Maris et al. (2007) Lancet 369:2106-20). These latter neuroblastoma cases have survival probabilities of less then 40% despite intensive chemoradiotherapy, and the disease continues to account for 15% of childhood cancer mortality (Maris et al. (2007) Lancet, 369:2106-20; Matthay et al. (1999) N. Eng. J. Med., 341:1165-73). Tumors from patients with an aggressive phenotype often show amplification of the MYCN oncogene (Schwab et al. (1984) Nature, 308:288-91), and/or deletions of chromosome arms 1p and 11q (Attiyeh et al. (2005) N. Engl. J. Med., 353:2243-53). However, because MYCN is so aberrantly dysregulated, and no putative tumor suppressor gene at 1p and 11q has been shown to harbor inactivating mutations in more than a small percentage of cases, no tractable molecular target approaches currently exist for this disease.

Like most human cancers, a small subset of neuroblastoma cases are inherited in an autosomal dominant manner (Knudson et al. (1972) Amer. J. Hum. Genet., 24:514-522; Kushner et al. (1986) Cancer, 57:1887-1893; Maris et al. (1997) Eur. J. Cancer, 33:1923-1928). A family history of the disease is found in about 1-2% of newly diagnosed cases, with a standardized incidence ratio of 9.7 for siblings of index cases (Friedman et al. (2005) Cancer Epidemiol. Biomarkers Prev., 14:1922-7). Neuroblastoma pedigrees show striking heterogeneity in the type of tumors that arise, with both benign and malignant forms occurring in the same family (Maris et al. in Neuroblastoma (eds. Cheung et al.) 21-26 (Springer, Berlin, Heidelberg, N.Y., 2005). Familial neuroblastoma patients differ from those with sporadic disease in that they are diagnosed at an earlier age and/or with multiple primary tumors, clinical characteristics that are hallmarks of cancer predisposition syndromes. Because of the lethality of the condition prior to reproductive age, previous genetic linkage scans have been underpowered and results difficult to replicate (Longo et al. (2007) Hum. Hered., 63:205-11; Maris et al. (2002) Cancer Res., 62:6651-6658; Perri et al. (2002) Oncogene 21:8356-60). Remarkably, neuroblastoma can occur with a spectrum of disorders related to abnormal development of neural crest derived tissues including central congenital hypoventilation syndrome and Hirschsprung disease. Missense or nonsense mutations in PHOX2B (paired-like homeobox 2B), a homeobox gene that is a master regulator of normal autonomic nervous system development, were recently shown to predispose to this rare field defect of the sympathicoadrenal lineage tissues (Amiel et al. (2003) Nat. Genet., 33:459-61; Mosse et al. (2004) Am. J. Hum. Genet., 75:727-30; Trochet et al. Am. J. Hum. Genet., 74:761-4). However, PHOX2B mutations explain only a small subset of hereditary neuroblastoma, are almost exclusive to cases with associated disorders of neural crest-derived tissues, and are not somatically acquired in tumors (Raabe et al. (2008) Oncogene, 27:469-76; van Limpt et al. (2004) Oncogene, 23:9280-8), leaving the genetic etiology for the majority of familial neuroblastoma cases unknown.

SUMMARY OF THE INVENTION

In accordance with the present invention, methods of detecting an increased risk for neuroblastoma in a subject are provided. Methods of diagnosing and/or prognosing neuroblastoma in a subject are also provided. In a particular embodiment, the method comprises obtaining a biological sample from the subject and determining whether the anaplastic lymphoma kinase (ALK) gene and/or protein is altered in the biological sample, wherein the presence of the alteration of the ALK gene and/or protein is indicative of neuroblastoma in the subject and/or indicative of an increased risk of metastasis and/or death. In another embodiment, the alteration in the ALK gene is selected from the group consisting of an amplification the ALK copy number, presence of at least one mutation which increases ALK activity, increased levels of ALK phosphorylation, and a translocation involving ALK which increases ALK activity. In a particular embodiment, the ALK mutations which increase ALK activity are in the tyrosine kinase domain.

In accordance with another aspect of the instant invention, methods for treating, inhibiting, and/or preventing (e.g., inhibiting the onset) neuroblastoma in a patient are provided. In a particular embodiment, the methods comprise the administration of at least one composition comprising at least one ALK inhibitor and, optionally, at least one chemotherapeutic agent. In another embodiment, the methods comprise the administration of at least one composition comprising at least one ALK antibody and, optionally, at least one ALK inhibitor, at least one other chemotherapeutic agent or therapy, and/or at least one GD2 antibody. In another embodiment, the patient is screened prior to administration of the composition in order to determine which ALK inhibitor is most effective against the particular neuroblastoma of the patient.

In yet another aspect of the invention, methods of determining whether a compound is effective for treating neuroblastoma are provided. In one embodiment, the method comprises contacting cells comprising mutations in ALK or an amplification of ALK encoding nucleic acid molecules, with at least one compound; and determining the ALK activity or cell viability or proliferation, wherein a reduction in ALK activity or cell viability or proliferation indicates the compound is therapeutic for treating a neuroblastoma which comprises the mutation or amplification.

In accordance with another aspect of the instant invention, microarrays comprising oligonucleotide probes which specifically hybridize with at least one ALK mutant are provided.

BRIEF DESCRIPTION OF THE DRAWINGS

FIGS. 3A-3E provide representative ALK copy number alterations in five neuroblastoma primary tumors. Hybridization intensity reflecting copy number for all SNPs along chromosome 2p in three primary tumors from patients with sporadically occurring disease is shown, represented on a logarithmic scale. MYCN amplification is present in all tumors. FIG. 3A is a regional gain (trisomy) of chromosome 2p, including the ALK locus. FIG. 3B is the focal gain of the ALK locus. FIG. 3C is the focal amplification of the ALK locus. FIGS. 3D and 3E are a complex rearrangement of the 2p locus, showing various focal amplicons, including MYCN and ALK.

FIG. 4A provides a graph showing the relative ALK expression of neuroblastoma cell lines and fetal brain determined using the 2-ΔΔCt method (Livak et al. (2001) Methods 25:402-8). Statistical significance was determined by unpaired T-test. FIG. 4B provides immunoblots showing differential ALK expression in neuroblastoma cell lines with phosphorylation of the tyrosine 1604 codon restricted to cell lines with mutations (the wild-type lines NBEC1 and NB1771 show faint phosphostaining).

FIGS. 5A-5J show cellular growth for ten neuroblastoma cell lines that were transfected with siRNAs against ALK or GAPDH (two negative controls and one positive control not shown for clarity). The x-axis is time in hours after transfection, the y-axis is percent growth normalized to the siRNA against GAPDH. FIG. 5K provides a summary of percentage growth inhibition with ALK siRNA knockdown by ALK mutational and allelic status. FIG. 5L provides an immunoblot showing a time course of ALK protein knockdown in the cell lines KELLY and SKNDZ.

FIG. 9A provides an amino acid sequence of ALK (SEQ ID NO: 5). FIG. 9B provides a nucleotide sequence of ALK (SEQ ID NO: 6).

FIG. 10B shows that ALK mRNA expression levels are significantly increased in tumors harboring either focal high level amplification (P<0.0001) or low-level regional gain (P<0.0001) when compared to tumors with no regional gain of ALK. Box and whisker plot of relative ALK mRNA expression is shown; lower and upper whiskers represent 5th and 95th percentile respectively.

FIG. 11A provides the relative ALK expression of 2 neuroblastoma cell lines (NB1 and NB1643), HTERT-RPE1 cell lines transfected with NPM-ALK and 4 ALK mutants, wild-type ALK, empty vector, and native cells, determined using the $2^{-\Delta\Delta C_T}$ method (Livak et al. (2001) Methods 25:402-408). FIG. 11B provides immunoblots showing differential pALK expression at 1 minute and 5 minutes in the various HTERT-RPE1 cells transfected with NPM-ALK, 4 ALK mutants, wild-type ALK, empty vector and native RPE1 cells.

FIG. 13A) and NB1643 (R1275Q; FIG. 13B) have similar growth inhibition. NB1 shows substantial abrogation of phosphorylation of STAT3, AKT and ERK but NB1643 does not, indicating NB1643 may signal through mutation specific pathways. SHSY5Y (FIG. 13C) shows inhibition of in vitro proliferation and abrogation of phospho-ALK at higher doses than NB1 and NB1643 indicating that PF-02341066 is less able to inhibit ALK signaling for this mutation.

FIGS. 14A-14E show PF-2341066 activity in vivo is associated with ALK mutations or ALK protein activation. CB17 scid mice were randomized to 4 weeks of PF-2341066 100 mg/kg/day via oral gavage (straight line), or vehicle (hashed line) and enrolled when xenograft volumes were 0.2-0.3 cm$^3$. Tumor volume is displayed as mean±S.E.M. The study end points for survival analysis were tumor volume ≥1.5 cm$^3$ or treatment related death NB1643 (R1275Q; FIG. 14A) xenografts treated with PF-2341066 regressed completely by day 15 (P<0.0001). The treatment arm of SHSY5Y (F1174L; FIG. 14B) showed significant tumor growth delay (P<0.0001) and prolonged survival by 7.7 days (P<0.0001). NBSD (F1174L; FIG. 14C) which were more resistant than SHSY5Y in vitro, did not show significant tumor growth delay (P=0.3), but did prolong survival by 3.7 days (P=0.04). Two xenograft lines were treated with WT ALK. NBEBc1 (WT; FIG. 14D) which has weak phospho-ALK staining showed significant delayed tumor progression (P<0.0001), and prolongation of survival by 5.1 days (p=0.0019). By contrast, SKNAS (WT; FIG. 14E) which has low ALK expression and no detectable pALK showed neither a delay in tumor growth (P=0.87) or prolongation of survival (P=0.70).

FIG. 15A provides a model of PF-02341066 binding to ALK. A homology model of the PF-02341066 binding to ALK was derived from the crystal structure of PF-02341066 bound to the kinase domain of c-Met (PDB entry=2WGJ). Only selected side chain residues are shown. FIG. 15B provides a model of the interaction between PF-02341066 and the activation loop of ALK. Van der Waals atomic surfaces are depicted for PF-02341066 and for residues 1270-1278 of the ALK model. FIG. 15C provides a model of R1275Q mutation in ALK. Modeling predicts that the side chain of R1275 is on the protein surface and that a R1275Q substitution is unlikely to result in a large destabilization of PF-02341066 binding to ALK. FIG. 15D shows that modeling predicts loss of stabilizing protein interactions in F1174L ALK. Direct interactions between F1174, F1245, and F1271 are predicted to stabilize the protein conformation necessary for tight binding of PF-02341066. Substitution of leucine at position 1174 is predicted to result in a significant decrease in attractive interactions within this hydrophobic core.

FIG. 20A shows cell growth monitored by RT-CES, revealing clear growth inhibition by the crizotinib/mAb combination. FIG. 20B provides an immunoblot analysis of native ALK protein levels (upper panel) and phospho-ALK (middle panel). β-actin levels are shown as a loading control (lower panel). FIG. 20C shows the effect of crizotinib pre-treatment on anti-ALK antibody mediated ADCC. SY5Y cells were pre-incubated in the presence of crizotinib or vehicle for 48 hours, harvested, and then used as target cells in the in vitro ADCC assay. **, $p<0.01$; *, $p<0.05$.

FIG. 21A shows the comparison of growth inhibition for monotherapy versus dual ALK targeting: white bars represent crizotinib alone, grey bars crizotinib treatment in the presence of 10 μg/ml anti-ALK. **, $p<0.01$; *, $p<0.05$. In FIG. 21B, $IC_{50}$ was calculated over a range of 10 doses of crizotinib alone (circles) or crizotinib plus 10 μg/ml anti-ALK (squares), yielding $IC_{50}$ values of 3018 nM and 1745 nM respectively.

FIG. 22A provides representative histograms showing proportion of cells in sub G0/apoptosis, G0/G1, and G2/mitosis. FIG. 22B provides the quantification of flow cytometry results. ** $p<0.01$; * $p<0.05$.

DETAILED DESCRIPTION OF THE INVENTION

Figure 1:
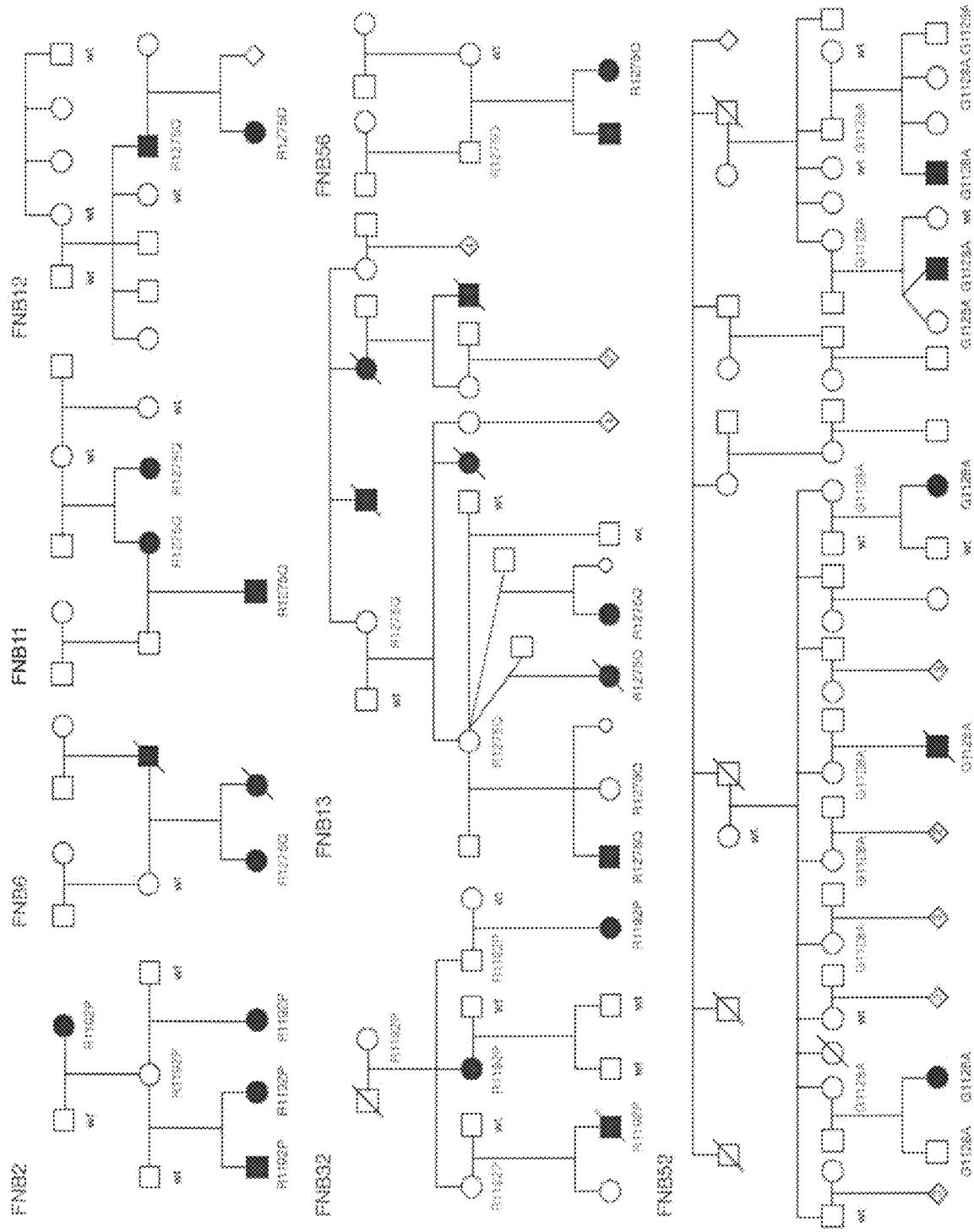
FIG. 1 is a graph of the eight neuroblastoma pedigrees with ALK mutations. All family members with DNA available for genotyping indicated with either wild type (wt) for ALK, or with mutation in the ALK tyrosine kinase domain (R1192P, R1275Q, G1128A). Individuals affected by neuroblastoma indicated by filled symbol.

As stated hereinabove, neuroblastoma is a childhood cancer that can be inherited, but the genetic etiology was largely unknown. Here it is shown that germline mutations in the anaplastic lymphoma kinase gene (ALK) explain the majority of hereditary neuroblastomas and that activating mutations can also be somatically acquired. A significant linkage signal at chromosome 2p24-23 was first identified using a whole-genome scan in neuroblastoma pedigrees. Resequencing of regional candidate genes identified three separate germline missense mutations in the tyrosine kinase domain of ALK that segregated with the disease in eight separate families. Resequencing in 194 high-risk neuroblastoma samples showed somatically (only in tumor cells) acquired mutations within the tyrosine kinase domain in 12.4%. Nine of the ten mutations map to critical regions of the kinase domain and were predicted to be oncogenic drivers with high probability. Mutations resulted in constitutive phosphorylation, and targeted knockdown of ALK mRNA resulted in profound growth inhibition of all cell lines harboring mutant or amplified ALK, as well as 2 of 6 wild type for ALK. These results demonstrate that heritable mutations of ALK are the major cause of familial neuroblastoma, and that germline or acquired activation of this cell surface kinase is a tractable therapeutic target for this lethal pediatric malignancy It has been predicted that neuroblastoma, like the analogous embryonal cancer retinoblastoma, would follow a two-hit model explaining hereditary and sporadic cases (Knudson et al. (1972) Amer. J. Hum. Genet., 24:514-522). This model has proven to be correct for the majority of childhood and adult hereditary cancers and the susceptibility genes are typically tumor suppressors where the two hits are sequential inactivation of both alleles. Discovery of heritable mutations in oncogenes as the etiology of multiple endocrine neoplasia 1 cancers (RET), papillary renal carcinoma (MET) and gastrointestinal stromal tumors (KIT) challenged this paradigm, but it is now clear that somatically acquired duplication or amplification of the mutant allele provides the second hit (Vogelstein et al. (2004) Nat. Med., 10:789-99). It is shown herein that heritable mutations in ALK are the cause of the majority of hereditary neuroblastoma cases, providing the first example of a pediatric cancer arising due to mutations in an oncogene. Taken together with the recent report that common variations at chromosome band 6p22 predispose to the development of sporadic neuroblastoma (Maris et al. (2008) N. Engl. J. Med., 358:2585-93), the genetic etiology of this disease is now being defined. The discovery of highly penetrant heritable ALK mutations as the cause of hereditary neuroblastoma are of immediate relevance to patients with a family history as screening with noninvasive techniques such as ultrasonography and measurement of urinary catecholamine metabolites should likely be implemented for unaffected children carrying an ALK mutation.

ALK is an orphan tyrosine kinase transmembrane receptor with homology to neurotrophin receptors and the MET oncogene. Expression is restricted to the developing nervous system with a postulated role in participating in the regulation of neuronal differentiation (Iwahara et al. (1997) Oncogene, 14:439-49). It is now clear that many human cancers activate ALK signaling by creating unique oncogenic fusions of ALK with a variety of partners through chromosomal translocation events (Chiarle et al. (2008) Nat. Rev. Cancer, 8:11-23). Previous work had shown that a substantial percentage of human-derived neuroblastoma cell lines express ALK transcripts and ALK protein (Lamant et al. (2000) Am. J. Pathol., 156:1711-21), but no definitive role for this oncogene had been proven (Osajima-Hakomori et al. (2005) Am. J. Pathol., 167:213-22; Motegi et al. (2004) J. Cell Sci., 117:3319-29; Miyake et al. (2002) Oncogene, 21:5823-34; Dirks et al. (2002) Int. J. Cancer, 100:49-56). ALK has recently been identified as a molecular target in neuroblastoma through a screen of human cancer cell lines with pharmacologic antagonists of the ALK kinase domain (McDermott et al. (2008) Cancer Res., 68:3389-95). The data herein provides the first evidence for oncogenic activation of ALK via mutation of the kinase domain, and these data provide the genetic basis for the observation of sensitization to ALK kinase inhibition. In addition, the discoveries in neuroblastoma may lead to future resequencing efforts in other malignancies, especially those where oncogenic fusion proteins have recently been discovered. The data presented here clearly establish ALK as critical neuroblastoma oncogene and should increase efforts to identify the ligand for this receptor and understand if ALK-mediated signaling can be activated by mechanisms other than direct mutation and/or amplification of ALK alleles. Finally, receptor tyrosine kinases provide tractable targets for pharmacologic inhibition, and allows for therapeutic strategies aimed at inhibiting ALK-mediated signaling.

In accordance with the instant invention, methods of identifying, determining an increased risk for, diagnosing, and/or prognosing a cancer in a patient are provided, wherein the method comprises determining the level/activity of ALK. In a particular embodiment, the cancer is neuroblastoma. In another embodiment, the cancer has been characterized as having an ALK translocation (e.g., an ALK translocation wherein the resultant ALK fusion protein is constitutively active). Such cancers include, without limitation, lymphomas, non-Hodgkin's lymphoma, anaplasic large cell lymphoma, inflammatory myofibroblastic tumors, and non-small-cell lung cancer. The methods may further comprise obtaining a biological sample from the subject. In a particular embodiment, the biological sample is tumor tissue or blood.

In one embodiment, the method comprises determining the presence of at least one mutation in ALK, particularly one which leads to increased activity of ALK (e.g., increased kinase activity). According to one embodiment, the mutation is within the kinase domain. In another embodiment, at least one amino acid at position P36, P157, V198, G640, L684, G718, D993, L1204, I1170, A1200, L1204, F1245, G1128, R1192, R1275, D1091, M1166, I1171, F1174, F1245, 11250, and those set forth in Tables 2A and 2B (e.g., T1151, L1196, R259, M770, E1407, E1433, R1464, G1494, A1553) is altered (mutated). In another embodiment, at least one amino acid at position G1128, R1192, R1275, D1091, M1166, I1171, F1174, F1245, and 11250 is altered (mutated). In still another embodiment, at least one amino acid at position G1128, R1192, L1204, 11250, R1275, and those set forth in Tables 2A and 2B (e.g., P36, V198, R259, G640, D993, E1407, and A1553); particularly, at least one amino acid at position G1128, R1192, and R1275 is altered (mutated; particularly those set forth below) when the germline is examined (e.g., when the biological sample is not tumor tissue). In one embodiment, at least one amino acid at position P36, P157, V198, G640, L684, G718, D993, L1204, I1170, A1200, L1204, G1128, R1192, R1275, D1091, M1166, I1171, F1174, F1245, 11250 and those set forth in Tables 2A and 2B (e.g., T1151, I1170, L1196, R259, M770, E1407, E1433, R1464, G1494, A1553); particularly, at least one amino acid at position P36, P157, V198, G640, L684, G718, G718, D993, L1204, I1170, A1200, L1204, F1245, R1275, D1091, M1166, I1171, F1174, F1245, and 11250; particularly, at least one amino acid at position R1275, D1091, M1166, I1171, F1174, F1245, and 11250 is altered (mutated; particularly those set forth below) when somatic mutations are examined (e.g., when the biological sample is tumor tissue/cells). In another embodiment, the mutation may be a nonconservative amino acid substitution. In still another embodiment, the ALK comprises at least one mutation selected from the group consisting of P36S, P157S, V198M, G640R, L684M, G718F, G718S, D993G, L1204F, I1170S, A1200V, L1204F, F1245I, G1128A, R1192P, R1275Q, D1091N, M1166R, I1171N, F1174I, F1174L, F1245C, F1245V, I1250T, and those set forth in Tables 2A and 2B (e.g., T1151M, I1170S, F1174C, L1196M, F1245I, R259H, M770I, E1407K, E1433del, R1464G, G1494R, and A1553P). In another embodiment, at least one mutation selected from the group consisting of G1128A, R1192P, R1275Q, D1091N, M1166R, I1171N, F1174I, F1174L, F1245C, F1245V, and I1250T. In yet another embodiment, at least one of the mutations is to amino acid R1275 and/or F1174, particularly at least one of R1275Q, F1174I, and F1174L. The presence of at least one of the above mutations is indicative of neuroblastoma or at least an increased risk of developing neuroblastoma in the patient. The presence of at least one of the above mutations is also indicative of a poor prognosis with increased risk of metastasis and higher risk of death. While the above mutations can be detected by sequencing the ALK protein in a biological sample obtained from a subject, it is preferred that the nucleic acid molecule encoding ALK is examined in the instant methods (after obtaining (e.g., isolating) from a biological sample from a subject). The ability to detect the above mutations in a nucleic acid molecule/protein are well known in the art and include, without limitation, sequencing, PCR (e.g., real time PCR; e.g., with mutation specific primers; optionally with subsequent sequencing or hybridization), hybridization techniques (e.g., with mutation specific probes (probes which specifically bind a mutated ALK to the exclusion of wild-type ALK); e.g., microarrays, Southern, Northern), and antibodies (e.g., those specific for at least one mutant).

In yet another embodiment, the methods of the instant invention comprise determining the ALK copy number in the cells of the biological sample obtained from a subject. A gain or amplification in the ALK copy number compared to normal human cells is indicative of neuroblastoma or at least an increased risk of developing neuroblastoma in the patient. The increased ALK copy number is also indicative of a poor prognosis with increased risk of metastasis and higher risk of death.

In still another embodiment, the methods of the instant invention comprise determining if the ALK is phosphorylated. In one embodiment, the ALK is phosphorylated to greater levels than ALK from a normal human (i.e., one that does not have cancer, particularly neuroblastoma). The ALK may be phosphorylated at positions that are not phosphorylated in normal humans and/or phosphorylated to greater levels (greater frequency) than ALK in normal humans. For example, as described hereinbelow, the constitutive phosphorylation (increased levels of phosphorylation compared to normal humans) of tyrosine at position 1604 of ALK is indicative of neuroblastoma or at least an increased risk of developing neuroblastoma in the patient. The increased ALK phosphorylation is also indicative of a poor prognosis with increased risk of metastasis and higher risk of death.

According to another aspect of the instant invention, the above methods for identifying, diagnosing, or prognosing cancer (particularly neuroblastoma) in a patient, further comprises identifying mutations in the phox2B gene/protein (e.g., 676delG) or amplification of the phoX2B gene/protein (see, e.g., Mosse et al. (2004) Am. J. Hum. Genet., 75:727-730; Rabbe et al. (2008) Oncogene 27:469-476).

In accordance with another aspect of the instant invention, methods for treating cancer, particularly a neuroblastoma, in a patient are provided, where the method comprises the administration of a composition comprising at least one ALK inhibitor (e.g., an inhibitor of ALK kinase activity) and at least one pharmaceutically acceptable carrier. The method may further comprise determining the particular ALK alteration of the patient prior to administration (see above) and administering the ALK inhibitor most effective for the ALK alteration identified (see below). Examples of ALK inhibitors include, without limitation, ALK siRNA and/or antisense molecules, small molecule inhibitors, PF-02341066 (Pfizer), TAE684 (Novartis), and CEP-14083 (Cephalon). The methods may also comprise the administration of an antibody (or fragment thereof) specific for ALK (e.g., monoclonal antibodies). In a particular embodiment, the antibodies are specific for the extracellular domain of ALK (e.g., the extracellular domain that remains after proteolytic cleavage from the 220 kDa to 140 kDa species). The antibodies may be administered separately (before, after, or at the same time as the ALK inhibitor) or in the same composition. The methods may also comprise the administration of at least one other chemotherapeutic agent and/or be administered in coordination with another chemotherapeutic agent or therapy (e.g., chemotherapy). The chemotherapeutic agent may be administered separately (before, after, or at the same time as the ALK inhibitor) or in the same composition. The compositions may be administered by any method such as, for example, intravenous injection into the blood stream, oral administration, or by subcutaneous, intramuscular or intraperitoneal injection. As stated hereinabove, the methods may also further comprise first screening the subject to determine the ALK mutation (including amplification of copy number) present in the subject as described hereinabove and selecting the appropriate ALK inhibitor for the identified mutation to administer to the patient (see below).

In accordance with another aspect of the instant invention, methods of identifying an agent which is therapeutic for the treatment of neuroblastoma are provided. In a particular embodiment, the method comprises contacting cells comprising mutations in ALK or an amplification of ALK with at least one agent and determining the ALK activity, wherein a reduction in ALK activity indicates the agent is a therapeutic agent for treating neuroblastoma. In another embodiment, the method comprises contacting cells comprising mutations in ALK or an amplification of ALK with at least one agent and determining the ability of the agent to inhibit proliferation of the cells (e.g., determining $IC_{50}$), wherein a reduction in proliferation indicates the agent is a therapeutic agent for treating a neuroblastoma characterized by the ALK mutation of the cells.

In accordance with another aspect of the present invention, microarrays for detecting ALK and/or the ALK mutants described hereinabove are provided. In a particular embodiment, the microarray comprises antibodies specific for ALK and/or the ALK mutants described hereinabove. In a preferred embodiment, the microarray comprises oligonucleotide probes which recognize ALK and/or the ALK mutants described hereinabove. The microarrays may comprise oligonucleotide probes which specifically hybridize with at least 2, at least 5, at least 10, or all of the above ALK mutants. In a particular embodiment, the microarray comprises oligonucleotide probes wherein each probe (or coordinate on the microarray) specifically hybridizes with a single ALK mutant (e.g., a single nucleotide change, a single amino acid change encompassing all codons of the amino acid change, or all changes to a single amino acid position). In a particular embodiment, the oligonucleotide probe is completely complementary to ALK (e.g., SEQ ID NO: 6) except for the mutation. In yet another embodiment, the oligonucleotide is about 10, 15, 20, 25, or 30 to about 40, 50, 75, or 100 nucleotides in length. In a particular embodiment, the oligonucleotide probes span an ALK mutant above, particularly so that the mutation is in the middle of the probe (e.g., within the middle third of the probe). In another embodiment, the microarray further comprises probes specific for wild-type ALK and/or PHOX2B (wild-type and/or mutant). In another embodiment, the microarray is contained within kit further comprising instruction material and, optionally, at least one positive control (a nucleic acid molecule recognized by an oligonucleotide probe of the microarray) and/or at least one negative control (a nucleic acid molecule not recognized by an oligonucleotide probe of the microarray).

Therapeutic Methods and Compositions

Recent studies have shown that crizotinib, a dual Met/ALK TKI, induces remarkable tumor regression in NSCLC patients harboring ALK translocations (Kwak et al. (2010) N. Engl. J. Med., 363:1693-703). Crizotinib is also currently in early-phase clinical trial testing in patients with neuroblastoma. However, preclinical studies have shown that the impact of crizotinib is highly dependent on ALK copy number and genotype. For instance, cell lines harboring the F1174L mutation, the second most common ALK mutation seen in neuroblastoma tumors, are significantly more resistant to crizotinib than those harboring the most common mutation, R1275Q (George et al. (2008) Nature 455:975-8; Sasaki et al. (2010) Cancer Res.). Moreover, resistance mutations in oncogenic ALK fusions have already emerged in early studies with crizotinib (Sasaki et al. (2010) Cancer Res.; Engelman et al. (2008) Curr. Opin. Genet. Dev., 18:73-9; Choi et al. (2010) N. Engl. J. Med., 363:1734-9). These findings underline a need for developing additional therapeutic options in neuroblastoma, where well over 50% of high-risk patients will eventually die of their disease despite major recent therapeutic advances (Maris, J. M. (2010) N. Engl. J. Med., 362:2202-11; Haupt et al. (2010) J. Clin. Oncol., 28:2331-8). One such option is immunotherapy. Herein, it is shown that ALK antibodies inhibit the growth of neuroblastoma cell lines. Further, the utility of combining ALK antibodies with TKIs is demonstrated as an important therapeutic strategy in neuroblastoma.

As taught herein, ALK is a receptor tyrosine kinase aberrantly expressed in neuroblastoma, a devastating pediatric cancer of the sympathetic nervous system. Germline and somatically acquired ALK aberrations induce increased autophosphorylation, constitutive ALK activation, and increased downstream signaling. Thus, ALK is a tractable therapeutic target in neuroblastoma which can be susceptible to both small molecule tyrosine kinase inhibitors and therapeutic antibodies. Small molecule inhibitors of ALK are available and more are currently being developed in the clinic, but common ALK mutations in neuroblastoma appear to show de novo insensitivity, arguing that complementary approaches must be developed. It is shown herein that antibody targeting of ALK is a therapeutically relevant strategy for neuroblastoma patients likely to have ALK-positive tumors. An antagonistic ALK antibody is shown herein to inhibit cell growth and induces in vitro antibody-dependent cellular cytotoxicity of human neuroblastoma-derived cell lines. Cytotoxicity was induced in cell lines harboring either wild-type or mutated forms of ALK. Treatment of neuroblastoma cells with the dual Met/ALK inhibitor crizotinib sensitized cells to antibody-induced growth inhibition by promoting cell surface accumulation of ALK and thus increasing the accessibility of antigen for antibody binding. These data clearly show that ALK-targeted immunotherapy is a strong therapeutic strategy for neuroblastomas with mutated or wild-type ALK.

Approaches for therapeutically targeting RTKs include monoclonal antibodies and small molecule tyrosine kinase inhibitors (TKIs), both of which have led to dramatic increases in survival and time to progression in certain types of cancer (Zhang (2009) Nat. Rev. Cancer 9:28-39; Weiner et al. (2010) Nat. Rev. Immunol., 10:317-27). For example, the trastuzumab antibody was approved for treatment of HER2-overexpressing breast cancer over 10 years ago, and is thought to have multiple mechanisms of action including blockade of aberrant signaling and antibody-dependent cellular cytotoxicity (ADCC) (Hudis, C. A. (2007) N. Engl. J. Med., 357:39-51). Similarly, the epidermal growth factor receptor (EGFR) antibody cetuximab inhibits binding of activating ligands and induces ADCC (Kurai et al. (2007) Clin. Cancer Res., 13:1552-61). Clinical activity of TKIs that inhibit HER2 and EGFR has been amply demonstrated. Moreover, these TKIs have been used with HER2- and EGFR-targeted antibodies in breast and lung cancer, respectively (Scaltriti et al. (2009) Oncogene 28:803-14; Regales et al. (2009) J. Clin. Invest., 119:3000-10; Xia et al. (2005) Oncogene 24:6213-21).

As stated herein, a recent phase 3 clinical trial using antibodies against the disialoganglioside GD2, which is almost uniformly expressed on neuroblastoma cell surfaces, has shown the promise of intensive targeted immunotherapy in neuroblastoma (Yu et al. (2010) N. Engl. J. Med., 363: 1324-34). It is shown herein that ALK RTK is also expressed in the vast majority of neuroblastoma cases, indicating that it represents another tractable immunotherapy target. Moreover, like GD2, ALK expression is largely limited to tumor tissue (Iwahara et al. (1997) Oncogene 14:439-49), making it an ideal target for immunotherapy while minimizing the risk of cytotoxicity in non-malignant tissue of patients treated with ALK antibodies.

Like the GD2 antibody, and several clinically successful antibodies such as trastuzumab and cetuximab, it was found herein that an ALK antibody can mediate ADCC of ALK-positive neuroblastoma cells. In the in vitro ADCC system, neuroblastoma cells were killed when treated with 1 μg/ml anti-ALK antibody, a lower dose than the 10 μg/ml clinically achieved in trastuzumab-treated breast cancer patients (Baselga et al. (1996) J. Clin. Oncol., 14:737-44), and well below the trough plasma antibody concentrations achieved in two phase I studies of lung cancer patients treated with cetuximab (Baselga et al. (2000) J. Clin. Oncol., 18:904-14; Robert et al. (2001) J. Clin. Oncol., 19:3234-43). The experiments were not designed to determine the optimal ADCC dose, but nonetheless show that antibody targeting of ALK is an important therapeutic avenue based on its ADCC effects alone. Additional studies may be performed to determine the minimum ALK antibody dose at which ADCC can be induced, the range of effective concentrations, and the dependence of ADCC sensitivity on ALK expression level and genotype.

Unlike GD2 antibodies, those that target ALK can bind and inhibit an oncogenic growth factor receptor—permitting an additional immune cell-independent component of its inhibitory mechanism, through inactivation of a constitutively activated receptor. ALK overexpression or mutation leads to its hyper-activation, autophosphorylation and elevated down-stream signaling (Osajima-Hakomori et al. (2005) Am. J. Pathol., 167:213-22), as also seen for HER2 and EGFR in breast and lung cancer (Yarden et al. (2001) Nat. Rev. Mol. Cell Biol., 2:127-37). Indeed, the oncogenic role of full-length ALK in neuroblastoma was originally discovered when activating mutations in ALK, which occur in roughly 8% of patient tumors, were discovered in the germline of patients with the hereditary form of neuroblastoma, and were subsequently found to be somatically acquired (George et al. (2007) PLoS One 2:e255; Janoueix-Lerosey et al. (2008) Nature 455:967-70; Mosse et al. (2008) Nature 455:930-5; Chen et al. (2008) Nature 455:971-4). It has also been shown that whereas native ALK expression levels predict improved survival, high levels of ALK expression (which promotes its activation) are associated with decreased survival (see also De Brouwer et al. (2010) Clin. Cancer Res., 16:4353-62). Thus, ALK signaling—enhanced by mutation or overexpression—appears to play an important role in initiation and/or maintenance of neuroblastoma. ALK inhibition with the TKI crizotinib is likely to be an important tool in treating ALK-dependent neuroblastoma, but it is already clear that certain ALK-activating mutations reduce sensitivity to this drug. Antagonistic ALK antibodies provide a superior approach to ALK inhibition. It is shown herein that an antagonist ALK antibody inhibits growth of neuroblastoma cells over a range of doses, all of which are below (or equal to) those reported to be clinically achievable in patients with trastuzumab or cetuximab. The ALK antibody inhibits growth in neuroblastoma cell lines that harbor either amplified/over expressed ALK (NB1) or ALK with the most common constitutively activating mutations (R1275Q in 1643 cells, and F1174L in SY5Y cells). Notably, SY5Y cells are relatively resistant to TKI-targeting of ALK, but respond to antibody inhibition. ALK antibody therapy is, therefore, relevant for patient tumors exhibiting a broad range of ALK expression levels and aberrations.

It is also demonstrated herein that dual targeting of ALK with both antibody and TKI therapeutics produces superior results. Dual targeting has been used with other oncogenic RTKs (Scaltriti et al. (2009) Oncogene 28:803-14; Xia et al. (2005) Oncogene 24:6213-21; Johns et al. (2003) Proc. Natl. Acad. Sci., 100:15871-6; Konecny et al. (2006) Cancer Res., 66:1630-9; Matar et al. (2004) Clin. Cancer Res., 10:6487-501). For example, for NSCLC expressing erlotinib-resistant $EGFR^{T790M}$, such dual targeting induced tumor regression (Regales et al. (2009) J. Clin. Invest., 119:3000-10). For ALK-expressing neuroblastoma cell lines, crizotinib treatment enhances cell surface expression of ALK, leading both to enhanced ADCC and elevated immune cell-independent growth inhibition and cytotoxicity. For F1174L-expressing SY5Y cells, for example, combined antibody/TKI treatment led to almost complete growth inhibition, and induced a significantly higher level of apoptosis than either crizotinib or antibody alone. Importantly, the antibody/TKI combination therapy demonstrated efficacy at low (10 nM) doses of crizotinib and antibody reduced the $IC_{50}$ for crizotinib treatment by half. This shows that dual ALK targeting is a relevant therapeutic strategy for decreasing the dose-dependent toxicities associated with TKI therapy and can delay or prevent TKI resistance.

In accordance with the instant invention, methods for inhibiting, reducing the progression of, and/or treating cancer, particularly a neuroblastoma, in a subject (e.g., human or animal) are provided. The neuroblastoma may be resistant to an ALK inhibitor (e.g., crizotinib).

In a particular embodiment, the method comprises the administration of at least one ALK antibody to a subject. In a particular embodiment, the antibody is immunologically specific for the extracellular domain of ALK (e.g., the extracellular domain that remains after proteolytic cleavage from the 220 kDa to 140 kDa species, or amino acids 19-1038). ALK amino acid and nucleotide sequences are provided, e.g., in FIG. 9 as well as U.S. Pat. No. 5,770,421; GenBank Gene ID: 238; and GenBank Accession Nos. NM_004304.4 and NP_004295.2. Examples of ALK antibodies are provided, for example, in Moog-Lutz et al. (J. Biol. Chem., 280:26039-26048), Bernard-Pierrot et al. (J. Biol. Chem. (2002) 277:32071-32077), U.S. Patent Application Publication No. 2008/0118512, U.S. Patent Application Publication No. 2001/0021505, U.S. Pat. No. 5,770,421; Motegi et al. (J. Cell Sci. (2004) 117:3319-29), and Mazot et al. (Oncogene (2011) doi:10.1038/onc.2010.595).

Anti-ALK antibody of the instant invention may be modified. For example, the antibodies may be humanized to reduce immunogenicity (Jones et al. (1986) Nature 321:522-5), de-fucosylated to maximize ADCC (Niwa et al. (2005) Clin. Cancer Res., 11:2327-36), and/or conjugated to immunostimulatory cytokines such as IL-2 or cytotoxic agents (Hughes, B. (2010) Nat. Rev. Drug Discov., 9:665-7). In a particular embodiment, the anti-ALK antibody is operably linked (e.g., coupled or conjugated) to reagents that induce cell death. For example, the antibody may be linked to a cytotoxic molecule, a radioisotope, drug, and/or a chemotherapeutic agent. Cytotoxic molecules include, without limitation, complement (e.g., mouse, rat, rabbit, guinea pig, cow, horse, and human), nanoparticles and nanotubes (e.g., heat sensitive carbon nanocrystals; see e.g., Chakravarty et al. (2008) PNAS 105:8697-8702) and Cho et al. (2008) Clin.

Cancer Res., 14:1310-1316), cytoxic antibiotics (e.g., calicheamicin), cationic amphipathic lytic peptides (e.g., KLA and PTP (prostate-specific membrane antigen-targeting peptide)), radionuclides, and toxins. Toxins can be derived from various sources, such as plants, bacteria, animals, and humans or be synthetic toxins (drugs), and include, without limitation, saprin, ricin (e.g., ricin A), abrin, ethidium bromide, diptheria toxin, *Pseudomonas* exotoxin, PE40, PE38, saporin, gelonin, RNAse, peptide nucleic acids (PNAs), ribosome inactivating protein (RIP) type-1 or type-2, pokeweed anti-viral protein (PAP), bryodin, momordin, chemotherapeutic agents, and bouganin. Radionuclides (radioisotopes) of the instant invention include, without limitation, positron-emitting isotopes and alpha-, beta-, gamma-, Auger- and low energy electron-emitters. In a particular embodiment, the radionuclides are alpha-emitters or auger-emitters. The radioisotopes include, without limitation: $^{13}N$, $^{18}F$, $^{32}P$, $^{64}Cu$, $^{66}Ga$, $^{67}Ga$, $^{68}Ga$, $^{67}Cu$, $^{77}Br$, $^{80m}Br$, $^{82}Rb$, $^{86}Y$, $^{90}Y$, $^{95}Ru$, $^{97}Ru$, $^{99m}Tc$, $^{103}Ru$, $^{105}Ru$, $^{111}In$, $^{113m}In$, $^{113}Sn$, $^{121m}Te$, $^{122m}Te$, $^{125m}Te$, $^{123}I$, $^{124}I$, $^{125}I$, $^{126}I$, $^{131}I$, $^{133}I$, $^{165}Tm$, $^{167}Tm$, $^{168}Tm$, $^{177}Lu$, $^{186}Re$, $^{188}Re$, $^{195m}Hg$, $^{211}At$, $^{212}Bi$, $^{213}Bi$, and $^{225}Ac$. In yet another embodiment, the radionuclide containing molecule can be administered with a radiosensitizer.

In a particular embodiment, the method further comprises the administration of at least one ALK inhibitor (e.g., an inhibitor of ALK kinase activity) to the subject. The ALK inhibitor may be administered before, after, and/or simultaneously (e.g., in the same composition or in different compositions) with the ALK antibody. In a particular embodiment, the ALK inhibitor is a small molecule inhibitor (e.g., an ATP-competitive, small-molecule inhibitor of the receptor tyrosine kinase). Examples of ALK inhibitors include, without limitation, crizotinib (PF-02341066, Pfizer), LDK378 (Novartis), TAE684 (Novartis), CEP-14083 (Cephalon, Frazer, Pa.), CEP-37440 (Cephalon), CEP-28122 (Cephalon), CEP-14513 (Cephalon), AF802 (Chugai (Japan), Roche), AP26113 (Ariad; Cambridge, Mass.), and the compounds in U.S. Pat. Nos. 7,601,716; 7,910,585; 7,893,074; and 7,671,063, and U.S. Patent Application Publication Nos. 2009/0131436, 2009/0221555, and 2009/0286778. In a particular embodiment, the ALK inhibitor is crizotinib.

The methods may also comprise the administration of at least one other chemotherapeutic agent and/or be administered in coordination with another chemotherapeutic agent or therapy (e.g., chemotherapy, radiation, etc.). In a particular embodiment, disialoganglioside GD2 antibodies (Yu et al. (2010) N. Engl. J. Med., 363:1324-34) are also administered. The chemotherapeutic agent may be administered separately (before, after, or at the same time as the ALK inhibitor and/or ALK antibody) or in the same composition. As stated hereinabove, the methods may also further comprise first screening the subject to determine the ALK mutation (including amplification of copy number) present in the subject as described hereinabove and selecting the appropriate ALK inhibitor and/or antibody for the identified mutation to administer to the patient.

Compositions comprising the above ALK therapeutics are also encompassed by the instant invention. In a particular embodiment, the composition comprises at least one ALK antibody and at least one pharmaceutically acceptable carrier. The composition may further comprise at least one ALK inhibitor, chemotherapeutic agent, and/or at least one GD2 antibody. In yet another embodiment, kits comprising at least one of the above compositions are encompassed by the instant invention. For example, the kit may comprise a first composition comprising at least one ALK antibody and at least one carrier and a second composition comprising at least one ALK inhibitor and at least one carrier.

The compositions described herein will generally be administered to a patient as a pharmaceutical preparation. The term "patient" as used herein refers to human or animal subjects. These compositions may be employed therapeutically, under the guidance of a physician.

The compositions of the instant invention may be conveniently formulated for administration with any pharmaceutically acceptable carrier(s). For example, the agents may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the agents in the chosen medium may be varied and the medium may be chosen based on the desired route of administration of the pharmaceutical preparation. Except insofar as any conventional media or agent is incompatible with the agents to be administered, its use in the pharmaceutical preparation is contemplated.

The dose and dosage regimen of compositions according to the invention that are suitable for administration to a particular patient may be determined by a physician considering the patient's age, sex, weight, general medical condition, and the specific condition for which the composition is being administered and the severity thereof. The physician may also take into account the route of administration, the pharmaceutical carrier, and the composition's biological activity.

Selection of a suitable pharmaceutical preparation will also depend upon the mode of administration chosen. For example, the compositions of the invention may be administered intravenously. In this instance, a pharmaceutical preparation comprises the agents dispersed in a medium that is compatible with intravenous injection.

Compositions of the instant invention may be administered by any method. For example, the compositions of the instant invention can be administered, without limitation, parenterally, subcutaneously, orally (e.g., liquid or pill/capsule/tablet form), topically, pulmonarily, intravenously, intraperitoneally, intrathecally, epidurally, intramuscularly, intradermally. In a particular embodiment, the compositions are administered intravenously or orally. Pharmaceutical preparations for injection and oral administration are known in the art. If injection is selected as a method for administering the composition, steps must be taken to ensure that sufficient amounts of the molecules reach their target cells to exert a biological effect.

Pharmaceutical compositions containing an agent of the present invention as the active ingredient in intimate admixture with a pharmaceutically acceptable carrier can be prepared according to conventional pharmaceutical compounding techniques. The carrier may take a wide variety of forms depending on the form of preparation desired for administration, e.g., intravenous.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of compositions of the instant invention may be determined by evaluating the toxicity of the molecules or cells in animal models. Various concentrations of agents in pharmaceutical preparations may be administered to mice, and the minimal and maximal dosages may be determined based on the beneficial results and side effects observed as a result of the treatment. Appropriate dosage unit may also be determined by assessing the efficacy of the agent treatment in combination with other standard drugs. The dosage units of the compositions may be determined individually or in combination with each treatment according to the effect detected.

The pharmaceutical preparation comprising the agents of the instant invention may be administered at appropriate intervals, for example, at least once or twice a day or more until the pathological symptoms are reduced or alleviated, after which the dosage may be reduced to a maintenance level. The appropriate interval in a particular case would normally depend on the condition of the patient.

Definitions

As used herein, a "biological sample" refers to a sample of biological material obtained from a subject, preferably a human subject, including a tissue, a tissue sample, a cell sample, a tumor sample, and a biological fluid, e.g., blood or urine. A biological sample may be obtained in the form of, e.g., a tissue biopsy, such as, an aspiration biopsy, a brush biopsy, a surface biopsy, a needle biopsy, a punch biopsy, an excision biopsy, an open biopsy, an incision biopsy and an endoscopic biopsy.

As used herein, "diagnose" refers to detecting and identifying a disease in a subject. The term may also encompass assessing or evaluating the disease status (progression, regression, stabilization, response to treatment, etc.) in a patient known to have the disease.

As used herein, the term "prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis). In other words, the term "prognosis" refers to providing a prediction of the probable course and outcome of a cancer or the likelihood of recovery from the cancer.

The term "treat" as used herein refers to any type of treatment that imparts a benefit to a patient afflicted with a disease, including improvement in the condition of the patient (e.g., in one or more symptoms), delay in the progression of the condition, etc.

The phrase "effective amount" refers to that amount of therapeutic agent that results in an improvement in the patient's condition.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), water, aqueous solutions, oils, bulking substance (e.g., lactose, mannitol), excipient, auxilliary agent or vehicle with which an active agent of the present invention is administered. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, 20th Edition, (Lippincott, Williams and Wilkins), 2000; Liberman, et al., Eds., Pharmaceutical Dosage Forms, Marcel Decker, New York, N.Y., 1980; and Kibbe, et al., Eds., Handbook of Pharmaceutical Excipients (3rd Ed.), American Pharmaceutical Association, Washington, 1999.

As used herein, a "conservative" amino acid substitution/mutation refers to substituting a particular amino acid with an amino acid having a side chain of similar nature (i.e., replacing one amino acid with another amino acid belonging to the same group). A "non-conservative" amino acid substitution/mutation refers to replacing a particular amino acid with another amino acid having a side chain of different nature (i.e., replacing one amino acid with another amino acid belonging to a different group). Groups of amino acids having a side chain of similar nature are known in the art and include, without limitation, basic amino acids (e.g., lysine, arginine, histidine); acidic amino acids (e.g., aspartic acid, glutamic acid); neutral amino acids (e.g., glycine, asparagine, glutamine, serine, threonine, tyrosine, cysteine, alanine, valine, leucine, isoleucine, proline, phenylalanine, methionine, tryptophan); amino acids having a polar side chain (e.g., glycine, asparagine, glutamine, serine, threonine, tyrosine, cysteine); amino acids having a non-polar side chain (e.g., alanine, valine, leucine, isoleucine, proline, phenylalanine, methionine, tryptophan); amino acids having an aromatic side chain (e.g., phenylalanine, tryptophan, histidine); amino acids having a side chain containing a hydroxyl group (e.g., serine, threonine, tyrosine), and the like.

As used herein, the term "amplification" when used in reference to copy number refers to the condition in which the copy number of a nucleic acid sequence is greater than the copy number of a control sequence. In other words, amplification indicates that the ratio of a particular nucleic acid sequence is greater than 1:1 when compared to a control sequence (e.g., 1.1:1, 1.2:1, or 1.3:1).

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains about 10-100, about 10-50, about 15-30, about 15-25, about 20-50, or more nucleotides, although it may contain fewer nucleotides. The probes herein may be selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target, although they may. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically about 10-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., 1989, Molecular Cloning: A Laboratory Manual, Cold Spring Harbor Laboratory Press):

$$Tm=81.5° C.+16.6 \text{ Log } [Na+]+0.41(\% \text{ G+C})-0.63(\% \text{ formamide})-600/\#bp \text{ in duplex}$$

As an illustration of the above formula, using [Na+]=[0.368] and 50% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated Tm of the hybrid. Wash conditions should be as stringent as possible for the degree of identity of the probe for the target. In general, wash conditions are selected to be approximately 12 20° C. below the Tm of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

An "antibody" or "antibody molecule" is any immunoglobulin, including antibodies and fragments thereof, that binds to a specific antigen. The term includes polyclonal, monoclonal, chimeric, single domain (Dab) and bispecific antibodies. As used herein, antibody or antibody molecule contemplates recombinantly generated intact immunoglobulin molecules and molecules comprising immunologically active portions of an immunoglobulin molecule such as, without limitation: Fab, Fab', F(ab')2, F(v), scFv, scFv2, scFv-Fc, minibody, diabody, tetrabody, and single variable domain (e.g., variable heavy domain, variable light domain).

With respect to antibodies, the term "immunologically specific" refers to antibodies that bind to one or more epitopes of a protein or compound of interest, but which do not substantially recognize and bind other molecules in a sample containing a mixed population of antigenic biological molecules.

The term "isolated" may refer to a compound or complex that has been sufficiently separated from other compounds with which it would naturally be associated. "Isolated" is not meant to exclude artificial or synthetic mixtures with other compounds or materials, or the presence of impurities that do not interfere with fundamental activity or ensuing assays, and that may be present, for example, due to incomplete purification, or the addition of stabilizers.

As used herein, an "instructional material" includes a publication, a recording, a diagram, or any other medium of expression which can be used to communicate the usefulness of the composition of the invention for performing a method of the invention.

The phrase "solid support" refers to any solid surface including, without limitation, any chip (for example, silica-based, glass, or gold chip), glass slide, membrane, plate, bead, solid particle (for example, agarose, sepharose, polystyrene or magnetic bead), column (or column material), test tube, or microtiter dish.

As used herein, the term "microarray" refers to an ordered arrangement of hybridizable array elements. The array elements are arranged so that there are at least one or more different array elements on a solid support. Preferably, the array elements comprise oligonucleotide probes.

As used herein, the term "small molecule" refers to a substance or compound that has a relatively low molecular weight (e.g., less than 2,000). Typically, small molecules are organic, but are not proteins, polypeptides, or nucleic acids.

Chemotherapeutic agents are compounds that exhibit anticancer activity and/or are detrimental to a cell (e.g., a toxin). Suitable chemotherapeutic agents include, but are not limited to: toxins (e.g., saporin, ricin, abrin, ethidium bromide, diptheria toxin, and *Pseudomonas* exotoxin); taxanes; alkylating agents (e.g., temozolomide, nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes (e.g., cisplatin, carboplatin, tetraplatin, ormaplatin, thioplatin, satraplatin, nedaplatin, oxaliplatin, heptaplatin, iproplatin, transplatin, and lobaplatin); bioreductive alkylators such as mitomycin, procarbazine, dacarbazine and altretamine); DNA strand-breakage agents (e.g., bleomycin); topoisomerase II inhibitors (e.g., amsacrine, menogaril, amonafide, dactinomycin, daunorubicin, N,N-dibenzyl daunomycin, ellipticine, daunomycin, pyrazoloacridine, idarubicin, mitoxantrone, m-AMSA, bisantrene, doxorubicin (adriamycin), deoxydoxorubicin, etoposide (VP-16), etoposide phosphate, oxanthrazole, rubidazone, epirubicin, bleomycin, and teniposide); DNA minor groove binding agents (e.g., plicamydin); antimetabolites (e.g., folate antagonists such as methotrexate and trimetrexate); pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); anthracyclines; and tubulin interactive agents (e.g., vincristine, vinblastine, and paclitaxel (Taxol®)).

Radiation therapy refers to the use of high-energy radiation from x-rays, gamma rays, neutrons, protons and other sources to target cancer cells. Radiation may be administered externally or it may be administered using radioactive material given internally. Chemoradiation therapy combines chemotherapy and radiation therapy.

The following examples are provided to illustrate certain embodiments of the invention. They are not intended to limit the invention in any way.

Example 1

Methods

Summary

Twenty probands with neuroblastoma and a family history of the disease were identified for study. Eight pedigrees had 3 or more affected individuals; six pedigrees contained only two affected individuals, but of first degree relation; and six pedigrees consisted of only two affected individuals, but of second, third, or >fourth degree relationship. A total of 176 individuals (49 affected with neuroblastoma) were genotyped genome-wide, and two families were excluded due to insufficient DNA for genotyping. Marker data was simulated under a model of genetic homogeneity and autosomal dominant inheritance, and the data was analyzed using an affected-only approach comparable to the model-free approach used in the actual linkage analysis. Genotype data were checked for Mendelian inconsistencies using PED-STATS (Wigginton et al. (2005) Bioinformatics, 21:3445-7), and analyzed for linkage using MERLIN (Abecasis et al. (2002) Nat. Genet., 30:97-101) and LAMP (Li et al. (2005) Am. J. Hum. Genet., 76:934-49). Regional candidates were re-sequenced using Sanger methodology. Predictions on the probability that DNA sequence alterations encode a mutant protein were performed using a support vector machine-based statistical classifier (Torkamani et al., (2007) Bioinformatics, 23:2918-25; Torkamani et al. (2008) Cancer Res., 68:1675-82). Four-hundred-and-ninety-one primary tumor samples, and 27 cell lines were used for whole genome SNP-array analyses (550K) to determine copy number alterations (Maris et al. (2008) N. Engl. J. Med., 358:2585-93). mRNA knockdown of ALK and control targets was achieved with siRNAs against each target. siRNA knockdown effects on substrate adherent growth was quantified with the RT-CES™ microelectronic cell sensor system (ACEA, San Diego, Calif.) (Yu et al. (2006) Anal. Chem., 78:35-43; Cole et al. (2008) Mol. Cancer Res., 6:735-42). Whole cell lysates were collected from the cell lines and from siALK and siNTC (non targeting control) treated cells after transfection. Proteins were separated by SDS PAGE gels and immunoblotted using ALK and Phospho-ALK antibodies.

Research Subjects and Samples

Families with a history of neuroblastoma in at least one other relative were eligible to participate. Only germline DNA from the neuroblastoma pedigrees was studied, as no tumor tissue was available. Sporadic neuroblastoma tumor samples with matched constitutional DNA were acquired from the Children's Oncology Group Neuroblastoma Tumor Bank. The Children's Hospital of Philadelphia Institutional Review Board approved this research.

Linkage Analysis

A genome-wide linkage scan was done using the Illumina Linkage IVb SNP panel. Genotype data were checked for Mendelian inconsistencies using PEDSTATS (Wigginton et al. (2005) Bioinformatics, 21:3445-7), and analyzed for linkage using MERLIN (Abecasis et al. (2002) Nat. Genet., 30:97-101) and LAMP (Li et al. (2005) Am. J. Hum. Genet., 76:934-49). The genome-wide screen for linkage was performed with both maximum likelihood allele frequency estimates and model-free analyses. Since the pattern of inheritance is complex, a model-free approach was used so as not to assume any specific mode of inheritance. Model-based analyses were performed for all SNPs included in the critical region under a dominant mode of inheritance, assuming four different gene frequencies (0.0001, 0.001, 0.01, and 0.1) and dominant transmission with varying penetrance of the disease across a broad range, from 0.0001 to 0.68. Model-based linkage analysis was also performed using the method implemented in LAMP, assuming a prevalence of the disease of 0.000143 (1/7000), and maximizing the lod-scores over all possible disease models (MOD score analysis). In every analysis, the critical interval was defined as the region with associated lod-scores greater than the maximum lod-score minus 3. Since linkage disequilibrium (LD) among markers is known to inflate the lod-scores from linkage analysis in the presence of missing founders, its impact on the lod-scores was assessed at the chromosome 2p critical interval. To model LD, markers were organized into clusters by means of Merlin, which uses population haplotype frequencies derived from the HapMap project (www.hapmap.org/).

DNA Sequencing

Shotgun resequencing from templates generated by long PCR for an 18 kilobase region surrounding the MYCN locus was performed using a 454 Life Sciences instrument (Branford, Conn.) after bi-directional sequencing of the three coding exons showed no disease causal sequence variations in the pedigrees. Bi-directional sequencing of ALK coding sequence was performed in the following distinct sample sets: 1) constitutional DNA from the proband and an unaffected first degree relative from the twenty neuroblastoma pedigrees, with repeat sequencing of amplicons containing any DNA sequence variations and sequencing of amplicons containing confirmed variations in remaining family members; 2) 27 human neuroblastoma-derived cell line DNAs maintained at the Children's Hospital of Philadelphia; 3) tumor DNA from 167 sporadic neuroblastomas from the Children's Oncology Group tumor bank; and 4) 109 normal constitutional DNAs from the SNP500Cancer Resource panel purchased from the Coriell Institute for Medical Research (Camden, N.J.). In order to verify neuroblastoma cell line integrity, all lines were routinely genotyped (AmpFLSTR Identifier kit; Applied Biosystems, Foster City, Calif.), and mycoplasma tested.

Mutation Prediction

Cancer mutant predictions and analysis were performed as described (Torkamani et al. (2008) Cancer Res., 68:1675-82). Briefly, a support vector machine was trained upon common SNPs (presumed neutral) and congenital disease causing SNPs characterized by a variety of sequence, structural, and phylogenetic parameters. Training and predictions were performed using somatic mutations occurring within and outside of the kinase catalytic core separately. The support vector machine-based method was then applied to the ALK mutants, and the probability that each mutant is a driver was computed via the support vector machine. The threshold taken for calling a SNP a driver was taken to be 0.49 for catalytic domain mutations, and 0.53 for all other mutations (Torkamani et al. (2007) Bioinformatics, 23:2918-25). For comparison to previously observed cancer mutations, ALK mutants were mapped to positions of a catalytic core alignment generated with characteristic site motifs, and previously observed cancer mutants mapping to the same positions were noted (Torkamani et al. (2008) Cancer Res., 68:1675-82).

Tumor Copy Number Analysis

Tumor samples were assayed on the Illumina Infinium™ II HumanHap550 BeadChip technology (Illumina, San Diego, Calif.), at the Center for Applied Genomics at the Children's Hospital of Philadelphia. A total of 750 nanograms of genomic DNA was used as input in each case, and the assay was performed and data analyzed following the manufacturers recommendations and as previously described (Maris et al. (2008) N. Engl. J. Med., 358:2585-93).

Quantitative mRNA Expression

Relative ALK expression was determined using the 2-ΔΔCt method (Livak et al. (2001) Methods 25:402-8), using GAPDH as the endogenous control and using the second dCT as the lowest expressed cell line, using methods as previously described (Cole et al. (2008) Mol. Cancer Res., 6:735-42).

ALK siRNA Knockdown in Neuroblastoma Cell Lines

A total of 1-5×10$^4$ neuroblastoma cells were plated in triplicate overnight in antibiotic-free complete media in the 96 well RT-CES™ microelectronic cell sensor system (ACEA, San Diego, Calif.) (Yu et al. (2006) Anal. Chem., 78:35-43; Cole et al. (2008) Mol. Cancer Res., 6:735-42). The cells were then transiently transfected with 200 µL containing 50 nM of pooled siRNAs (four separate siRNAs per transcript targeted) against ALK (catalog #M-003103-02), GAPDH (catalog #D-001140-01-20) negative control, non targeting negative control, or PLK1 (catalog #M-003290-01) positive control (siGENOME SMARTpool siRNA, Dharmacon, Lafayette, Colo.) using 0.1% v/v Dharmafect I, according to the manufacturer's protocol (Dharmacon, Lafayette, Colo.). The four separate ALK-directed siRNA sense direction sequences are:

```
                                        (SEQ ID NO: 1)
ALK J-003103-10 GGGCCUGUAUACCGGAUAAUU (SEQ ID NO: 2)
ALK J-003103-11 GUGCCAUGCUGCCAGUUAAUU (SEQ ID NO: 3)
ALK J-003103-12 CCGCUUUGCCGAUAGAAUAUU (SEQ ID NO: 4)
ALK J-003103-13 GGAGCCACCUACGUAUUUAUU
```

In brief, 35 µL of 1 µM siRNA and 35 µL of serum-free media were combined with 0.7 µL Dharmafect I in 70 µL of serum-free media and incubated for 20 minutes at room temperature, and then 560 µL of antibiotic-free complete media was added. The culture media was gently removed from the plated cells and replaced by 200 µL of fresh media containing the siRNA, mock or complete media. Cell growth was monitored continuously and recorded as a cell index (CI) every 30 minutes for a minimum of 96 hours. The "Cell Index" (CI) is derived from the change in electrical impedance as the living cells interact with the biocompatible microelectrode surface in the microplate well effectively measuring cell number, shape and adherence. Forty-eight hours after siRNA transfection, total RNA was extracted from the cells that had been plated in a parallel 96-well plate using the Qiagen (Valencia, Calif.) mini extraction kit, with DNAase treatment. Two hundred ng of total RNA was oligodT primed and reverse transcribed using Superscript II reverse transcriptase (Invitrogen, Carlsbad, Calif.). ALK, HPRT, GAPDH and PPIB expression levels were measured by quantitative RT-PCR using Taqman® gene expression assays (ABI, Foster City, Calif.), quantified on corresponding standard curves and normalized to the geometric mean of the three housekeeping genes. Two independent experiments were performed in triplicate. Growth inhibition of the neuroblastoma cell lines was determined by comparing the siRNA against ALK growth curve to that against GAPDH at the time of maximum cell index ($CI_{max}$): % growth inhibition=(1−$CI_{siALK}$/$CI_{siGAPDH}$)×100. ALK and GAPDH knockdown was determined by comparing the relative ALK expression: % knockdown=(1−$ALK_{siALK}$/$ALK_{siCONTROL}$)×100. The average % knockdown of ALK across all cell lines was 60% (range 21%-86%). The average % knockdown of GAPDH was 75% (range 61%-95%).

ALK Protein and Phosphoprotein Detection

Neuroblastoma cell lines were grown in T75 flasks under standard cell culturing conditions. For KELLY and SKNDZ lysates collected from the siRNA knockdown experiments, cells were plated in T25s, transfected with 10 nM siRNA (as above) and collected at 24, 48 and 72 hours after transfection. At 60-80% confluency (or the appropriate time point), the cells were collected, pelleted and washed twice with ice cold PBS. Whole cell lysates were extracted with 100 uL Cell Extraction buffer (Invitrogen FNN011) containing protease inhibitors (Sigma, P-2714) and PMSF, briefly sonicated and rotated for 1 hour at 4° C. After a 30 minute centrifugation at 4° C., the supernatant was removed and protein quantification was performed using the Bradford method. Lysates (50 ug for siRNA experiment and 100 ug for native cell lines) were separated on 4-12% Bis-Tris gradient gels and transferred to PVDF membranes. Membranes were then incubated and washed according to the Cell Signaling Western protocol with 1:1000 ALK (Cell Signalling, #3333) and Phospho-ALK (Cell Signalling, #3341) and 1:5000 actin (Santa Cruz, sc-2352).

Results

Identification of Germline ALK Mutations

To identify the location of a hereditary neuroblastoma predisposition gene, a genome-wide scan for linkage at ~6000 single nucleotide polymorphisms (SNPs) in 20 neuroblastoma families was performed. Because of the rarity of the condition, the genome-wide scan included pedigrees with varying degrees of confidence of actual heritability. Eight families had three or more affected individuals of close relation (high confidence), whereas 6 families consisted of only two individuals of first-degree relation (moderate confidence), and 6 families also only consisted of two affected individuals, but of more distant relationship (low confidence). A significant linkage signal at chromosome 2p was discovered with a maximum nonparametric LOD score of 4.23 at rs1344063 in 18 of the families (two excluded due to insufficient DNA). This refined a region previously reported for one of the pedigrees studied here (Longo et al. (2007) Hum. Hered., 63:205-11). By mapping informative recombination events, a predisposition locus was defined at chromosome bands 2p23-p24 delimited by SNPs rs1862110 and rs2008535 with 104 genes including the known neuroblastoma oncogene, MYCN (Schwab et al. (1984) Nature, 308:288-91; Weiss, et al. (1997) EMBO J., 16:2985-2995), and the ALK oncogene located 13.2 Mb centromeric. Despite previous work showing that forced overexpression of MYCN to the murine neural crest causes neuroblastoma (Weiss, et al. (1997) EMBO J., 16:2985-2995), resequencing of the MYCN coding region and 18 Kb of surrounding genomic DNA in probands from each linked family showed no disease-causal sequence variations.

The anaplastic lymphoma kinase gene (ALK) was subsequently studied because ALK had been previously identified as a potential oncogene in neuroblastoma through somatically acquired amplification of the genomic locus (Osajima-Hakomori et al. (2005) Am. J. Pathol., 167:213-22; George et al. (2007) PLoS ONE 2:e255). In addition, oncogenic fusion proteins leading to constitutive activation of the ALK kinase domain occur in many human cancers including anaplastic large cell lymphoma (Morris et al. (1994) Science, 263:1281-4), inflammatory myofibroblastic tumors (Griffin et al. (1999) Cancer Res., 59:2776-80), squamous cell carcinomas (Jazii et al. (2006) World J. Gastroenterol., 12:7104-12), and non-small cell lung cancers (Soda et al. (2007) Nature, 448:561-6; Rikova et al. (2007) Cell, 131:1190-203). ALK is a single chain receptor tyrosine kinase and a member of the insulin receptor superfamily. Expression is normally detected in developing central and peripheral nervous system. Further, ALK is an orphan receptor as its ligand is not known. The normal function of ALK is also not known. Indeed, a murine knockout shows no phenotype. Mutations within ALK have not been previously described as mechanism of oncogenicity.

Resequencing of the 29 ALK coding exons identified three separate single base substitutions within the ALK tyrosine kinase domain in eight of the probands screened (FIG. 1, Table 1). These DNA sequence alterations were not present in single nucleotide polymorphism (dbSNP; www.ncbi.nlm.nih.gov/projects/SNP/) or somatic mutation (COSMIC; www.sanger.ac.uk/genetics/CGP/cosmic/) databases, and were not detected in direct sequencing of the ALK tyrosine kinase domain in 218 normal control alleles. Each substitution was subsequently shown to segregate with the disease within each family (FIG. 1). The sequence variation in FNB12 (R1275Q) appears to have been acquired de novo in the affected father, and non-paternity was excluded by analysis of inheritance of genotypes within this pedigree. There are several asymptomatic obligate carriers identified (FNB2, FNB13, FNB32, FNB52, FNB56), suggesting that the incomplete penetrance of this disease may be due to lack of the acquisition of a second hit, or alternatively spontaneous regression following malignant transformation in at least a subset of cases. Notable is the very large multiplex family (FNB52) with discordance in twins and multiple unaffected carriers that segregates a unique germline mutation (G1128A).

TABLE 1

ALK mutations in neuroblastoma.

| Mutation | cDNA Variation | Type/Frequency | Region[1] | Probability Activating Mutation[2] |
|---|---|---|---|---|
| G1128A | c.3383G > C | Germline (1/8) | P-Loop | 0.95 |
| R1192P | c.3575G > C | Germline (2/8) | β4 Strand | 0.96 |
| R1275Q | c.3824G > A | Germline (5/8) Somatic (8/24) | Activation Loop | 0.91 |
| D1091N | c.3271G > A | Somatic (1/24 | N-Terminal | 0.29 |
| M1166R | c.3497T > G | Somatic (1/24) | C-Helix | 0.79 |
| I1171N | c.3512T > A | Somatic (2/24) | C-Helix | 0.85 |
| F1174I | c.3520T > A | Somatic (1/24) | End of C-Helix | 0.92 |
| F1174L | c.3522C > A | Somatic (8/24) | End of C-Helix | 0.96 |
| F1245C | c.3734T > G | Somatic (1/24) | Catalytic Loop | 0.94 |
| F1245V | c.3733T > G | Somatic (1/24) | Catalytic Loop | 0.91 |
| I1250T | c.3749T > C | Somatic (1/24) | Catalytic Loop | 0.87 |

[1]The region in which the codon alteration occurs is indicated. Note that the D1091N is immediately adjacent to the tyrosine kinase domain.
[2]The probability that the amino acid alteration results in oncogenic activation based on the methods of Torkamani and Schork (Torkamani et al. (2007) Bioinformatics, 23: 2918-25).

An exemplary full-length ALK sequence is provided in GenBank Accession No. NM_004304.3 (FIG. 9), although variants (e.g., natural allelic variants) of the ALK sequence are also encompassed by the instant invention.

ALK sequence variations occurred only in the families with high or moderate degrees of confidence for harboring a predisposing allele. Six of the eight families with three or more affected individuals had ALK missense alterations. The two families that did not have ALK sequence alterations identified were each shown to harbor mutations in the sympathicoadrenal lineage specific PHOX2B neurodevelopmental gene (Mosse et al. (2004) Am. J. Hum. Genet., 75:727-30; Raabe et al. (2008) Oncogene 27:469-76). Two of the six families consisting of only two affected individuals, but of first-degree relation, had ALK sequence variations. Each of these families carried the R1275Q alteration, and in FNB12 it is shown that the mutation arose de novo in the affected father, whereas in FNB56 the alteration was inherited from an unaffected father (FIG. 1). None of the six families with two distant relations affected with neuroblastoma showed ALK alterations, suggesting that the occurrence of an additional case of this relatively rare disease in an extended family member was likely a chance occurrence. Since there are several families who share identical mutations, it was determined if these families shared a common haplotype around the ALK gene and showed that the affected individuals with the same mutations did not share haplotypes, arguing against a founder effect.

Because ALK functions as an oncogene in other human cancers, it was predicted that the sequence variations discovered in the neuroblastoma pedigrees would result in constitutive activation. Therefore, a support vector machine-based statistical classifier was used to map the putative mutations and determine the probability that they would act as drivers of an oncogenic process (Torkamani et al. (2007) Bioinformatics, 23:2918-25; Torkamani et al. (2008) Cancer Res., 68:1675-82). Each of the germline alterations occurred at regions of the ALK kinase domain that have been shown to be major targets for cancer driver mutations in other oncogenic kinases (Table 1, FIG. 2). The R1275Q mutation was present in the germline DNA of affected individuals from five pedigrees (FIG. 1), and falls within the kinase activation loop in a region strongly associated with activating mutations in many different protein kinases, such as BRAF (Ikenoue et al. (2003) Cancer Res., 63:8132-7). This amino acid substitution results in an electropositive residue being replaced by a more electronegative one, possibly mimicking activating phosphorylation events. The R1192P mutation occurred at the beginning of the β4 strand of the kinase domain, and although it is predicted to be a driver mutation with high confidence (Table 1) the mechanism for activation is not yet clear (Torkamani et al. (2008) Cancer Res., 68:1675-82). The G1128A was seen only in the large pedigree with affected individuals in a single generation. The variation falls at the third glycine of the glycine loop, and identical mutations of this glycine to alanine in BRAF have been shown to increase kinase activity (Ikenoue et al. (2004) Cancer Res., 64:3428-35).

Identification of Somatic ALK Mutations

Having shown that heritable mutations in the ALK tyrosine kinase domain are associated with a highly penetrant predisposition to develop neuroblastoma, it was determined if ALK activation might also be somatically acquired. A representative set of 491 sporadically occurring primary neuroblastoma samples acquired from children at the time of diagnosis was examined on a 550K SNP-based microarray to assess for genome-wide copy number alterations. A total of 112 cases (22.8%) showed unbalanced gain of a large genomic region at 2p including the ALK locus (partial trisomy), and an additional 16 cases (3.3%) showed high-level focal amplification of ALK (FIG. 3). Each of the high-level amplifications co-occurred with MYCN amplification and/or other regions at 2p, except one case with an ALK amplicon only. The presence of aberrant ALK copy number status (gain or amplification) was highly associated with an aggressive clinical phenotype such as metastasis at diagnosis (P<0.0001) and death from disease (P=0.0003).

Figure 2A:
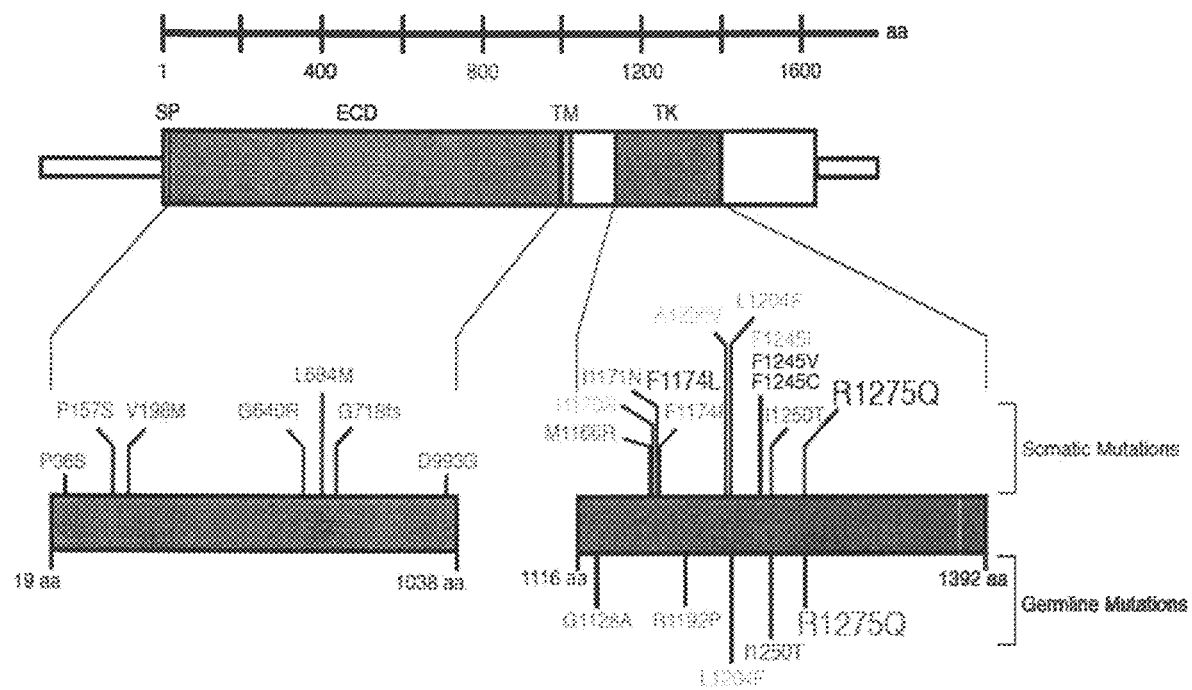
FIG. 2A provides a schematic diagram indicating protein structure of ALK, with mutations discovered in constitutional DNAs of familial cases (germline) and primary tumors from sporadic cases (somatic) indicated. All but one sequence alteration mapped to the tyrosine kinase domain (D1091N was just N-terminal and is not indicated here). Of the three germline mutations discovered, only the R1275Q was found in the tumor DNA samples. Conversely, the I1250T mutation discovered in the tumor set was also present in the matched germline DNA of that patient, while all of the other mutations studied here were somatically acquired.
Figure 2B:
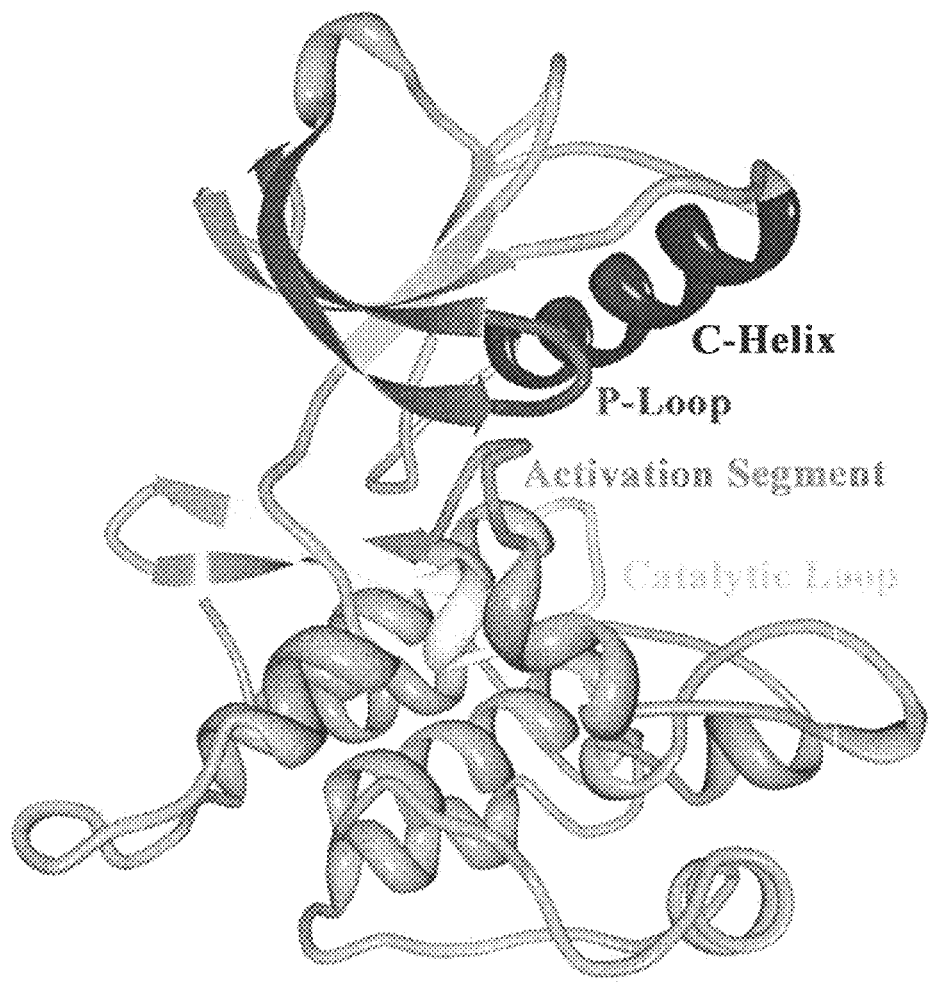
FIG. 2B provides a homology model of wild-type ALK with each major subdomain indicated (Torkamani et al. (2007) Bioinformatics, 23:2918-25; Torkamani et al. (2008) Cancer Res., 68:1675-82).
Figure 2C:
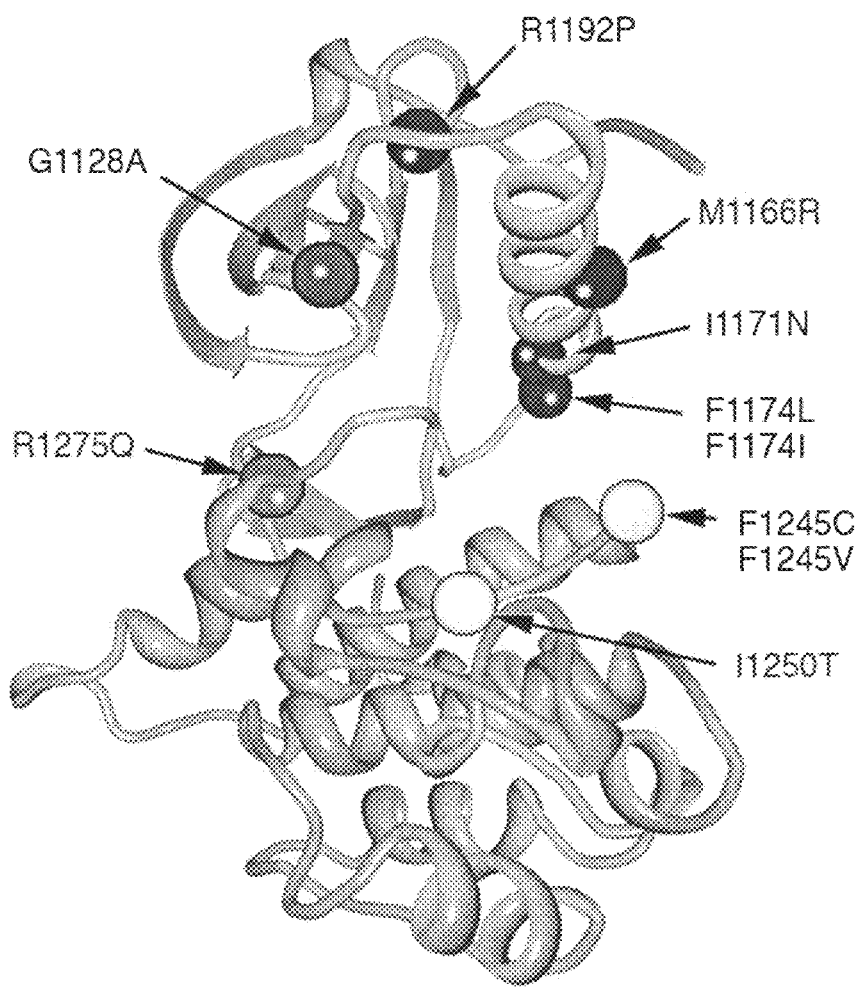
FIG. 2C shows ALK mutations mapped onto homology model (orientation different to show all mutations) with shades indicating subdomain in which the mutation resides (e.g. the R1275Q mutation falls within the activation segment).

Because of the association of ALK gain and amplification with high-risk disease features, a subset of 167 tumor samples from high-risk patients, and 27 human neuroblastoma-derived cell lines (all from high-risk patients), was examined for sequence alterations in the ALK tyrosine kinase domain. Fourteen of the 167 tumor (8.4%) and 10 out of 27 cell line (35.7%) samples showed single base substitutions consistent with activating mutations (FIG. 2). Eight separate single base substitutions were identified, with the R1275Q mutation being the only mutation also seen in the germline DNA of the families studied. Again, none of the sequence variations discovered here were in SNP databases or were identified in the resequencing of the ALK tyrosine kinase domain in 109 control subjects (218 alleles). Mutations were equally distributed between cases with and without MYCN amplification. Only one case had a co-occurrence of an ALK mutation (F1174L) and genomic amplification of the ALK locus, and in this case the mutated allele was amplified. Germline DNA was available for 9/14 patients with ALK mutations, and in one of these cases the sequence alteration (I1250T) was also present in the germline suggesting a hereditary predisposition that may or may not be de novo in this case.

Using the same statistical classifier employed for the germline mutations, it was shown that all but one of the sequence variations discovered in the tumor tissues were predicted to be activating mutations (Table 1), and the one that shows a low probability (D1091N) was outside of the core kinase domain. The vast majority of the somatically acquired mutations fell into either the catalytic loop or C-helix kinase domains, both frequent sites for oncogenic activating mutations (FIG. 2). Catalytic loop mutants, especially I1250T, may promote oncogenesis by altering substrate binding or, more likely, alter packing of the HRD and DFG motifs towards an activated conformation (Kannan et al. (2005) J. Mol. Biol., 351:956-72). The mutations observed in the ALK C-helix domain occurred at positions within the kinase domain previously observed to be mutated in other tumors. I1171N falls at an equivalent weakly oncogenic position in MET (M1149T) (Jeffers et al. (1997) Proc. Natl. Acad. Sci., 94:11445-50), and the M1166R, F1174I and F1174L mutants fall at equivalent positions mutated in ErbB2 (D769, V777) and EGFR (D761, V769) (Balak et al. (2006) Clin. Cancer Res., 12:6494-501; Lee et al. (2006) Cancer Lett., 237:89-94; Lee et al. (2006) Clin. Cancer Res., 12:57-61).

Functional Consequences of ALK Mutations

Figure 4A:
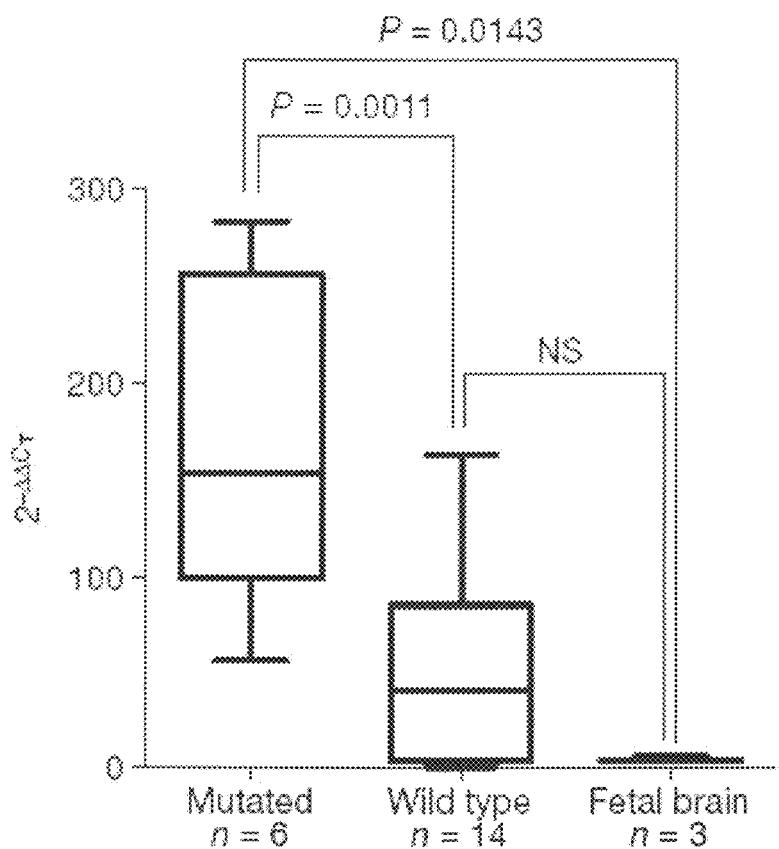
FIGS. 4A and 4B demonstrate that ALK is highly expressed and the kinase is phosphorylated in neuroblastoma cell lines harboring activating mutations.
Figure 4B:
Figure 5A:
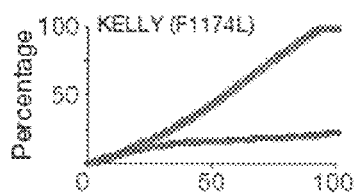
FIGS. 5A-5L demonstrate that ALK knockdown results in growth inhibition of ALK mutated or amplified neuroblastoma cell lines.
Figure 5B:
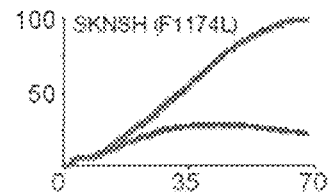
Figure 5C:
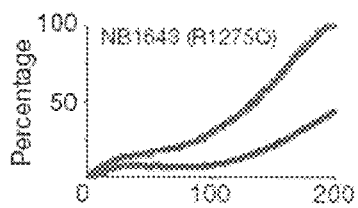
Figure 5D:
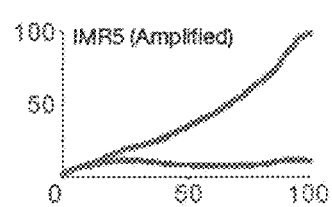
Figure 5E:
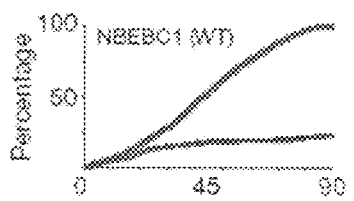
Figure 5F:
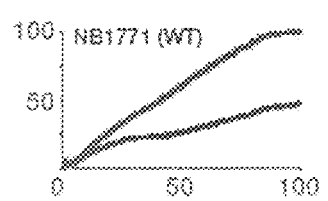
Figure 5G:
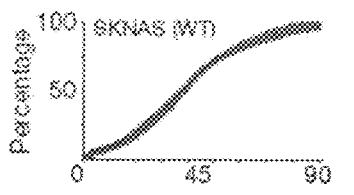
Figure 5H:
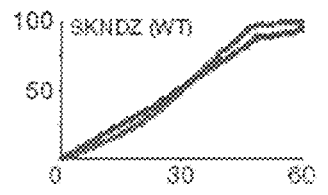
Figure 5I:
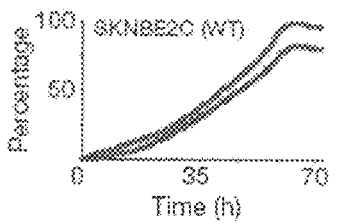
Figure 5J:
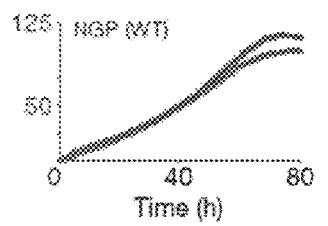
Figure 5K:
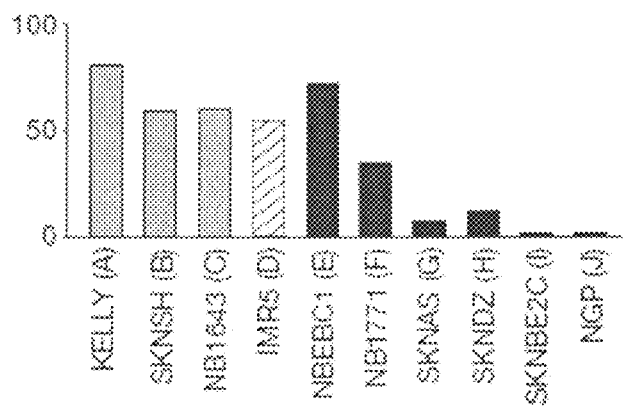
Figure 5L:
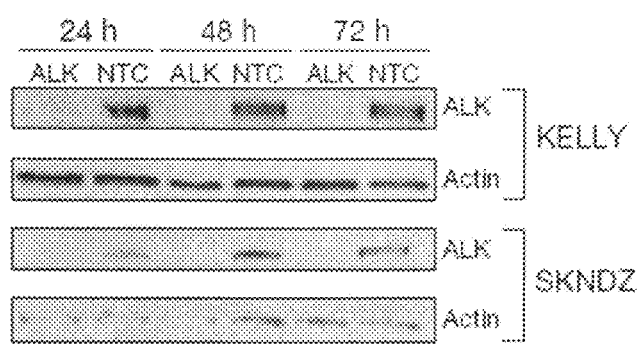

Various genes are differentially expressed in human primary neuroblastomas, with higher expression sometimes seen in the most aggressive subset of tumors (Wang et al. (2006) Cancer Res., 66:6050-62). It is shown herein ALK is highly expressed in all but one of 20 human neuroblastoma-derived cell lines using quantitative RT-PCR. ALK expression was higher in neuroblastoma cells compared to developing fetal brain, and cell lines harboring ALK mutations (N=6) expressed the mRNA at significantly higher copy number than ALK wild-type cell lines (N=14, FIG. 4A). Analysis of protein lysates from a panel of neuroblastoma cell lines showed constitutive phosphorylation of the tyrosine residue at codon 1604 in each of the cell lines harboring mutations, with weak phosphostaining in two wild-type cell lines (FIG. 4B).

To determine if ALK activation via mutation and/or amplification is functionally relevant in models of high-risk neuroblastoma, and thus be a tractable therapeutic target, the consequences of disrupting ALK signaling via knockdown of messenger RNA was examined. siRNAs directed against ALK (Dharmacon, Lafayette, Colo.) were transiently transfected into 10 neuroblastoma cell lines and screened for inhibition of substrate adherent growth. The knockdown of the mRNA and protein was demonstrated in all lines studied, but showed differential effect on cellular proliferation (FIGS. 5A-5L). Each of the cells harboring ALK mutation or amplification showed profound inhibition of proliferation to ALK knockdown. In addition, 2/6 of the ALK wild-type cell lines showed significant inhibition of growth with ALK knockdown and each of these had shown weak evidence for phosphorylation at tyrosine 1604 (FIG. 4b), suggesting an alternative mechanism may have resulted in ALK kinase activation in these two cell lines.

Currently, the frequency of ALK alterations in neuroblastoma are: mutations in the TK domain: ~10%, mutations in the extracellular domain: ~5%, and amplification: ~8%. p-ALK is detectable in 20/134 (15%) of NBL tissue samples.

Example 2

Figure 6A:
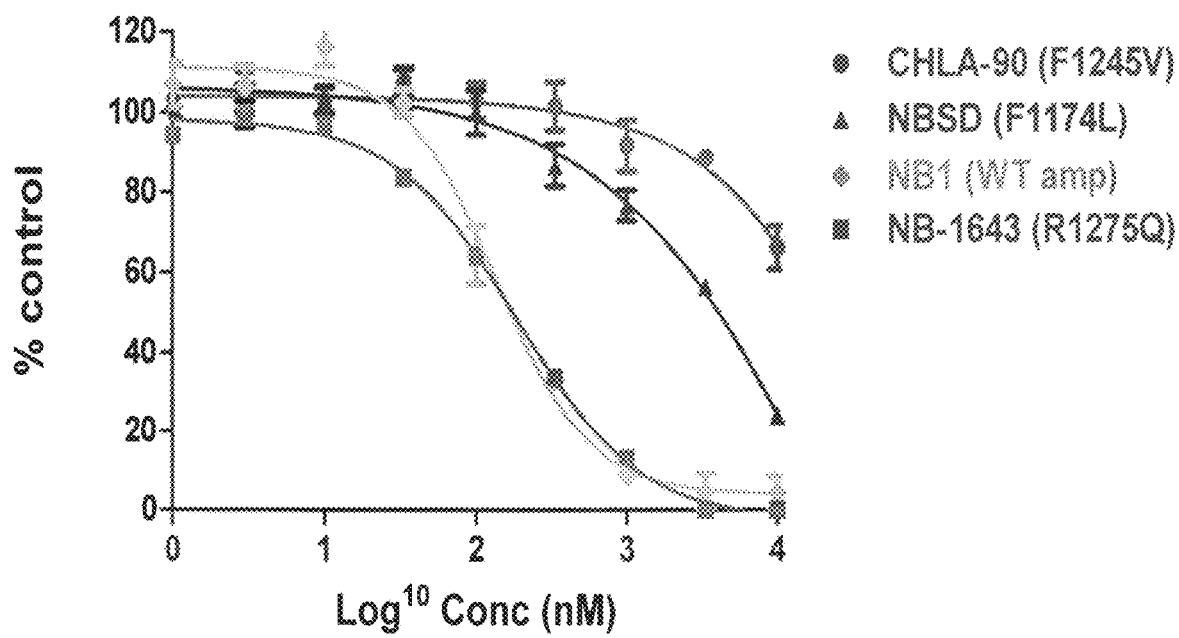
FIG. 6A is a graph of a dose response curve and FIG. 6B is a graph of the % growth inhibition with PF066 at 333 nM.
Figure 6B:
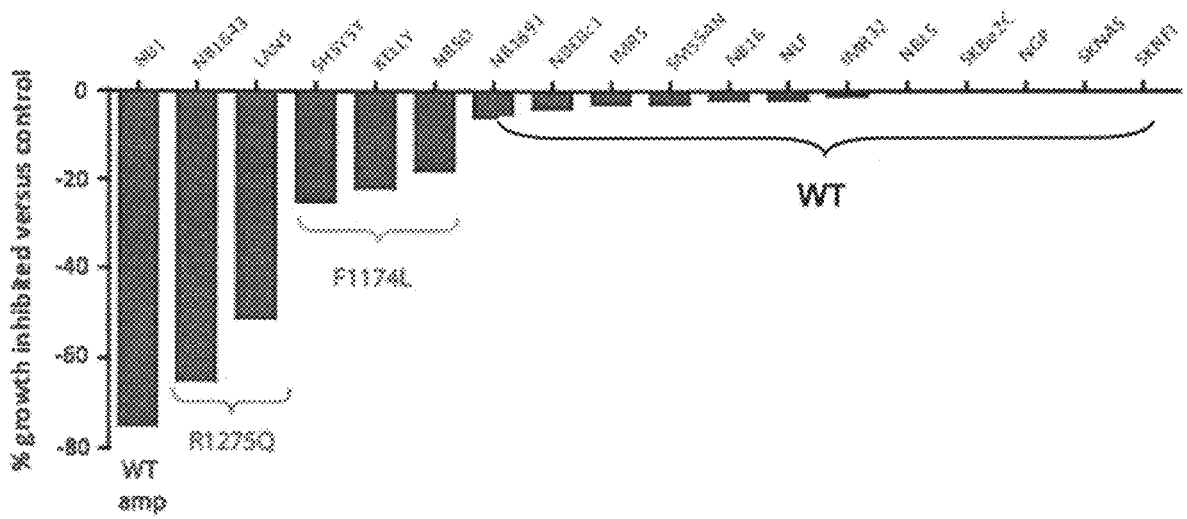
Figure 7:
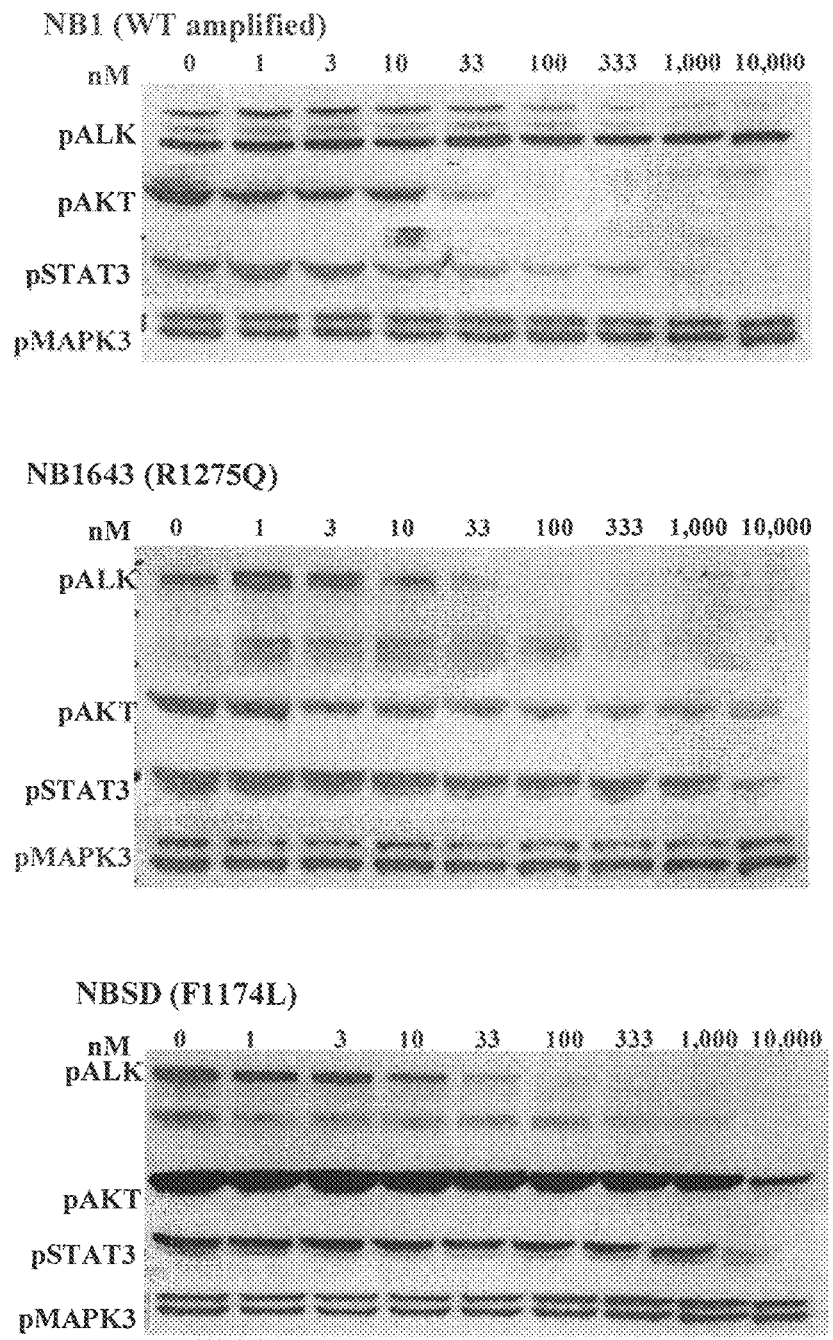
FIG. 7 shows the expression of pALK, pAKT, pSTAT3, and pMAPK3.

ALK is a tractable target for pharmacologic inhibition, but sensitivity depends on mutation type. FIG. 6A is a graph of a dose response curve and FIG. 6B is a graph of the % growth inhibition with PF066 at 333 nM. FIG. 7 shows the expression of pALK, pAKT, pSTAT3, and pMAPK3. For FIG. 6A, the human-derived neuroblastoma cell lines NB1643 (R1275Q), NB1 (ALK amplified), and NBSD (F1174L) were screened for evidence of anti-tumor activity to ALK inhibitor PF-02341066 in vitro. A quantitative assay to evaluate growth inhibition in a multi-well was used in a parallel format to screen for cellular cytotoxicity. Inhibition of substrate adherent growth during log-phase was then screened using the 96×6 RT-CES™ system (Real-Time Cell Electronic Sensing; ACEA Biosciences; San Diego, Calif.) with cells plated in triplicate for each assay, allowing for relatively high throughput and real-time assessment of alterations in growth kinetics, assaying for potential cytostatic or cytotoxic responses. The compound was studied at a minimum of 10 dose levels to determine the $IC_{50}$ values by concentration-response curves across a 4-log dose range. For FIG. 6B, the proliferation of neuroblastoma cell lines was measured after 72 hours of incubation with PF2341066 (333 nM) in DMSO using the RT-CES™ system. Cell lines displayed differential sensitivity depending on ALK status (p=0.01). Cell lines with ALK mutations and one cell line with amplification of wild type (WT) ALK were sensitive. R1275Q mutations were more sensitive than F1174L mutations. No cell lines with normal copy number WT ALK showed significant inhibition. Inhibition of growth %=100* (cell index vehicle−cell index treatment)/cell index control. For FIG. 7, the biochemical consequences of ALK activation and downstream signaling pathways were studied in ALK-mutant lines. These experiments quantify native and phosphorylated ALK, STAT3 and MAPK3 in ALK-mutated cell lines treated with PF-02341066.

Figure 8A:
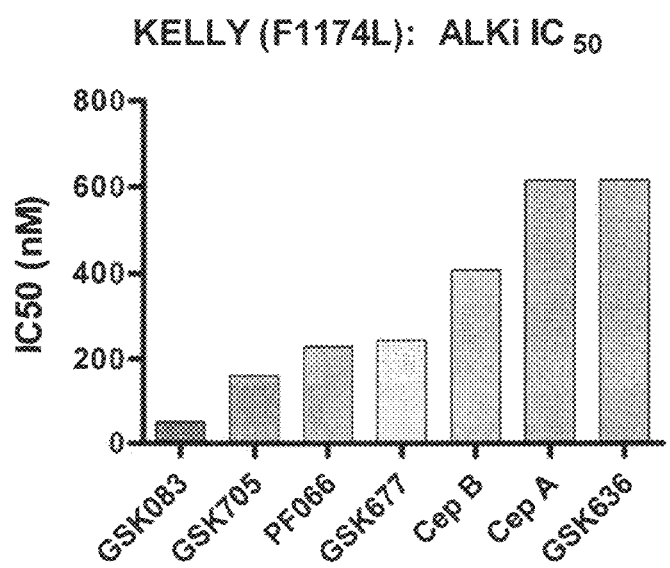
FIG. 8A provides the $IC_{50}$ of various drugs on the neuroblastoma cell line KELLY (F1147L).
Figure 8B:
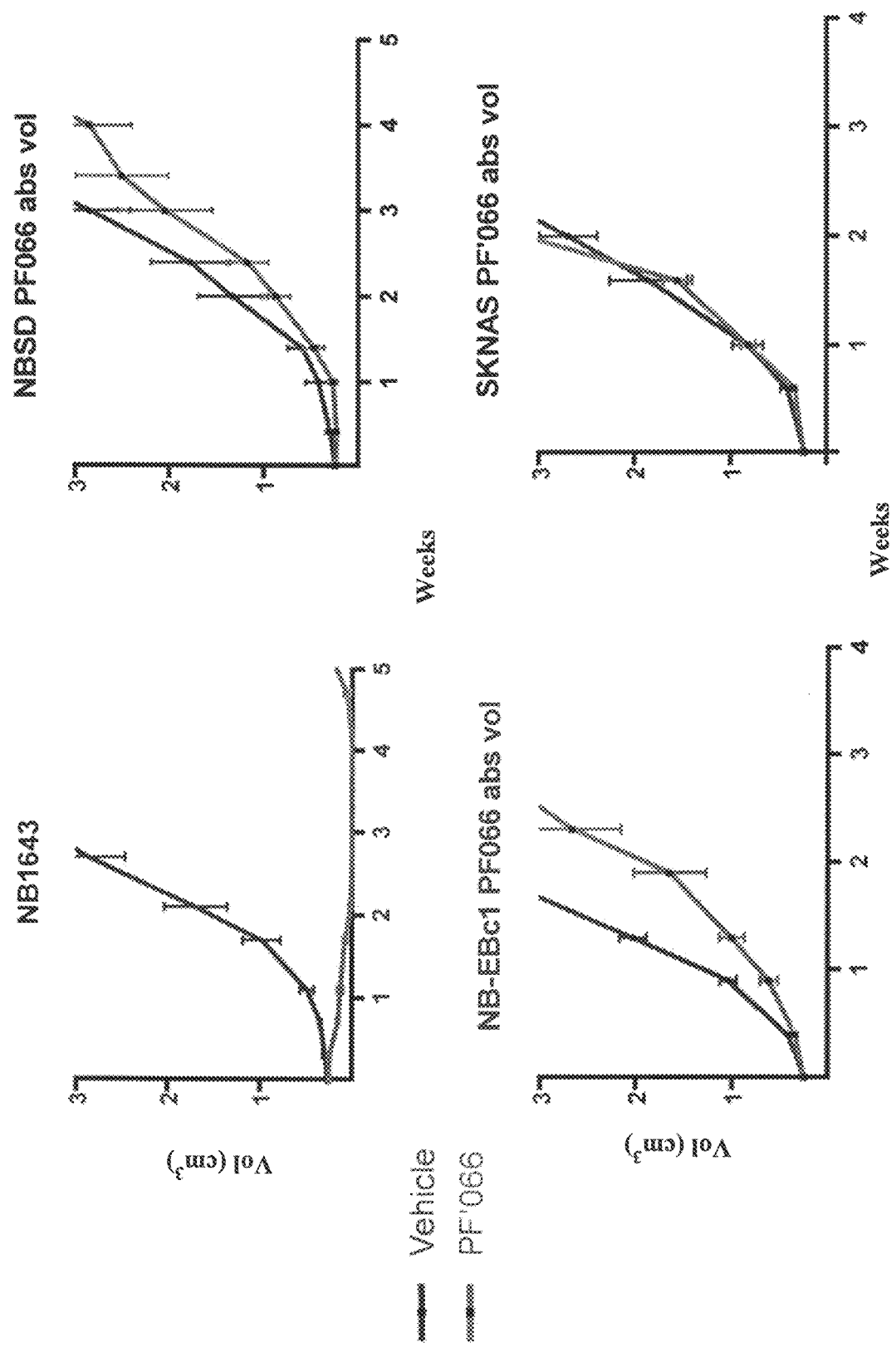
FIG. 8B provides graphs of tumor volume after weeks of administration of PF'066.

FIG. 8A provides the $IC_{50}$ of various drugs on the neuroblastoma cell line KELLY (F1147L). FIG. 8B provides graphs of tumor volume after weeks of administration of PF066. For FIG. 8A, the human-derived NB cell line KELLY was screened for evidence of anti-tumor activity to selective ALK inhibitors in vitro. A quantitative assay was used to evaluate growth inhibition in a multi-well parallel format to screen for cellular cytotoxicity. Inhibition of substrate adherent growth during log-phase was screened for using the 96×6 RT-CES™ system with cells plated in triplicate for each assay, allowing for relatively high throughput and real-time assessment of alterations in growth kinetics, assaying for potential cytostatic or cytotoxic responses. Each available compound was studied at a minimum of 10 dose levels to determine the $IC_{50}$ values by concentration-response curves across a 4-log dose range. For FIG. 8B, an intervention design and initiate therapy was used when tumors in mice are palpable at 200 mm³ as the starting volume. A total of 20 mice were randomized to treatment with an ALK inhibitor or vehicle, and serial measurements were performed using an electronic caliper system. Tumor volume is expressed as the mean tumor volume+/−standard error for groups of mice and tumor growth kinetics over time and progression free survival were compared.

ALK neuroblastoma mutants can be mapped onto the cMet-PF'1066 crystal structure. ALK R1275Q maps to c-Met R1227 which is not expected to destabilize the conformation of the activation loop residues important for binding PF-1066. ALK F1174L maps to c-Met F1124: This phenylalanine is highly conserved in ALK and sits in a hydrophobic pocket necessary for correctly positioning/ stabilizing the conformation of residues 1222-1228. Mutation of this residue is expected to significantly decrease PF-1066 binding. Accordingly, this modeling is consistent with the data provided in FIG. 8B.

Example 3

Neuroblastoma is a cancer of early childhood that arises from the developing autonomic nervous system. It is the most common malignancy diagnosed in the first year of life and shows a wide range of clinical phenotypes with some patients having tumors that regress spontaneously (D'Angio et al. (1971) Lancet 1:1046-1049), whereas the majority of patients have aggressive metastatic disease (Maris et al. (2007) Lancet 369:2106-2120). Neuroblastoma remains an important clinical problem as it continues to be a leading cause of childhood cancer mortality despite dramatic escalations in dose-intensive chemoradiotherapy, and long-term survivors experience significant treatment related morbidity (Oeffinger et al. (2006) N. Engl. J. Med., 355:1572-1582; Hobbie et al. (2008) Pediatr. Blood Cancer 51:679-683). To improve outcome and make paradigm-shifting advances in this disease, it is necessary to discover the key oncogenic drivers of the malignant process and exploit these therapeutically.

The anaplastic lymphoma kinase (ALK) oncogene is a receptor tyrosine kinase first identified after recurrent t(2;5) translocations in anaplastic large cell lymphoma (ALCL) were shown to fuse the amino terminus of nucleophosmin to a previously unidentified gene at 2p23 (Morris et al. (1994) Science 263:1281-1284). The ALK gene encodes a 1620-amino acid protein that undergoes post-translational N-linked glycosylation, and expression is restricted to the developing central and peripheral nervous system with a postulated role in regulation of neuronal differentiation (Iwahara et al. (1997) Oncogene 14:439-449). It has recently become clear that other human cancers in addition to ALCL activate ALK signaling through unique oncogenic fusions of the ALK gene with a variety of partners, including inflammatory myofibroblastic tumors (Griffin et al. (1999) Cancer Res., 59:2776-2780), squamous cell carcinomas (Jazii et al. (2006) World J. Gastroenterol., 12:7104-7112) and non-small-cell lung cancers (Soda et al. (2007) Nature 448:561-566; Rikova et al. (2007) Cell 131:1190-1203). A recent phase 1 trial of the dual MET/ALK kinase inhibitor PF-02341066 showed safety and significant anti-tumor activity in patients with refractory solid tumors harboring an ALK translocation (Kwak et al. (2009) J. Clin. Oncol., 27:15s (abstr 3509)).

Until recently, somatically acquired chromosomal translocation events were the only known mechanism for constitutively activating the ALK kinase. As explained herein, an unbiased linkage screen in familial neuroblastoma was performed and activating mutations in the tyrosine kinase domain of ALK were identified as the major cause of hereditary disease. Additionally, somatically acquired genomic amplification of ALK and mutations in the kinase domain as presumed oncogenic drivers in sporadic (nonfamilial) disease were also identified (see herein as well as Caren et al. (2008) Biochem. J., 416:153-9; Chen et al. (2008) Nature 455:971-974; George et al. (2008) Nature 455:975-978; Janoueix-Lerosey et al. (2008) Nature 455:

967-970). As explained herein, early data obtained with the discovery of oncogenic mutations in this gene indicated that siRNA and pharmacologic inhibition of ALK signaling in cells harboring a mutation resulted in cytotoxicity, further indicating that ALK mutation/amplification acts as a dominant oncogenic driver.

Key to impacting patient outcome with ALK-directed therapy was first to define the cohort of subjects who are most likely to benefit from ALK inhibition, and thus the prior mutation screen restricted to the "high-risk" subset was extended to cover all neuroblastoma phenotypic subsets. Second, preclinical experiments were performed to prove that the lead pharmacologic ALK-inhibitor showed antitumor activity directly due to on-target efficacy. The data presented here led directly to an ongoing pediatric Phase 1/2 trial of the PF-02341066 inhibitor that has shown safety and activity in ALK-activated adult solid malignancies.

Methods

Research Subjects and Samples

Neuroblastoma tumor samples were acquired from the Children's Oncology Group Neuroblastoma Tumor Bank. The Children's Hospital of Philadelphia Institutional Review Board approved this research.

DNA Sequencing

Bidirectional sequencing of the ALK coding sequence was performed by Agencourt Biosciences on tumor DNA from 593 sporadic neuroblastomas from the Children's Oncology Group (COG) tumor bank.

Tumor Copy Number Analysis

Tumor DNA from 591 sporadic neuroblastomas from the Children's Oncology Group (COG) tumor bank were assayed on the Illumina Infinium™ II HumanHap550 BeadChip as described above. DNA copy number for each individual tumor was estimated using OverUnder (Attiyeh et al. (2009) Genome Res., 19:276-83). Samples with a relative DNA copy number ≥4.5 over the entire ALK locus were considered amplified, whereas samples with a relative DNA copy number ≥2.3 were defined as having low-level gain of ALK. Tumors harboring low-level gain across ≥90% of chromosome 2 were defined as whole chromosome (WC) gains; all other gains were considered regional. To assess the statistical significance of recurrent regional gain/amplification on chromosome 2, the STAC algorithm (Diskin et al. (2006) Genome Res., 16:1149-1158) was applied using 1,000 random permutations of the regional gains identified in 591 primary tumors. Both the frequency and footprint statistics in STAC were evaluated, and an adjusted p-value ≤0.05 was considered statistically significant.

Tumor Quantitative mRNA Expression

Tumor RNA from 96 sporadic neuroblastomas from the Children's Oncology Group (COG) tumor bank was assayed on the Illumina Expression H6 v2.

Cell Line Quantitative mRNA Expression

Total RNA was isolated from cell lines according to QIAGEN's miRNeasy protocol. Real-time PCR using TaqMan® Gene Expression Assays was performed according to the manufacturer's instructions (Applied Biosystems). All primer/probe sets spanned exon boundaries to assure specificity for cDNA. Relative expression of anaplastic lymphoma kinase (ALK) was determined by normalization to the geomean of peptidyl-prolyl cis-trans isomerase B (PPIB) and hypoxanthine phosphoribosyl-transferase (HPRT1) using a standard curve method. All RTPCR experiments included a non-template control and were done in triplicate.

MET siRNA Knockdown in Neuroblastoma Cell Lines

This was performed in 4 cell lines using the 96-well RT-CES microelectronic cell sensor system as described above.

DNA Constructs and Retrovirus Production

Four sequence variants were introduced into the full-length ALK cDNA using site-directed mutagenesis (Origene Technologies, Rockville, Md.). All mutations and overall cDNA integrity were confirmed by sequencing of the entire ALK open reading frame. The mutant cDNAs, as well as NPM-ALK and wild-type ALK cDNAs, were cloned into the pCMV-XLS vector and subcloned into pIRES-EGFP. Infection of retinal pigment epithelial cells that express telomerase (HTERT-RPE1) was performed as follows: Phoenix™ Ampho cells (Oribigen-RVC-10001) were plated ~500,000 cells in a 6 well plate in DMEM media with 10% FBS, 1% Pen/Strep, Gentamicin. Twenty-four hours after plating (~50% confluent), Phoenix™ cells were transfected (Fugene) with retroviral vector MigR1 containing the ALK constructs following the Fugene® protocol (using 6:1 dilution of Fugene:plasmid DNA). HTERT-RPE1 cells were plated, ~500,000 cells per well of 6 well plate, and then harvested virus-containing media 48 hours post transfection. Media was removed from Phoenix™ cells and filtered through 0.45 µm syringe. Growth media on HTERT-RPE1 cells was replaced with virus cocktail (2 ml growth media, 1 ml filtered viral media, 4 µg/ml Polybrene® (Santa Cruz)) and incubated overnight. Viral media on HTERT-RPE1 cells was replaced on day 5 with fresh growth media and incubated ~48 hours. HTERT-RPE1 cells then sorted in cell sorter for GFP positive cells.

In Vitro Tumor Growth Inhibition

In vitro activity of PF-02341066 (Pfizer) dissolved in dimethyl sulfoxide (DMSO) was evaluated in 18 neuroblastoma cell lines using the RT-CES system (ACEA Biosciences, San Diego, Calif.) that measures electrical impedance of adherent cells, providing real-time quantification of cell proliferation. Cell lines were plated at a range of 5,000 to 30,000 cells per well depending on growth kinetics and drug was added 24 hours later across a 4-log dose range (1-10,000 nM) in triplicate. The IC50 was calculated from the cell index after 72 hours of incubation using a variable slope (Graph pad Prism Version 5.0). Growth inhibition at 333 nM PF-02341066 was calculated using the formula: % Inhibition=100*(Cell index control−cell index treatment)/Cell index control. Due to non-comparable maximum growth inhibition depending on ALK status, we analyzed growth inhibition at a single pharmacologically relevant dose. To verify cell line integrity, all lines were routinely genotyped (AmpFLSTR® Identifiler® kit; Applied Biosystems) and mycoplasma tested.

In Vitro Protein and Phosphoprotein Detection

Each neuroblastoma cell line was cultured in ten T75 flasks under standard cell culture conditions. At 70-80% confluence PF-02341066 was added to cell culture medium to achieve a designated final concentration at one of ten doses ranging from 0 nM to 10,000 nM. Cells were incubated for 2 hours with drug, then collected, pelleted, and washed twice with ice cold PBS. Whole cell lysates were then harvested, separated and immunoblotted as described herein. The following antibodies were used according to manufacturers' instructions: anti-ALK (1:1,000; Cell Signaling, 3333), anti-phospho-ALK Tyr 1604 (1:1,000, Cell Signaling, 3341), anti-STAT3 (1:1,000; Cell Signaling, 9132), antiphospho-STAT3 Tyr 705 (1:1,000; Cell Signaling, 9145), anti-AKT (1:1,000; Cell Signaling, 9272), anti-phospho-AKT Ser 473 (1:1,000; Invitrogen, 44-621G), anti-p44/42 MAPK (ERK1/2) (1:1,000; Cell Signaling, 4695), anti-phospho-p44/42 MAPK (ERK 1/2) (1:1,000; Cell Signaling, 9101), anti-actin (1:2,000; Santa Cruz, sc-1616).

In Vivo Tumor Growth Inhibition

CB17 scid female mice (Taconic Farms, N.Y.) were used to propagate subcutaneously implanted neuroblastoma tumors. Tumor diameters were measured twice per week using electronic calipers. Tumor volumes were calculated using the spheroid formula, $(\pi/6)*d^3$, where d represents the mean diameter. Once tumor volume exceeded 200 mm$^3$ mice were randomized (n=10 per arm) to receive PF-02341066 100 mg/kg/dose or vehicle (acidified water) daily by oral gavage for four weeks. Mice were maintained under the protocols and conditions approved by our institutional animal care and use committee. Mice were sacrificed when tumors were greater than 1500 mm$_3$.

In Vivo Protein and Phosphoprotein Detection

CB17 scid female mice (Taconic Farms, N.Y.) were used to propagate subcutaneously implanted NB1643 neuroblastoma tumors. Once tumor volume exceeded 300 mm$^3$ mice were randomized (n=3 per arm) to receive PF-02341066 100 mg/kg/dose or vehicle (acidified water) daily by oral gavage for 2 days. Mice were sacrificed 4 hours after the final dose to harvest xenografts, which were immediately snap frozen in liquid nitrogen. Frozen xenografts were pulverized and whole cell lysates were extracted using 100 μL extraction buffer (FNN011, Invitrogen) containing protease inhibitor (P-2714, Sigma), phosphatase inhibitors (P-5726, Sigma) and phenylmethyl sulphonyl fluoride. Lysates were sonicated, and rotated for 1 hour at 4° C. Following centrifugation at 4° C. for 30 minutes, the supernatant was removed, and protein quantification was performed using the Bradford method. Lysates (200 μg) were separated on 4%-12% Bis-Tris gradient gels and transferred to PVDF membranes which were immunoblotted according to manufacturers' instructions: anti-ALK (1:1,000; Cell Signaling, 3333), anti-phospho-ALK Tyr 1604 (1:1,000, Cell Signaling, 3341), and anti-actin (1:5,000; Santa Cruz, sc-2352).

Homology Modeling

The wild-type ALK sequence alignment to c-Met was performed in the PRIME suite within Maestro 8.5 (Schrödinger LLC, New York). Using the full-length ALK sequence and the sequence derived from the crystal structure of the kinase domain of c-Met with PF-02341066 (PDB entry=2WGJ), the sequences were aligned automatically followed by manual editing of gap areas. The final sequence alignment is shown in FIG. 15, where the F1174 and R1275 mutation sites are highlighted in gray. PRIME was then used to build a homology model of wild-type ALK with PF-02341066 bound using the c-Met/PF-02341066 crystal structure (2WGJ) as the template. ALK mutations were modeled as point mutations in the resulting wild-type ALK homology model.

Statistical Analysis

Associations of ALK mutation status and ALK amplification status with accepted neuroblastoma risk factors were tested using a Fisher's Exact Test (Table 2). Mixed-effects linear model was used to test tumor volume over time between treatment and vehicle groups controlling for tumor size at enrollment. The tumor size was transferred by logarithm before data analysis. Survival analysis was performed using the Log-Rank test with progression defined as tumor volume exceeding 1500 mm$^3$ or treatment related death. A P-value of 0.05 or less was considered to indicate statistical significance. All data analyses were conducted with the use of SAS.

Results

ALK Mutations are Restricted to the Tyrosine Kinase Domain and Occur in all Phenotypic Subsets Comprehensive re-sequencing of all 29 ALK coding exons and 500 base pairs of flanking sequence was performed in 188 high-risk diagnostic primary neuroblastoma tumors as part of the NBL-TARGET initiative (Neuroblastoma-Therapeutically Applicable Research to Generate Effective Treatments; target.cancer.gov/). The prior work presented the results from 167 of these samples restricted to the kinase domain only and it was sought to determine if non-kinase domain sequence alterations were putatively pathogenic. In the extracellular domain, seven nonsynonymous sequence variations were discovered and validated that were not reported in any of the SNP databases (Table 2). Only one of these was somatic (M770I), whereas five showed the same alteration in the germline DNA (one sample did not have matched germline DNA available). Five nonsynonymous sequence variations were found in the 3' untranslated portion of the gene, but 3/3 with matched germline DNA showed the same sequence variation in the constitutional DNA. Taken together, these data indicate that somatically acquired sequenced variations outside of the ALK tyrosine kinase domain are uncommon in neuroblastoma.

TABLE 2

| DNA sequence variation | Protein coding variation | Frequency | Number with alteration in germline DNA |
|---|---|---|---|
| A: Nonsynonomous sequence variations within the ALK tyrosine kinase domain (N = 594). | | | |
| c.3452C > T | T1151M | 1 (2%) | N/A |
| c.3497T > G | M1166R | 1 (2%) | 0/1 |
| c.3509T > G | I1170S | 1 (2%) | 0/1 |
| c.3512T > A | I1171N | 2 (5%) | 0/2 |
| c.3521T > G | F1174C | 1 (2%) | 0/1 |
| c.3520T > A | F1174I | 1 (2%) | 0/1 |
| c.3522C > A | F1174L | 7 (16%) | 0/4 |
| c.3586C > A | L1196M | 1 (2%) | N/A |
| c.3599C > T | A1200V | 1 (2%) | N/A |
| c.3610C > T | L1204F | 1 (2%) | 1/1 |
| c.3734T > G | F1245C | 2 (5%) | 0/1 |
| c.3733T > A | F1245I | 1 (2%) | 0/1 |
| c.3733T > G | F1245V | 2 (5%) | 0/2 |
| c.3749T > C | I1250T | 1 (2%) | 1/1 |
| c.3824G > A | R1275Q | 20 (47%) | 0/17 |
| B: Nonsynonomous sequence variations outside of the ALK tyrosine kinase domain (N = 167). | | | |
| c.106C > T | P36S | 1 (1%) | 1/1 |
| c.469C > T | P157S | 1 (1%) | N/A |
| c.592G > A | V198M | 1 (1%) | 1/1 |
| c.776G > A | R259H | 1 (1%) | 1/1 |
| c.1918G > A | G640R | 1 (1%) | 1/1 |
| c.2310G > T | M770I | 1 (1%) | 0/1 |
| c.2978A > G | D993G | 1 (1%) | 1/1 |
| c.3271G > A | D1091N | 1 (1%) | N/A |
| c.4219G > A | E1407K | 1 (1%) | 1/1 |
| c.4297_4299delGAG | E1433del | 1 (1%) | N/A |
| c.4390C > G | R1464G | 1 (1%) | N/A |
| c.4480G > A | G1494R | 1 (1%) | N/A |
| c.4657G > C | A1553P | 1 (1%) | 1/1 |

It was then sought to define the spectrum and frequency of somatic ALK mutations across all neuroblastoma phenotypic subsets. A representative set was identified of 594 primary neuroblastomas obtained at diagnosis for sequence analysis restricted to eight amplicons covering the entire tyrosine kinase domain. In total, non-synonymous sequence variations were identified in 7.2% of samples ($43/594$), which were grouped into four hotspots within the kinase domain (Table 2). All putative mutations in the ALK tyrosine kinase domain were not present in the single nucleotide polymorphism database (dbSNP; www.ncbi.nlm.nih.gov/projects/SNP/), and were not detected in direct sequencing of the ALK tyrosine kinase domain in 218 normal control alleles. The most prevalent mutation resulted in an arginine to glutamine substitution at amino acid position 1275 (R1275Q) and occurred in 20/43 tumors with mutations (47%). This was also the most common germline mutation discovered in hereditary neuroblastoma pedigrees, but was acquired in all 17 sporadic cases here where matched germline DNA was available. The second most common mutation resulted in a phenylalanine to leucine substitution at amino acid position 1174 (F1174L), occurring in 7/43 tumors harboring any sequence variation. In addition, the 1174 phenylalanine codon was mutated to isoleucine or cysteine in one case each, so that this codon was altered in 21% of tumors with a tyrosine kinase mutation. Of the 43 kinase domain mutations discovered in tumor tissues, constitutional DNA was available for 32 patients, and the majority were somatically acquired with 6.3% of cases (2/32) showing the same alteration in the germline (L1204F and I1250T; Table 2).

Figure 10A:
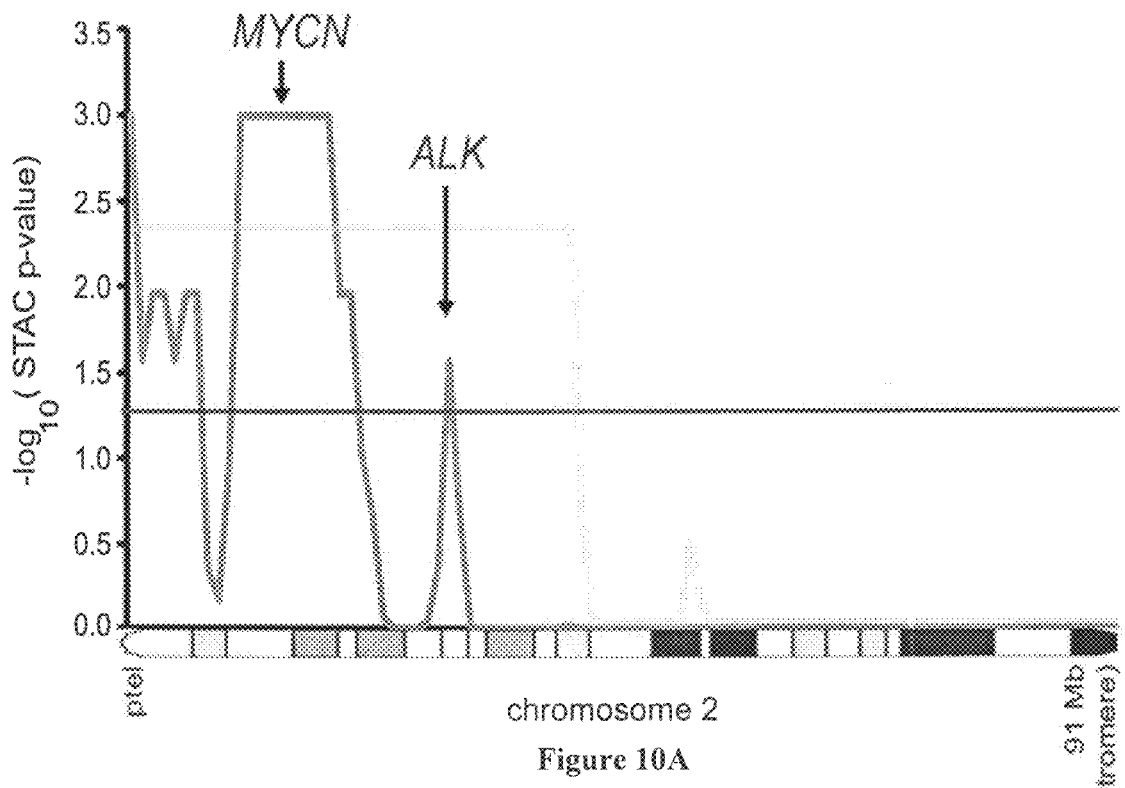
FIGS. 10A and 10B demonstrate that a gain of ALK locus correlates with increased mRNA expression. The significance of recurrent regional gain/amplification on the p-arm of chromosome 2 for 591 tumors was assessed using the Significance Testing for Aberrant Copy (STAC) algorithm (FIG. 10A). Significance is plotted as −log 10 (P-value) in 1-Mb windows along the p-arm of chromosome 2. Flat line marks threshold for statistical significance (adjusted P<=0.05). Frequency statistic (dark line) reveals significant recurrent focal amplification of both MYCN (P<0.001) and ALK (P=0.026). Footprint statistic (light line) reveals large 41-Mb region of recurrent low-level gain encompassing both MYCN and ALK (P=0.004).
Figure 10B:
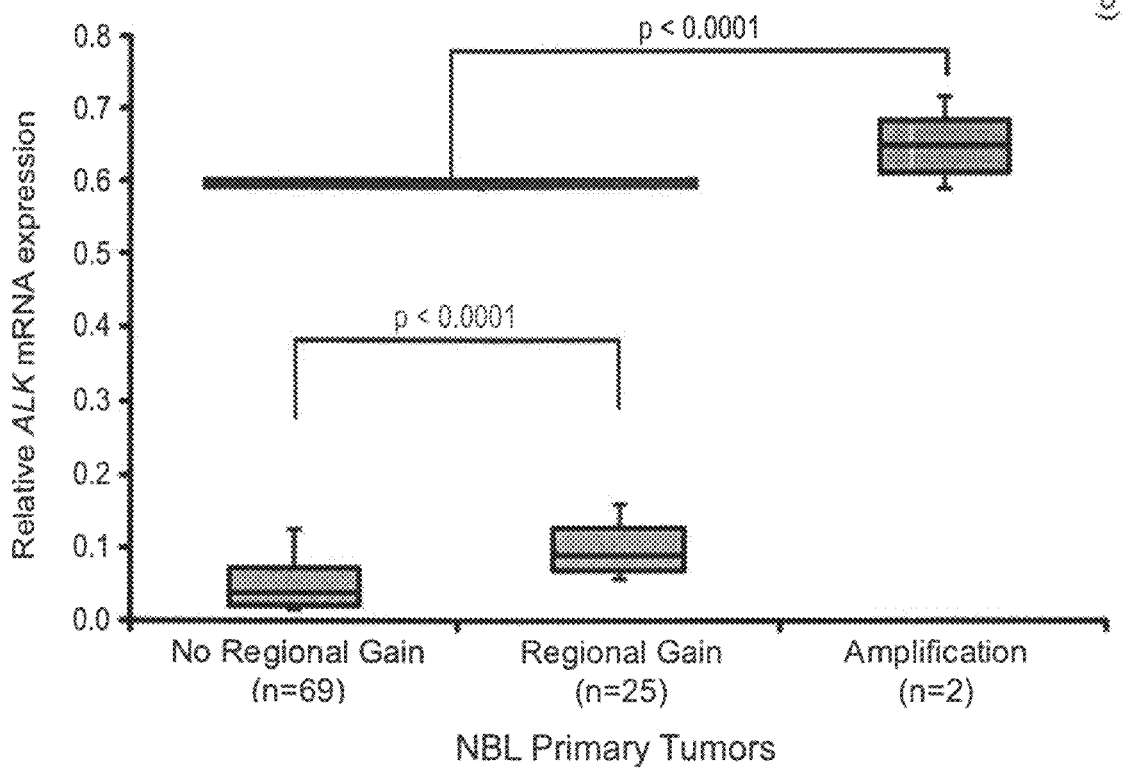

ALK Amplification and Regional Gain of the ALK Locus are Associated with Increased ALK Expression To define ALK allelic status, an overlapping set of 591 primary neuroblastoma tumors was characterized on the Illumina Human Hap550K SNP microarray. High-level amplification of ALK was detected in 2.4% of tumors (Table 3), defined as copy number >4.5 of the entire ALK gene relative to the chromosome 2 copy-number. Additional tumor DNA was available for 10 of these cases, and none showed an ALK mutation suggesting that mutation and gene amplification may be mutually exclusive genomic events. All tumors with ALK amplification also harbored MYCN amplification, but intervening sequence between these two genes located 13 Mb apart often was not co-amplified (FIG. 10A). A subset of 96 of these tumors was also assayed using the Illumina Expression Human6 v2 microarray. ALK amplification was significantly associated with ALK over-expression (P<0.0001; FIG. 10B). In addition, regional gain of a 40 MB region containing both MYCN and ALK was also associated with a significant, but more modest, increase in ALK expression compared to both whole chromosome gain (P=0.008) and normal copy number (P<0.0001; FIG. 10B).

TABLE 3

Frequency of ALK mutation and amplification in diagnostic primary neuroblastomas.

| | | Mutation Status (N = 593) | | | Amplification Status (N = 591) | | |
|---|---|---|---|---|---|---|---|
| | All Patients | Mutation+ | Mutation− | P-value* | Amplification+ | Amplification− | P-value* |
| All Patients | 867 | 43 (7%) | 550 (93%) | | 14 | 577 | |
| Age | | | | 0.6871 | | | 0.6036 |
| <365 days | 283 (33%) | 15 (35%) | 179 (33%) | | 4 (29%) | 169 (29%) | |
| >365 days | 580 (67%) | 28 (65%) | 370 (67%) | | 10 (71%) | 405 971%) | |
| Unknown | 4 | 0 | 1 | | 0 | 3 | |
| INSS Tumor Stage | | | | 0.2541 | | | 0.0786 |
| 1 | 171 (20%) | 7 (16%) | 138 (25%) | | 0 (0%) | 75 (13%) | |
| 2 | 119 (14%) | 8 (19%) | 79 (14%) | | 0 (0%) | 48 (8%) | |
| 3 | 123 (14%) | 6 (14%) | 80 (15%) | | 2 (14%) | 85 (15%) | |
| 4 | 390 (45%) | 20 (47%) | 220 (40%) | | 11 (79%) | 321 (56%) | |
| 4S | 56 (7%) | 2 (4%) | 31 (6%) | | 1 (7%) | 42 (8%) | |
| Unknown | 8 | 0 | 2 | | 0 | 6 | |
| MYCN Status | | | | 0.2452 | | | <0.0001 |
| Not Amplified | 710 (83%) | 33 (79%) | 456 (84%) | | 2 (14%) | 459 (81%) | |
| Amplified | 143 (17%) | 9 (21%) | 88 (16%) | | 12 (86%) | 108 (19%) | |
| Unknown | 14 | 1 | 6 | | 0 | 10 | |
| Shimoda Histopathology | | | | 0.7606 | | | 0.0502 |
| Favorable | 398 (49%) | 22 (54%) | 254 (49%) | | 2 (15%) | 224 (41%) | |
| Unfavorable | 414 (51%) | 19 (46%) | 262 (51%) | | 11 (85%) | 318 (59%) | |
| Unknown | 55 | 2 | 34 | | 1 | 35 | |
| DNA ploidy | | | | 0.6653 | | | 0.0127 |
| Hyperdiploid | 517 (65%) | 28 (68%) | 355 (66%) | | 3 (27%) | 331 (65%) | |
| Diploid | 275 (35%) | 13 (32%) | 181 (34%) | | 8 (73%) | 176 (35%) | |
| Unknown | 75 | 2 | 14 | | 3 | 71 | |
| COG Risk Group | | | | 0.5217 | | | 0.0009 |
| Low | 327 (38%) | 17 (40%) | 237 (43%) | | 0 (0%) | 151 (26%) | |
| Intermediate | 124 (15%) | 7 (16%) | 72 (14%) | | 0 (0%) | 78 (14%) | |
| High | 406 (47%) | 19 (44%) | 237 (43%) | | 14 (100%) | 342 (60%) | |
| Unknown | 10 | 0 | 4 | | 0 | 6 | |

*p-values from Fisher's Exact Test.

ALK Mutations Occur in all Phenotypic Subsets, but Amplification is Restricted to the Most Aggressive Cases Neuroblastoma is a diverse neoplasm and can behave in either a very benign fashion, or an extremely malignant one, based on a variety of clinical and biological factors (Maris et al. (2007) Lancet 369:2106-2120). Three risk groups are defined, with low-, intermediate- and high-risk cases having cure rates of >97%, >90% and 40-50%, respectively (Maris et al. (2007) Lancet 369:2106-2120). These cure rates are achieved with no chemotherapy in the low-risk group, moderate dose intensity chemotherapy in the intermediate-risk patients, and highly intensive multimodal chemoradiotherapy for the high-risk patients. Prior published studies had focused on the ALK status in the high-risk group of patients, and here it was determined if ALK aberrations occurred in the more benign subset of cases as well. As shown in Table 3, ALK mutations occurred in all phenotypic subsets, including all disease stages and risk groups. Mutations were seen in the very benign state 1 low-risk tumors as well as Stage 4S cases, that show spontaneous complete regression without cytotoxic therapy (D'Angio et al. (1971) Lancet 1:1046-1049). In contrast, ALK amplification events were restricted to the high-risk group of patients only. Thus, the likelihood of an ALK aberration at diagnosis in diagnostic high-risk neuroblastic tissues, where novel therapeutic approaches are needed, is approximately 11.3%.

Figure 11A:
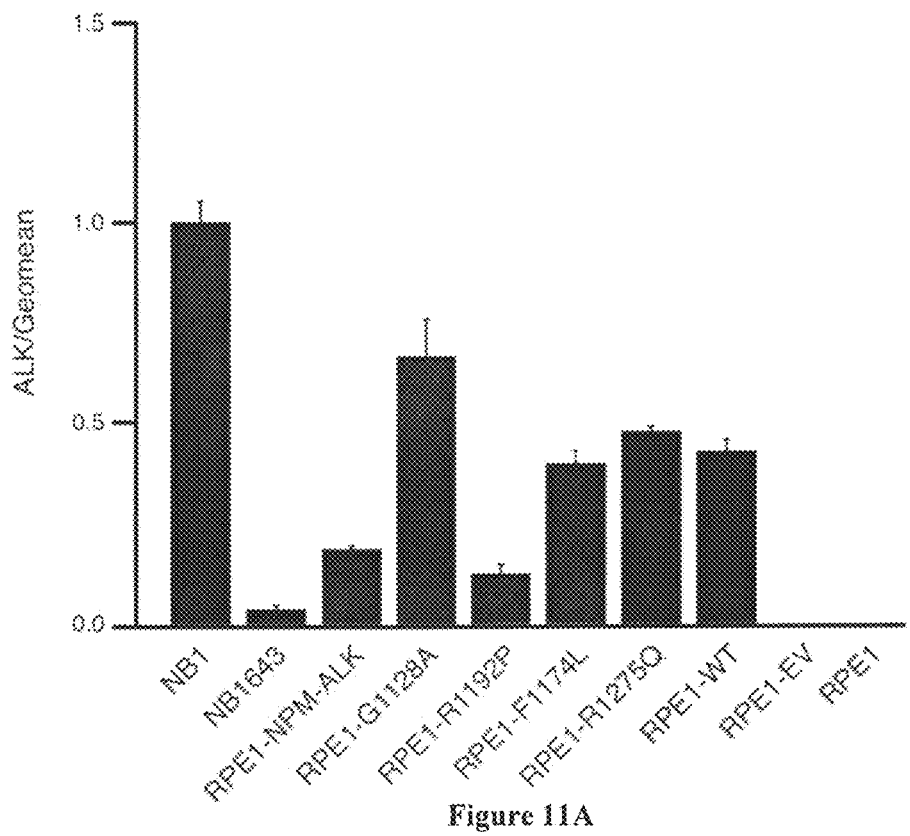
FIGS. 11A and 11B show mRNA expression and constitutive phosphorylation of ALK in RPE1 cells expressing activating ALK mutations.
Figure 11B:
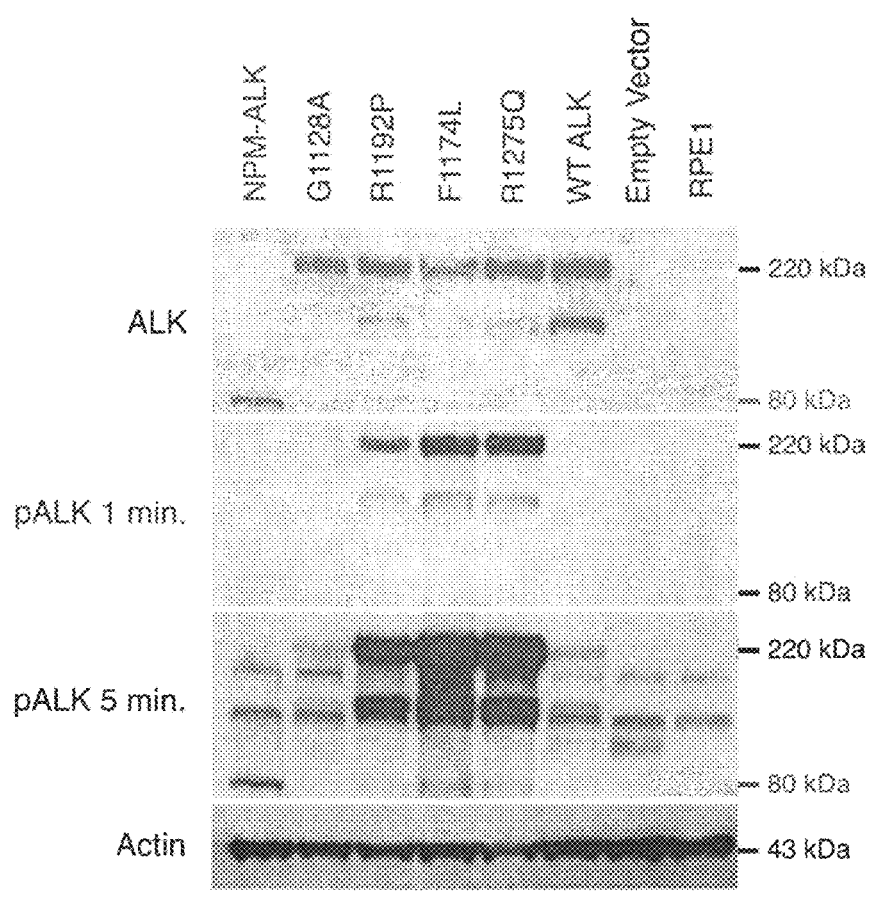

ALK R1275Q, R1192P, G1128A, and F1174L are Gain-of-Function Mutations that Induce Differential Constitutive Kinase Activation To determine the functional consequences of common germline and somatic mutations, human ALK cDNAs were engineered harboring the three most common germline mutations (R1275Q, R1192P, G1128A), and the F1174L mutation that was only seen in tumor tissue. Next these cDNAs, as well as NPM-ALK and wild-type ALK, were stably overexpressed in retinal pigment epithelial cells immortalized with telomerase reverse transcriptase (hTERT-RPE1) via retroviral infection. hTERT-RPE1 cells were chosen for these experiments because they are human neural crest-derived, as are neuroblastomas, and do not express detectable levels of ALK by quantitative RT-PCR. FIG. 11 shows that native ALK was expressed in all transfectants, but phosphorylation of the tyrosine 1604 residue, indicative of kinase activation, was clearly different based on mutation type. Cells over expressing the R1275Q and F1174L mutations, the two most common somatic mutations observed here, showed the most intense phosphostaining. Cells over expressing the G1128A mutant showed weak phosphostaining, only observable on prolonged exposure similar to forced overexpression of wild-type ALK. Without being bound by theory, this could provide an explanation, at least in part, for the observation that this germline mutation was unique to a previously reported large multiplex family that was notable for having multiple unaffected carriers, with the lowest tumor penetrance of all neuroblastoma families studied.

Figure 12:
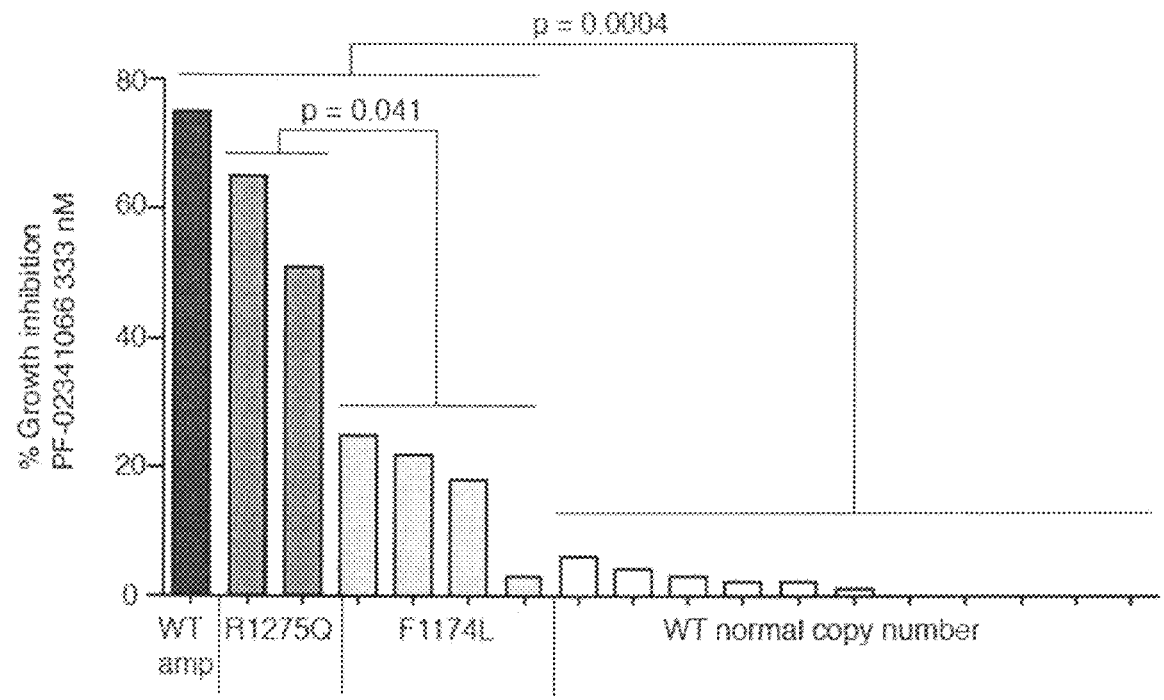
FIG. 12 shows the varying sensitivity of different ALK aberrations to ALK inhibition. Proliferation of neuroblastoma cell lines was measured over 72 hours of incubation with PF2341066, 333 nM in DMSO using the RT-CES system. Cell lines harboring ALK amplification or mutations were significantly more sensitive than cell lines with normal copy number, wild type ALK (p=0.0004). In addition, cell lines harboring the R1275Q mutation were significantly more sensitive than cell lines harboring F1174L mutations (P=0.041). Inhibition of growth %=100*(cell index vehicle-cell index treatment)/cell index control.

Cytotoxicity to Pharmacological ALK Inhibition In Vitro is Dependent Upon ALK Genomic Status It has been shown that mRNA knockdown of ALK in neuroblastoma cell lines with mutation or amplification is cytotoxic, and thus ALK inhibition might offer a tractable therapeutic target. In addition, it has been shown herein that pharmacologic inhibition of ALK kinase activity had an anti-proliferative effect in ALK mutated cell lines (see also Chen et al. (2008) Nature 455:971-974; George et al. (2008) Nature 455:975-978; Janoueix-Lerosey et al. (2008) Nature 455:967-970). In order to translate these findings to the clinic as quickly as possible, the sensitivity of neuroblastoma was determined in in vitro and in vivo models to PF-02341066, an ATP-competitive, orally bioavailable small molecule inhibitor of ALK and MET, that has shown safety in early phase clinical trials (Kwak et al. (2009) J. Clin. Oncol., 27:15s (abstr 3509)). A panel of eighteen human neuroblastoma-derived cell lines, chosen to be representative of ALK genomic status in primary tumors, was utilized to determine the $IC_{50}$ of PF-02341066 by concentration-response curves across a 4-log dose range (1-10,000 nM). Inhibition of substrate adherent growth was screened in a real-time electrical impedance monitoring system (Yu et al. (2006) Anal. Chem., 78:35-43; Atienza et al. (2006) J. Biomol. Screen 11:634-643). Cell lines harboring an ALK aberration (mutations or amplification) displayed significantly superior inhibition of growth than cell lines with wild-type ALK status (P=0.0004, FIG. 12). Cell lines harboring the R1275Q mutation or genomic amplification were more sensitive to this compound than those harboring F1174L mutations (P=0.041).

To demonstrate that cytotoxicity with PF-02341066 is mediated through ALK inhibition, it was shown that phospho-ALK correlated with ALK genomic status (FIG. 13), and that none of seven neuroblastoma cell lines studies, selected to be representative ALK genomic status, showed phospho-MET expression. Furthermore, siRNA knockdown of MET in a panel of 4 cell lines representative of ALK status showed no significant growth inhibition, as opposed to the significant inhibition seen with siRNA mediated ALK knockdown. Finally, it was shown that cytotoxicity was directly correlated with abrogation of phospho-ALK (see below, and FIG. 13).

Figure 13A:
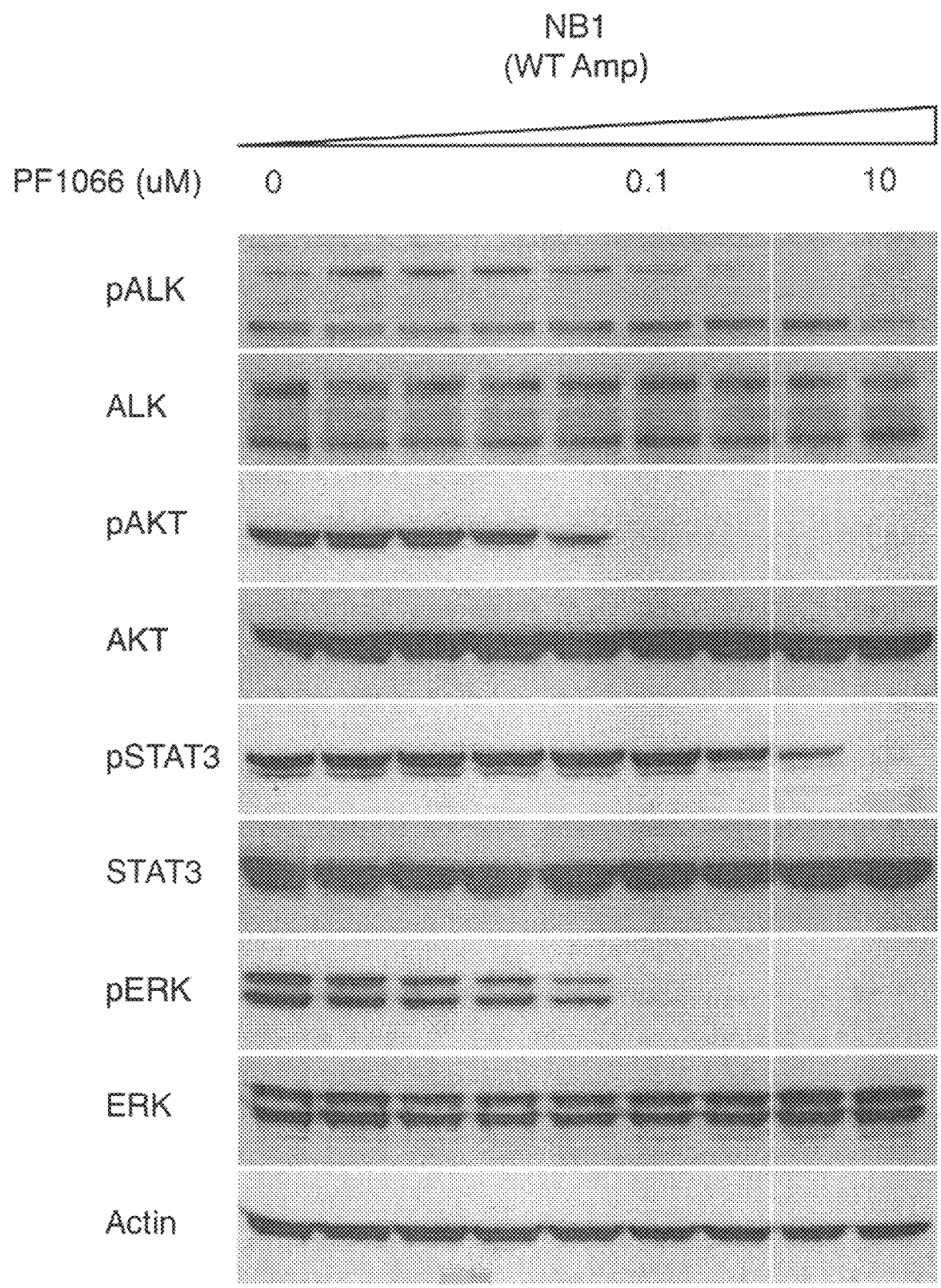
FIGS. 13A-13C show that in vitro growth inhibition is associated with abrogation of phosphorylation of ALK and downstream signaling proteins. Abrogation of phospho-ALK correlates to the dose where in vitro proliferation is first inhibited for all three-cell lines. NB1 (wild type amplified.
Figure 13B:
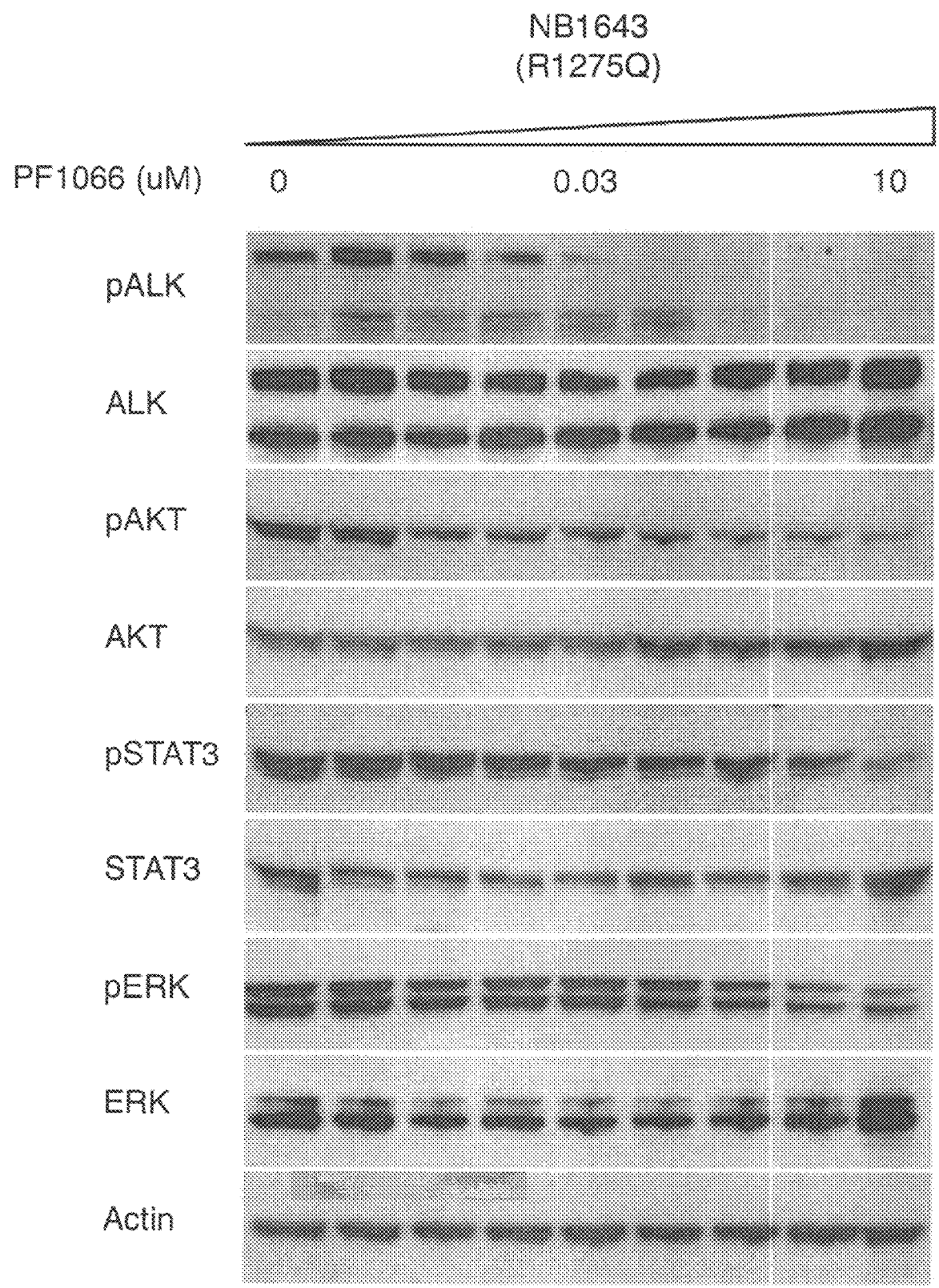
Figure 13C:
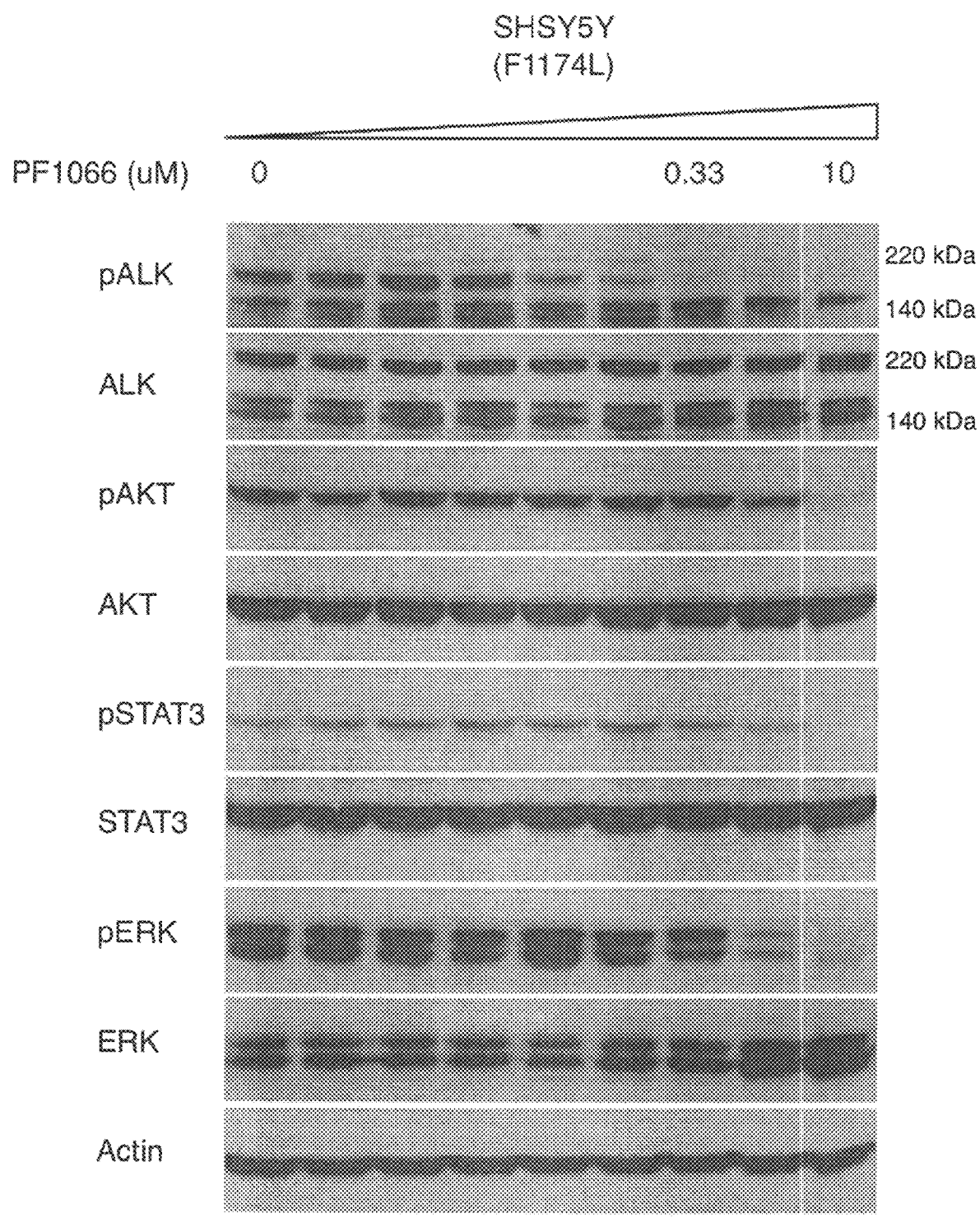

Cytotoxicity In Vitro Correlates with Abrogation of Phospho-ALK and Differential Inhibition of Downstream Signaling Pathways To correlate the phenotypic effect seen in vitro to degree of inhibition of constitutive kinase activation and to elucidate potential mechanisms underlying differential sensitivity to PF-02341066, dose dependent inhibition of phosphoprotein signaling was determined in three cell lines, selected to be representative of ALK genomic status observed in patient samples. The dose that first corresponded with inhibition of cell growth was correlated to abrogation of ALK tyr1604 phosphorylation in all three-cell lines (FIG. 13). Inhibition of proliferation and abrogation of phospho-ALK occurred in a dose-dependent manner in the 33-100 nM range in NB1 (WT amplification) and NB1643 (R1275Q), but did not occur in SH-SY5Y (F1174L) until 1000 nM, and these data were closely correlated to the in vitro cytotoxicity assay results. Taken together, these data indicate that the constitutive ALK activation via F1174L mutation may be more difficult to inhibit with PF-02341066.

In NB1 cells, abrogation of phospho-ALK occurred in parallel with abrogation of phosphoprotein signaling in pathways known to be important in lymphoma models of NPM-ALK mediated transformation: pSTAT3, pAKT, and pERK (FIG. 13). By contrast, in NB1643 cells, although the inhibition of proliferation at 33 nM correlated to abrogation of phospho-ALK, similar decreases in pSTAT3, pAKT, and pERK did not occur until higher micro molar doses (FIG. 13). Without being bound by theory, the occurrence of anti-tumor activity against NB1643 at doses well below those where pSTAT3, pAKT, and pERK were abrogated indicates this cell model may mediate ALK oncogenicity through alternative signaling pathways.

Pharmacologic Inhibition with PF-02341066 Shows Potent Anti-Tumor Activity In Vivo It was then determined if pharmacologic ALK inhibition resulted in anti-tumor activity in xenograft models of neuroblastoma. A pharmacologically relevant dose of PF-02341066 at 100 mg/kg/day for 4 weeks was tested against serially passaged human neuroblastoma xenografted in the flank of CB17 immunodeficient mice (Zou et al. (2007) Cancer Res., 67:4408-4417; Christensen et al. (2007) Mol. Cancer Ther., 6:3314-3322). PF-03241066 caused regression of all NB1643 xenografts (R1275Q) within three weeks, and complete regression was sustained over the fourth week of dosing (P<0.0001, FIG. 14A). On target activity was confirmed by demonstrating inhibition of ALK phosphorylation in NB1643 xenograft protein lysates harvested after 2 days of administration of PF-02341066 and 4 hours after last oral dose (FIG. 14A). Due to the range of in vitro sensitivity against cell lines harboring F1174L mutations, two such xenografts with differing sensitivity were tested. Treated SHSY5Y xenografts resulted in significant tumor growth delay (P<0.0001, FIG. 14B). In contrast, treatment of NBSD xenografts showed no statistically significant difference in tumor volume over time between treatment and control mice (P=0.3, FIG. 14C).

As cell line protein lysates and archival tumor specimens can demonstrate phospho-ALK staining in the absence of genomic ALK aberrations, in vivo activity of PF-02341066 was compared against two xenografts with diploid copy number and wild type ALK sequence but with differing levels of ALK expression and phospho-ALK activation. NB-EBc1 xenografts (previously shown to have weak phospho-ALK staining), treated with drug demonstrated significant tumor growth delay (p<0.0001, FIG. 14D). By contrast, SKNAS xenografts with absent ALK expression and no detectable phospho-ALK showed no tumor growth delay (P=0.87) and a non-significant difference in days to reach a tumor volume of 1.5 $cm^3$ (P=0.7) (FIG. 14E).

Homology Modeling Predicts a Structural Basis for Differential Activity Against R1275Q and F1174L Mutations A computational homology model of PF-02341066 bound to ALK was derived from the available co-crystal structure of PF-02341066 bound to the kinase domain of c-Met. Modeling was possible due to the high sequence homology of the kinase domains in the areas near the inhibitor-binding site. This model predicts that PF-02341066 binds very similarly to both ALK and c-Met, with nearly all of the major protein inhibitor interactions being conserved. In the PF-02341066 bound conformation of wild-type ALK, residues D1270 through Y1278 of the kinase activation loop form a bend. This bend creates one end of the inhibitor-binding site and positions the side chain of Y1278 to enable a key binding interaction with the fluorodichlorophenyl group of PF-02341066 (FIG. 15 A, B).

Figure 15A:
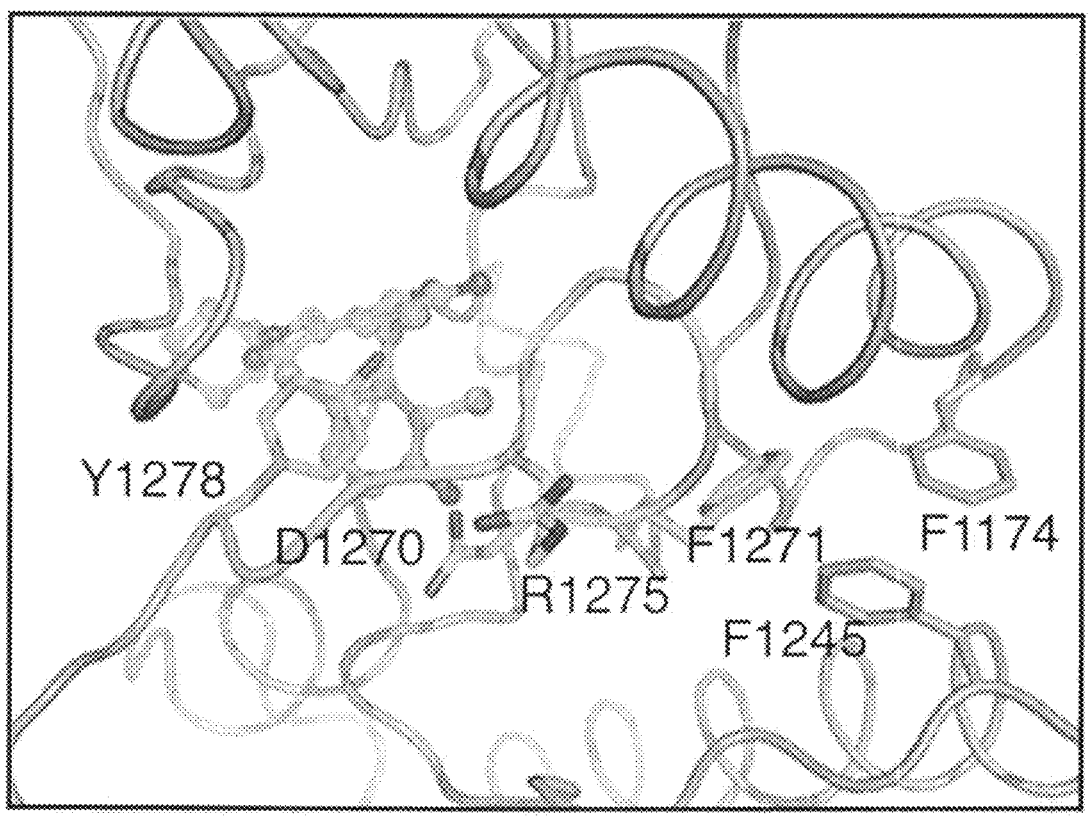
FIGS. 15A-15D show that homology modeling of ALK mutations predicts differential sensitivity to pharmacologic inhibition.
Figure 15B:
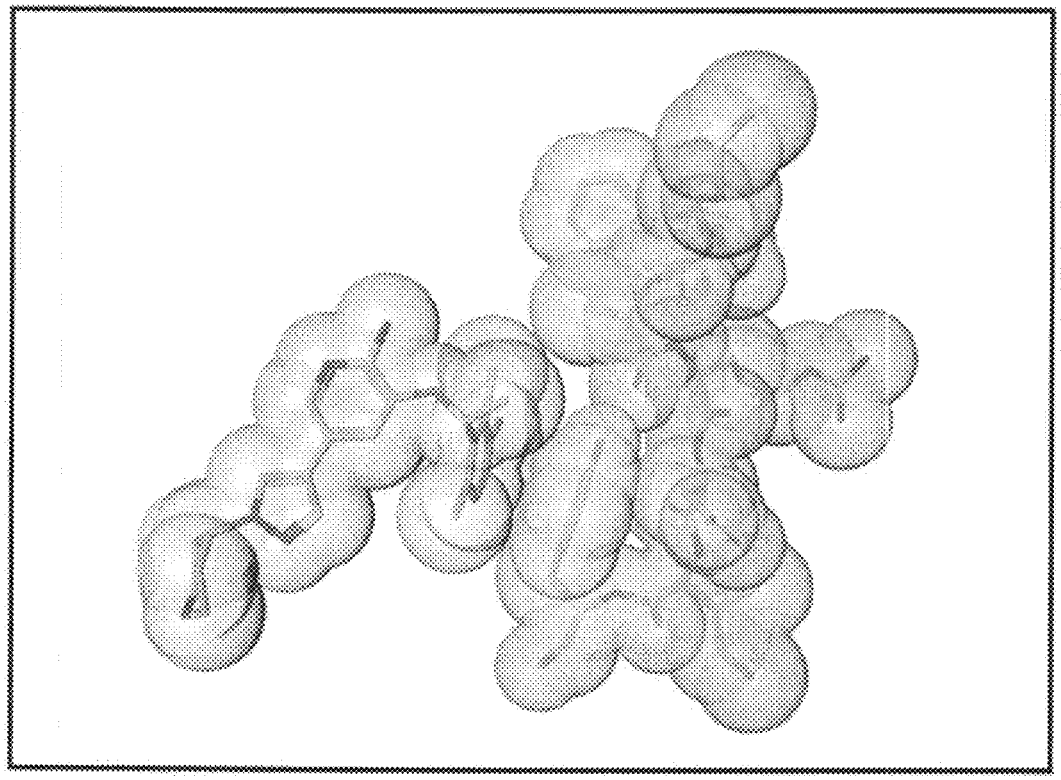
Figure 15C:
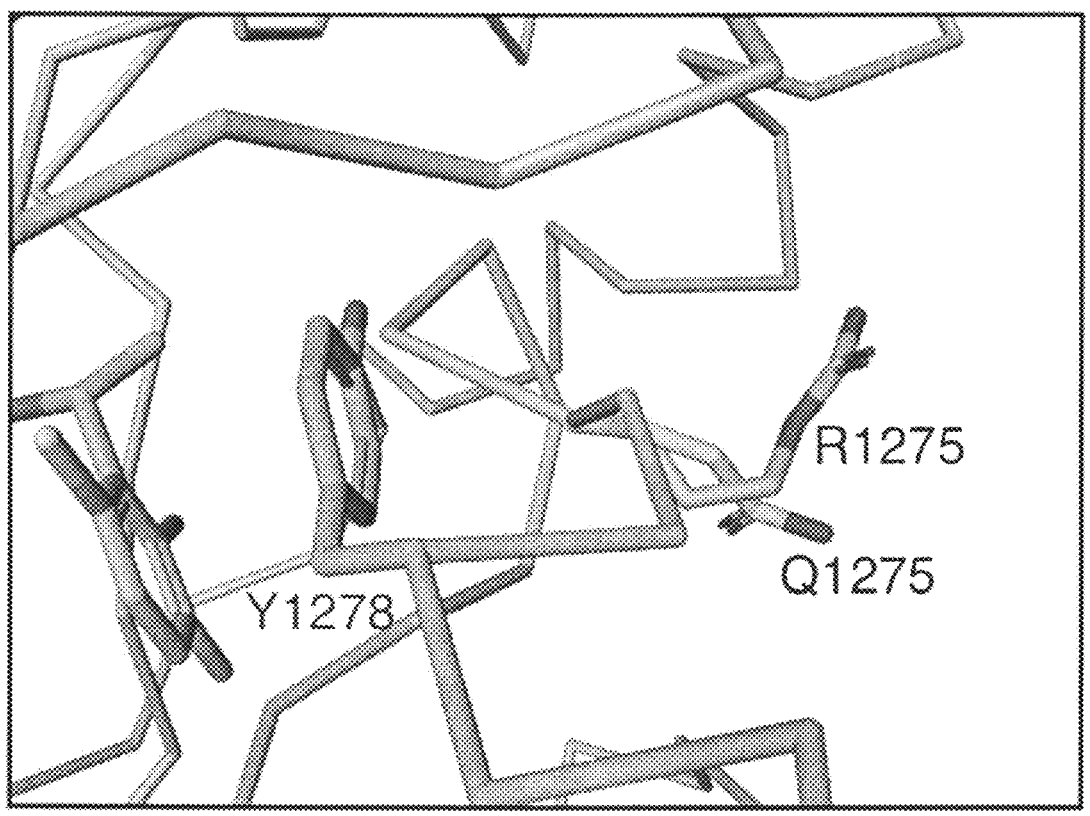

The ALK homology model predicts that a R1275Q mutant is likely to have the same PF-02341066 bound activation loop conformation as wild-type ALK and c-Met. The side chain of R1275 points out towards solvent and does not appear to make interactions critical for stabilizing the PF-02341066 bound activation loop conformation (FIG. 15C). Therefore substitution of arginine to glutamine is predicted to be accommodated on the protein surface, and is not predicted to result in an activation loop conformation that would significantly decrease key binding interactions with PF-02341066.

In contrast, the F1174L mutation is predicted to result in an activation loop conformation that significantly decreases binding of PF-02341066. The side chain of F1174 is situated in a cluster of three phenylalanines (F1174, F1245, and F1271) in attractive van der Waals contact with each other. The three phenylalanines appear to form an aromatic center that is part of a larger hydrophobic core. This hydrophobic core is likely important for stabilizing the particular activation loop conformation necessary to make key binding interactions with PF-02341066 (FIG. 15 A, D). One of the three phenylalanines in the hydrophobic core, F1271, is at the beginning of the activation loop and lies within a conserved DFG (Aspartic acid, Phenylalanine, Glycine) amino acid sequence. Conformational flipping of this conserved DFG sequences is known to effect large changes in activation loop conformations in many tyrosine kinases (Lu et al. (2009) Biochemistry 48:3600-3609; Hubbard, S. R. (2002) Front. Biosci., 7:d330-340; Han et al. (2009) J. Biol. Chem., 284:13193-13201).

Figure 15D:
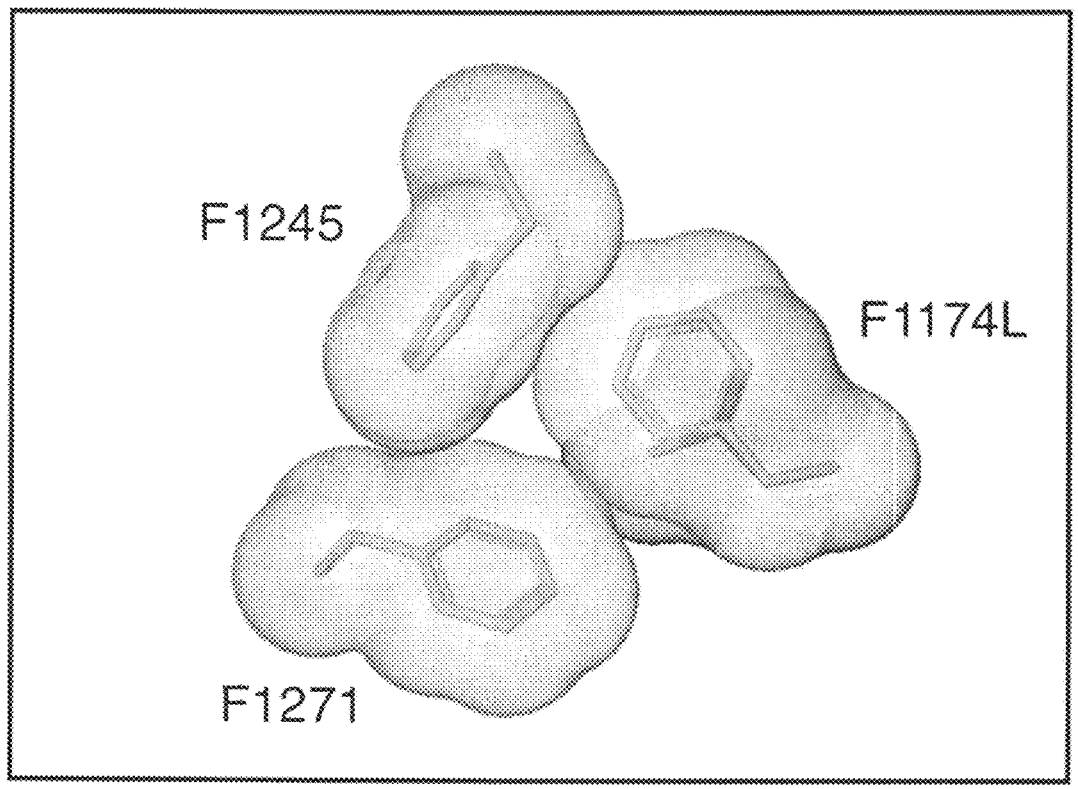

As shown in FIG. 15D, a F1174L mutation is predicted to result in a decrease in interactions within the aromatic center. This occurs because the smaller size and non-planarity of leucine compared to phenylalanine is predicted to result in a loss of contact with F1245. The loss of the F1174L-F1245 interaction and accommodation of the non-planar leucine likely destabilizes the aromatic center and hydrophobic core formed by the three phenylalanines in wild type ALK. Destabilization of the hydrophobic core could result in a flip of a flexible amino acid segment, D1270-F1271-G1272, resulting in a large positional change in the activation loop such that key binding interactions to PF-02341066 are lost and inhibitory activity is reduced.

The recent discovery of germline and somatic gain of function mutations in the receptor tyrosine kinase ALK provides a tractable therapeutic target for new drug development in neuroblastoma. Here, the frequency and spectrum of ALK gene mutations and amplification events was determined in a representative series of diagnostic primary neuroblastomas. The instant results demonstrate that ALK mutations are detected in 7% of cases and are found primarily in the tyrosine kinase domain. Other kinases such as EGFR (Lee et al. (2006) PLoS Med 3:e485), KIT (Gari et al. (1999) Br. J. Haematol., 105:894-900), and FLT3 (Frohling et al. (2007) Cancer Cell 12:501-513) show activating mutations in both the intra- and extra-cellular and juxta-membrane domains. Accordingly, it is clear that sequence alteration outside the kinase domain may be functionally relevant, but it is clear from the data presented herein that the majority of ALK mutations occur in the kinase domain.

High-level amplification of ALK was detected in another 2.4% of tumors, so that about 10% of neuroblastomas have genomic evidence for ALK activation at diagnosis. Unlike sequence variation mutations, high-level ALK amplification was restricted to the high-risk group of tumors with concomitant MYCN amplification. These data indicate that in the setting of genomic instability, ALK can be a target for amplification events that presumably lead to pathway activation due to homodimerization of overexpressed ALK protein. Notably, 19% of tumors show unbalanced gain of 2p including the ALK locus. Some of these are focal, suggesting a tandem duplication event targeting the ALK locus, but the majority of these are very large, often involving the majority of the short arm. The unbalanced gains in 2p may correlate with pathway activation and/or sensitivity to targeted interruption of ALK signaling.

The two most commonly observed mutations resulted in robust constitutive phosphorylation of the ALK kinase, whereas the rare germline mutation G1128A, which has not been observed somatically, resulted in only weak activation, similar to the amount seen with forced overexpression of wild-type protein. While these data are semiquantitative, the magnitude of difference is clear and consistent with the observation that heritable G1128A mutations resulted in low tumor penetrance, compared to the families with R1275Q germline mutations, each showing near complete tumor penetrance in at risk carriers. The hTERT-rRPE1 assay provides complimentary information to forced overexpression in other systems, such as BAF3 (George et al. (2008) Nature 455:975-978) or NIH-3T3 cells (Janoueix-Lerosey et al. (2008) Nature 455:967-970), but the instant system offers advantages for further functional analysis of mutations as they are discovered to determine their potential as an oncogenic driver in an appropriate cellular context. Cellular context is important and the use of this system to understand the functional consequences of all sequence variations identified may be used to dissect the oncogenic potency of the various mutations discovered.

The data clearly demonstrate that cytotoxicity to PF-02341066 is highly associated with ALK genomic status and evidence for constitutive activation. It is also evident that some neuroblastomas may somatically activate ALK signaling in the absence of mutation or amplification.

PF-02341066 has already demonstrated safety and tolerability in humans, as well as dramatic reductions in tumor volumes and disease stabilization for non-small cell lung cancers with activated ALK via translocation events. This drug is robustly cytotoxic in vitro and in vivo in cells with the most common mutation (R1275Q) and in wild-type cells with high-level ALK amplification (p<0.0004), and it is shown herein that this is not an effect of c-Met inhibition. F1174L models also show growth inhibition with PF-02341066, though not nearly as potently; and there are models without evidence for ALK mutation, but with constitutive activation that show growth inhibition, suggesting that several subsets of patients may benefit from ALK inhibition therapy. It is evident that phospho-ALK is an appropriate surrogate biomarker of response and that abrogation of phospho-ALK can be highly correlated with response to pharmacologic inhibition.

In NPM-ALK driven lymphoma models, it has been shown that several canonical signaling pathways are activated, including STAT3, AKT/PI3K, and RAS/ERK, thus influencing cell proliferation and survival (Zamo et al. (2002) Oncogene 21:1038-1047; Chiarle et al. (2005) Nat. Med., 11:623-629; Lim et al. (2009) Blood 114:1585-1595). However, the situation appears to be more complex in neuroblastoma. The NB1 model with wild type, amplified ALK, shows constitutive activation of each of these pathways, with dose-dependant abrogation of signaling paralleling diminution of phosphorylated ALK and cytotoxicity. However, the NB1643 cells harboring an R1275Q mutation are equally sensitive to PF-02341066, show the same pattern of diminution of phospho-ALK staining, but do not likewise abolish phosphorylated proteins in the STAT3, AKT/PI3K, and RAS/ERIC until much higher doses. SY5Y cells, which are relatively resistant to PF-02341066, also do not abolish STAT3, AKT/PI3K, and RAS/ERK signaling even at the higher dose levels where cytotoxicity (and diminished phosphorylated ALK) was seen. Without being bound by theory, these data—taken together—indicate that ALK mutations may exert their oncogenic effect through other pathways.

The data presented herein show that mutations in ALK are present across all neuroblastoma disease subsets, both benign and malignant forms, consistent with acquired ALK activation being an early event in tumorigenesis. ALK amplification, however, is strongly associated with the high-risk subset (P<0.001) and MYCN amplification (P<0.001), so that approximately 11% of all newly diagnosed high-risk neuroblastoma patients harbor genetic evidence for ALK activation and can be expected to potentially benefit from ALK inhibition therapy. In the instant dataset, mutations and amplifications of ALK are mutually exclusive, suggesting these modes of genomic dysregulation do not co-occur in sporadic neuroblastoma. Mutations in ALK are significantly more frequent in human neuroblastoma-derived cell lines. Without being bound by theory, this may occur through selection of rare clones that are present in diagnostic tissues and emerge during therapy, as has been shown in chronic myeloid leukemias harboring a BCR-ABL gene translocation, mutation or amplification (Gone et al. (2001) Science 293:876-880).

As the crystal structure for the ALK kinase domain has not been solved, in silico techniques were used to explore the observed differentially cytotoxicity of PF-02341066 against the two most common mutations observed in patient samples. Structural modeling predicted that the phenylalanine to leucine substitution at codon 1174 (F1174L) results in destabilization of the PF-02341066 binding site, whereas the R1275Q mutation has no predicted effect on this small molecule binding and thus competing with ATP.

Taken together, these data provide strong rationale for the clinical use of PF-02341066 for patients with neuroblastoma. This represents the first therapy for neuroblastoma specifically developed for a mutated oncogenic driver.

Example 4

Table 4 provides the frequency and spectrum of ALK mutation in diagnostic primary neuroblastomas (n=1148), as described hereinabove. Table 5 provides the frequency of mutations in various subsets of the population based on risk, as described hereinabove.

TABLE 4

Frequency and spectrum of ALK mutations in diagnostic primary neuroblastomas.

|  | All Patients | Mutation + |
|---|---|---|
| All Patients | 1148 | 84 (7.3%) |
| Age |  |  |
| <365 days | 438 (38%) | 29 (6.6%) |
| >365 days | 709 (62%) | 55 (7.8%) |
| >3650 days | 36 (3%) | 6 (17%) |
| INSS Tumor Stage |  |  |
| 1 | 288 (25%) | 14 (4.9%) |
| 2 | 211 (18%) | 21 (10%) |
| 3 | 172 (15%) | 10 (5.8%) |
| 4 | 401 (35%) | 36 (9%) |
| 4S | 76 (7%) | 3 (4%) |
| MYCN Status |  |  |
| Not Amplified | 984 (86%) | 65 (6.6%) |
| Amplified | 156 (14%) | 18 (11.5%) |
| Shimada Histopathology |  |  |
| Favorable | 629 (55%) | 43 (6.8%) |
| Unfavorable | 466 (41%) | 37 (7.9%) |
| DNA Ploidy |  |  |
| Diploid | 377 (33%) | 31 (8.2%) |
| Hyperdiploid | 729 (64%) | 51 (7%) |
| COG Risk Group |  |  |
| Low | 548 (48%) | 35 (6.4%) |
| Intermediate | 203 (18%) | 14 (6.9%) |
| High | 397 (34%) | 35 (8.8%) |

TABLE 5

Frequency of mutations in low risk, intermediate risk, and high risk samples.

| SAMPLE SET | TOTAL MUTATIONS | R1275 | F1174 | F1245 |
|---|---|---|---|---|
| LOW RISK (N = 548) | 35/548 (6.4%) | 16/36 (44%) | 7/23 (30%) | 6/11 (55%) |
| INT RISK (N = 203) | 14/203 (6.9%) | 6/36 (17%) | 6/23 (26%) | 1/11 (10%) |
| HIGH RISK (N = 397) | 35/397 (8.8%) | 14/36 (39%) | 10/23 (43%) | 4/11 (36%) |
| ALL TUMORS (N = 1148) | 84/1148 (7.3%) | 36/84 (43%) | 23/84 (27%) | 11/84 (13%) |

Example 5

Figure 16:
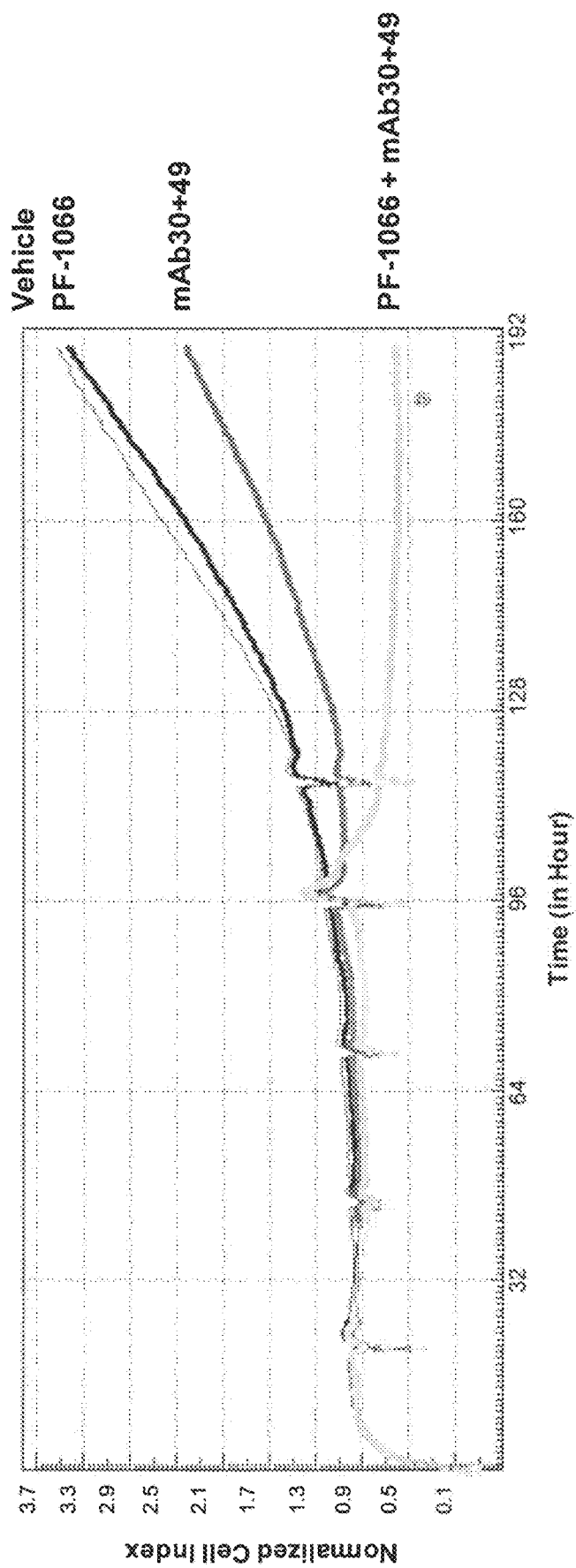
FIG. 16 is a graph of normalized cell index of SH-Sy5Y (F1174L) cells treated with vehicle, PF-1066, mAb30+49, or PF-1066 and mAb30+49.

The co-administration of ALK antibodies with a tyrosine kinase inhibitor induces cell death in cells that were less sensitive to the tyrosine kinase inhibitor alone. FIG. 16 shows the co-administration of PF-1066 with mAb 30 and 49 were significantly more effective than PF-1066 alone or mAb 30 and 49 alone against SH-Sy5Y (F1174L) cells. mAb 30 and 49 are described in Moog-Lutz et al. (J. Biol. Chem., (2005) 280:26039-26048).

Example 6

Anaplastic Lymphoma Kinase (ALK) was originally identified in an oncogenic fusion protein expressed in anaplastic large cell lymphoma (ALCL) as a result of a chromosomal translocation (Morris et al. (1994) Science 263: 1281-4). This fusion links the intracellular region of the ALK receptor tyrosine kinase (RTK) to the N-terminal portion of nucleophosmin (NPM), leading to constitutive kinase activation in an NPM-ALK fusion (Morris et al. (1994) Science 263:1281-4). Other oncogenic ALK fusions have since been identified in several human cancers, including non-small cell lung cancer (NSCLC), squamous cell carcinoma, and inflammatory myofibroblastic tumors (Soda et al. (2007) Nature 448:561-6; Rikova et al. (2007) Cell 131:1190-203; Jazii et al. (2006) World J. Gastroenterol., 12:7104-12; Griffin et al. (1999) Cancer Res., 59:2776-80). The full-length ALK RTK has also been linked to neuroblastoma, a pediatric cancer of the sympathetic nervous system that accounts for 10% of childhood cancer mortality (Miyake et al. (2002) Oncogene 21:5823-34; Maris et al. (2010) N. Engl. J. Med., 362:2202-11; Smith et al. (2010) J. Clin. Oncol., 28:2625-34). Intact ALK is expressed in the majority of neuroblastomas, suggesting a role in autonomic nerve development, and the ALK gene is amplified in 2-3% of cases (Lamant et al. (2000) Am. J. Pathol., 156:1711-21; Passoni et al. (2009) Cancer Res., 69:7338-46; Wang et al. (2006) Cancer Res., 66, 6050-62; George et al. (2007) PLoS One 2:e255). Herein, activating mutations within the tyrosine kinase domain of full-length ALK were identified as the major cause of familial neuroblastoma and were also shown to arise somatically in up to 10% of sporadic neuroblastoma cases (see also Janoueix-Lerosey et al. (2008) Nature 455: 967-70; Mosse et al. (2008) Nature 455:930-5). Amplification and mutation of ALK lead to its constitutive autophosphorylation and activation, and may be associated with a more aggressive clinical course (see also Passoni et al. (2009) Cancer Res., 69:7338-46; George et al. (2007) PLoS One 2:e255; Mosse et al. (2008) Nature 455:930-5; Osajima-Hakomori et al. (2005) Am. J. Pathol., 167:213-22; De Brouwer et al. (2010) Clin. Cancer Res., 16:4353-62).

Cure rates among children with high-risk neuroblastoma have shown only modest improvement, despite dramatic escalations in the intensity of therapy provided. Survivors of modern high-risk neuroblastoma therapy are at risk for major morbidities, many of which can be life-threatening (Hobbie et al. (2008) Pediatr. Blood Cancer 51:679-83; Oeffinger et al. (2006) N. Engl. J. Med., 355:1572-82). It is therefore clear that new approaches are required for treating neuroblastoma.

Materials and Methods
Cell Culture and Reagents

All cell lines were maintained in a 5% $CO_2$ incubator at 37° C. in RPMI (Invitrogen) supplemented with 10% fetal calf serum, L-glutamine, penicillin/streptomycin, and gentamicin (Invitrogen). Mouse monoclonal IgG1 antibodies 14, 30, 46 and 49 were generated to the extracellular domain of human ALK as previously described (Moog-Lutz et al. (2005) J. Biol. Chem., 280:26039-48). Crizotinib was obtained from Pfizer and diluted in dimethylsulfoxide (DMSO; Sigma) for use in cell culture. Murine IgG1 (Sigma-Aldrich) and DMSO were used respectively as negative controls.

Quantitative mRNA Expression

RNA from primary diagnostic tumor specimens of 229 children with neuroblastoma was obtained and analyzed using Affymetrix Human Exon Array (HuEx). HuEx arrays were normalized using quantile normalization and summarized using robust multichip average (RMA) using Affymetrix Power Tools software package version 1.12. ALK expression levels were obtained by averaging the core unique probesets for the ALK transcript (Transcript ID: 2546409). Data were analyzed for significance among patients diagnosed with low risk disease (stage 1 and 2 neuroblastoma, n=24), high risk metastatic MYCN non-amplified neuroblastoma (>18 months of age at diagnosis, n=141), and high risk MYCN amplified neuroblastoma (n=64). The overall p-value among the groups was carried out using likelihood ratio chi-squared tests in the context of a general linear model. Differences between two subgroups were assessed using the Wald test. The analyses were performed using the R statistical package (R version 12.1).

Immunohistochemistry

Cases were selected from a review of neuroblastic tumors accessioned to the Pathology Department of the Children's Hospital of Philadelphia from 1987 to 2004. Selection of specimens and construction of the tissue micro-array (TMA) followed approval by the Children's Hospital of Philadelphia Institutional Review Board. All tumors were reviewed by a pediatric pathologist for adequacy, and classified pathologically for diagnosis, grade, Shimada histology and mitotic-karyorrhectic index using International Neuroblastoma Pathology Classification criteria. The resultant TMA comprised two paraffin blocks and contained tumor cores from 126 patients, including 117 neuroblastomas and 9 nodular ganglioneuroblastomas. 0.6 mm cores of representative tumor tissue from each case were used to construct the tissue microarray blocks using a manual arrayer (Beecher Instruments). MYCN amplification status and stage (International Neuroblastoma Staging System, INSS) were obtained by tumor registry review. Staining of the TMA was conducted with prediluted anti-ALK-1 (Ventana Medical Systems), using pressure cooker antigen retrieval, overnight incubation, and avidin-biotin complex conjugation. Percent positivity of the neuroblasts within the cores was assessed, and intensity of staining was graded on a scale of 1-3 (weak, moderate, strong). An ALK staining score was calculated as the product of percentage of neuroblasts stained and grade of intensity.

Immunofluorescence

Cell lines were plated on Lab Tek II Chamber Slides (Thermo Scientific). After overnight incubation at 37° C., slides were transferred to ice and cells were washed three times with ice-cold PBS before blocking for 20 minutes with 10% BSA in PBS. Cells were next incubated for 60 minutes on a rocker table with ALK antibody mAb14 at a 1:100 dilution in 1.5% BSA/PBS. After three 5 minutes washes, cells were incubated for 45 minutes in the dark with Rhodamine-conjugated goat anti-mouse secondary antibody (Jackson) then washed 3×5 minutes and coverslipped with mounting media containing DAPI stain (Santa Cruz) for evaluation with a fluorescence microscope.

Flow Cytometry with ALK Antibodies

Cells were kept ice-cold during staining to minimize receptor endocytosis. Cells that had achieved 70-80% confluency were harvested and washed twice with ice-cold 1% FCS/PBS buffer containing 2 mM EDTA (Invitrogen), then ALK antibody mAb 14 was added as a staining antibody at a final concentration of 10 µg/ml. Cells were incubated 20 minutes on ice then washed twice. Donkey anti-mouse IgG PE (eBioscience) was then added at a concentration of 2.5 µg/ml and cells were incubated for 20 minutes on ice in the dark and washed. In some experiments, cells were grown in T25 flasks until 70-80% confluency and crizotinib was added (or DMSO as a negative control) and cells harvested at various subsequent timepoints for flow cytometry. In some experiments, staining was conducted with both the mAb14 and mAb46 which binds a distinct epitope from mAb14. Cells were then analyzed on an LSR II Flow Cytometer (BD Biosciences). All results shown are representative of at least 3 independent experiments.

Growth Inhibition

The Real-Time Cell Electronic Sensing (RT-CES) system (ACEA Biosciences, San Diego, Calif.) was used to measure the in vitro effect of the ALK antibodies mAb30 and mAb49 alone or in combination with the tyrosine kinase inhibitor crizotinib on neuroblastoma cell line growth. Cell lines were plated in triplicate in 96-well plates. Antibody and/or drug were first added 24 hours after plating, and antibody treatment was continued for four additional days. Growth inhibition was calculated as: 100*(1−(cell index treatment/cell index control)). All cell lines were routinely mycoplasma tested and genotyped using the AmpFLSTR Identifier kit (Applied Biosystems). All RT-CES experiments were conducted a minimum of three times, and results quoted as mean±standard deviation. For statistical analysis of results, linear mixed effect models were fitted to examine time and treatment effects. To account for nonlinearity, time by treatment and time square by treatment interaction terms were included in the models. F tests were used to examine the difference of the progression of cell index over time between each individual treatment and the combination treatment.

Calculation of $IC_{50}$

The RT-CES system was used to measure growth of cell lines plated in a 5-log dose range of 1-10,000 nM crizotinib alone or in combination with 10 µg/ml ALK mAb30 and mAb49. GraphPad Prism Version 5.0 was used to calculate the $IC_{50}$ from the RT-CES-generated cell index data using the log(inhibitor) vs. response—variable slope equation.

Western Blots

Cells were grown in 10 cm dishes until 70-80% confluency, at which point 1000 nM crizotinib, 10 µg/ml ALK antibody, both agents, or the relevant negative controls were added. After 72 hours of incubation, flasks were transferred to ice, washed with ice cold PBS, and cells scraped into ice-cold PBS. After pelleting, whole cell lysates were harvested and immunoblotted with either antibodies against ALK (1:1,000; Cell Signaling, 3333), phospho-ALK Tyr 1604 (1:1,000, Cell Signaling, 3341), or actin (1:2000; Santa Cruz, sc-1616). Results shown are representative of two independent experiments.

Propidium Iodide Staining

SY5Y cells were plated in 6-well plates at 2×105 cells per well. After 24 hours, 1000 nM crizotinib, 10 µg/ml ALK antibody, both agents, or the appropriate negative controls, were added. Antibody treatment was continued for four additional days. Cells were then harvested and washed twice. Ice-cold ethanol was added while vortexing, and cells were allowed to stand for 20 minutes at 4° C. Cells were again washed twice and then resuspended in phosphate-citric acid buffer and allowed to stand at room temperature for 5 minutes. After washing, cells were resuspended in a 1% FBS solution containing RNAseA (Roche) and 50 µg/ml propidium iodide (Sigma-Aldrich) and incubated at room temperature in the dark for 30 minutes. Cells were then analyzed on an LSR II flow cytometer.

Antibody-Dependent Cell-Mediated Cytotoxicity Assay

The Cyto Tox 96 Non-Radioactive Cytotoxicity Assay (Promega) was used to assess antibody-dependent cell mediated cytotoxicity. Normal donor peripheral blood mononuclear cells were used as effectors and plated in 10 cm dishes in complete RPMI for 2 hours at 37° C. to allow monocytes to adhere. Non-adherent peripheral blood lymphocytes were then replated in complete RPMI containing 1000 IU/ml rhIL-2 (Chiron) and incubated overnight. The following day, effector cells were collected and washed. Target NB1 or SY5Y cells that had been grown on T75 flasks until 70-80% confluency were also harvested and washed. In some experiments, SY5Y cells were pre-incubated for 48 hours in crizotinib before being used as target cells in the ADCC. Effector and target cells were then plated in quadruplicate at effector:target ratios of 50:1, 25:1, and 10:1 and experimental wells treated with 1 µg/ml ALK mAb30 and mAb49. Control wells were plated according to the manufacturer's specifications. After a 4-hour incubation at 37° C., cell viability was assessed by an enzymatic assay allowing for the quantification of lactate dehydrogenase which is released upon cell lysis. The % cytotoxicity was calculated as follows: [(Experimental−Effector Spontaneous−Target Spontaneous)/(Target Maximum−Target Spontaneous)]×100. To ensure specificity of the ALK antibody, separate experiments were conducted comparing untreated wells to treatment with 1 µg/ml murine IgG1. No difference was detected between untreated (mean % cytotoxicity=3.1%, SD=0.3%) and IgG1-treated wells (mean % cytotoxicity=0.64%, SD=0.28%; p=0.8822). Results shown are representative of three independent experiments, and quoted as mean±standard deviation.

Results

ALK is Widely Expressed in Neuroblastoma Tumors and Cell Lines

Figure 17A:
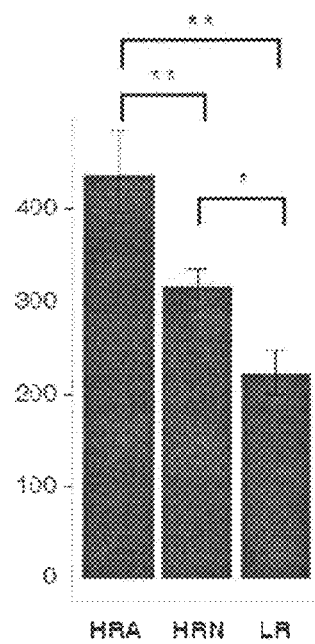
FIG. 17A provides a graph showing ALK expression in 229 neuroblastoma patient tumors analyzed by Affymetrix Human Exon Array and normalized using quantile normalization (HRA=High risk MYCN amplified neuroblastoma, n=64; HRN=High risk MYCN non-amplified neuroblastoma, n=141; LR=Low risk, n=24).

Successful immunotherapy requires the targeted antigen to be expressed selectively in tumors, but not in normal tissue. Moreover, the targeted antigen must be expressed on the majority of tumors for immunotherapy to be relevant to a large proportion of patients, and expression levels should ideally be related directly to measures of disease severity. Since intact ALK is normally found only in the developing embryonic and neonatal brain (Iwahara et al. (1997) Oncogene 14:439-49), it could be a valuable target for immunotherapy if expressed in the majority of tumors. To assess ALK expression in primary patient tumors, data from Wang et al. (Cancer Res. (2006) 66:6050-62) as well as the TARGET initiative (Therapeutically Applicable Research to Generate Effective Treatments: target.cancer.gov/). As shown in FIG. 17A, ALK mRNA expression is seen in tumors from patients with clinically aggressive disease, especially in those with high-risk metastatic disease and/or MYCN amplification [p=5.06E-05 for high-risk MYCN amplified (HRA) vs. low-risk (LR), p=0.0022 for HRA vs. high-risk MYCN non-amplified (HRN), p=0.0211 for HRN vs. LR]. To verify ALK expression at the protein level, a tissue microarray of diagnostic neuroblastomas and ganglioneuroblastomas was analyzed. Samples from 126 patients were stained for native ALK expression with anti-ALK-1 and graded the intensity of ALK staining on a scale of 1-3

Figure 17B:
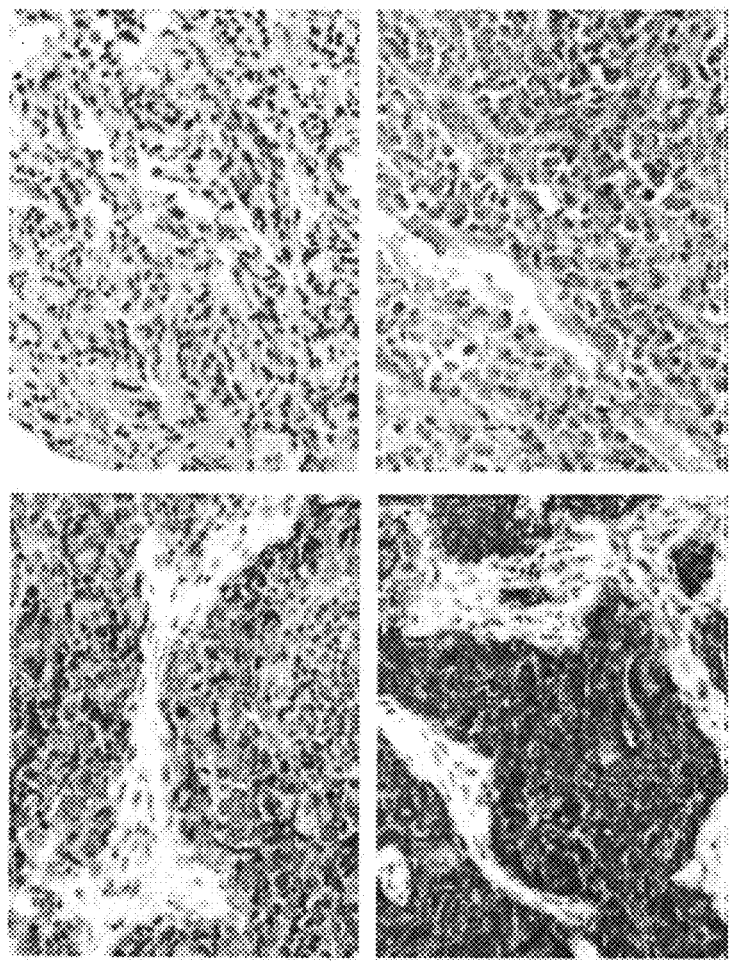
FIG. 17B provides representative images for immunohistochemical staining of ALK in neuroblastoma patient tumors. ALK staining was positive overall in 109 of 126 (86.5%) samples analyzed. 17 samples showed no positive staining (upper left panel); 35 showed weak/Grade 1 staining (upper right panel); 55 showed moderate/Grade 2 staining (lower left panel); and 19 showed strong/Grade 3 staining (lower right panel).
Figure 17C:
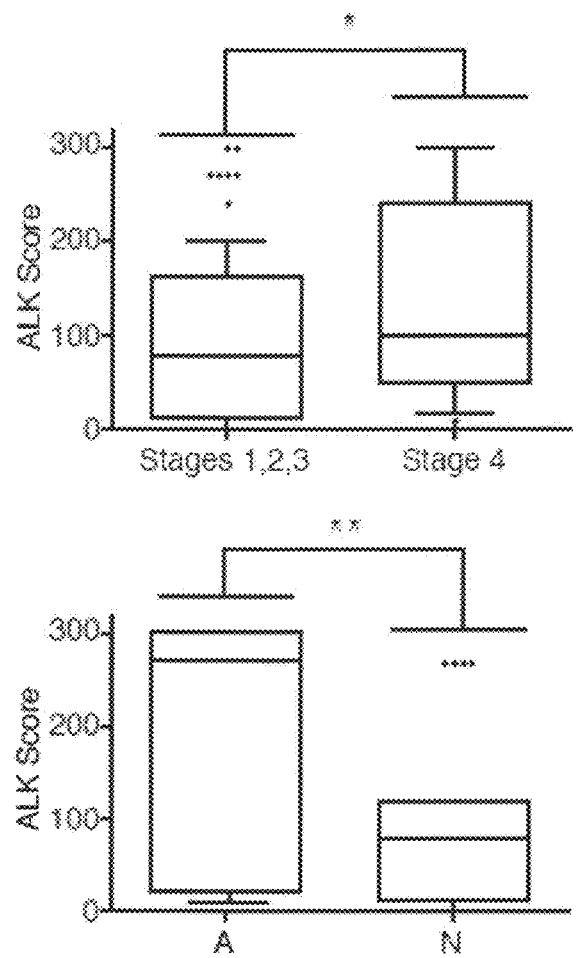
FIG. 17C provides box plots showing 10th percentile, 90th percentile, and mean ALK score by immunohistochemistry for INSS stage (top panel) and MYCN status (bottom panel; A=MYCN amplified, N=MYCN non-amplified). **, p<0.01; *, p<0.05.

(representative samples shown in FIG. 17B) and percent positivity. Among the samples analyzed, 109 (86.5%) were ALK-positive, with 75 samples (59.5%) having either moderate (grade 2) or strong (grade 3) staining. Moreover, as shown in FIG. 17C, ALK expression was significantly stronger in patients with INSS stage 4 (p=0.0108; top panel) or amplified MYCN (p=0.0065; bottom panel). These data indicate that ALK is expressed in the vast majority of neuroblastoma tumors, and that expression levels are higher in those patients with the worst prognosis.

Figure 17D:
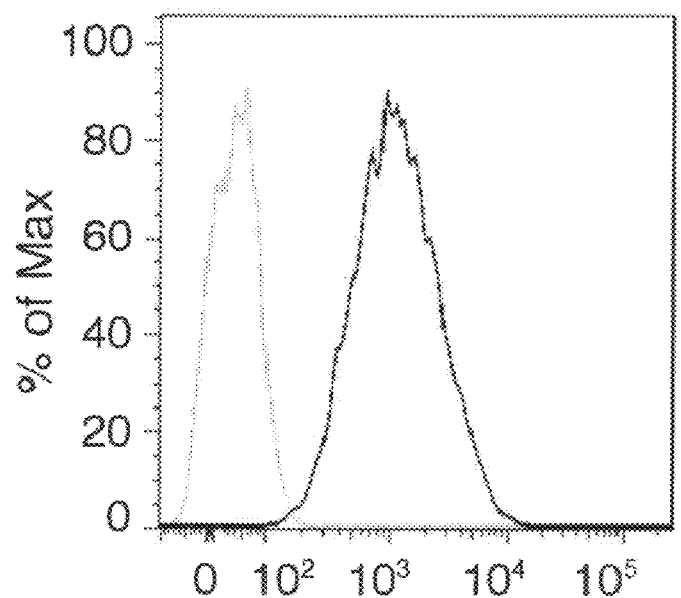
FIG. 17D provides a representative flow cytometry analysis of NB1 cells with an ALK antibody to assess cell-surface expression levels. Mean fluorescence intensity (MFI) is shown for ALK staining (black line) and an isotype control (grey line).
Figure 17E:
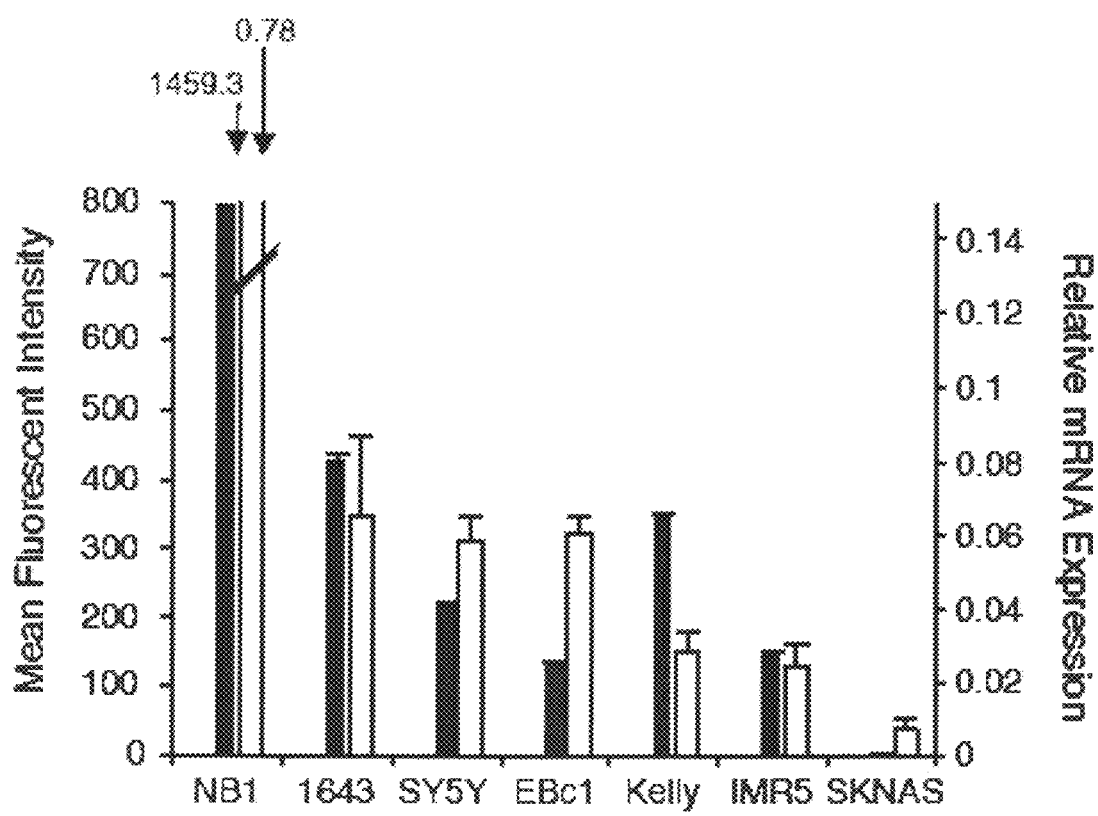
FIG. 17E provides a graph showing the comparison of flow cytometry results for several neuroblastoma cell lines. Grey bars show flow cytometry results for ALK cell surface staining. White bars represent an ALK mRNA expression 'index' (relative expression) measured as ALK levels relative to HPRT1.
Figure 17F:
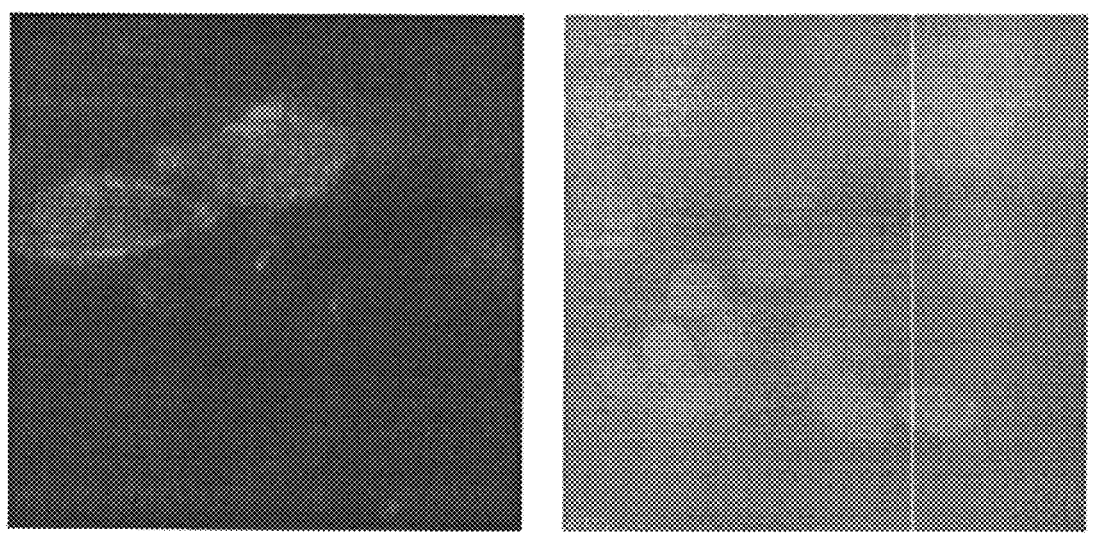
FIG. 17F provides immunofluorescence staining of neuroblastoma cells lines with anti-ALK demonstrates cell surface ALK expression for NB1 (left panel) and SY5Y cells (right panel).

Since ALK expression at the cell surface is a prerequisite for ALK-targeted immunotherapy to be effective, flow cytometry was used to quantify cell surface ALK levels in a panel of human neuroblastoma-derived cell lines. As shown in FIGS. 17D and 17E, ALK was abundant on the cell surface of cell lines expressing either wild-type ALK (NB1, EBc1, and IMR5) or mutated ALK (1643, R1275Q; SY5Y, F1174L; Kelly, F1174L) when compared to the negative control SKNAS line that has been shown to have no detectable ALK expression (see above and Mosse et al. (2008) Nature 455:930-5). As also shown in FIG. 17E, cell surface ALK expression corresponded closely with relative ALK mRNA expression as measured by quantitative RT-PCR. To further analyze cell surface ALK expression, immunofluorescence staining of the neuroblastoma cell lines NB1 and SY5Y was conducted (FIG. 17F). Consistent with the results of flow cytometry, ALK was detected at the plasma membrane of both cell lines. These data indicate widespread expression and cell surface localization of full-length ALK in neuroblastoma.

An ALK Antibody Induces Growth Inhibition and Cytotoxicity

Figure 18A:
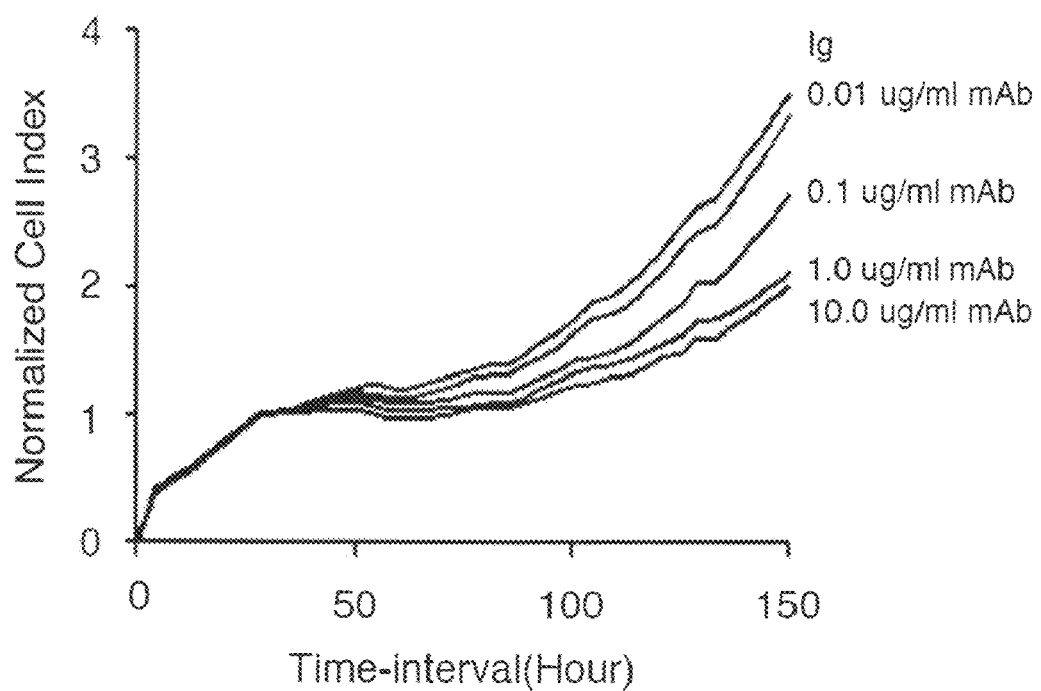
FIG. 18A provides a graph showing ALK antibody-induced growth inhibition and ADCC of neuroblastoma cells. To measure growth inhibition upon antibody exposure, cell lines were plated in 96-well plates and treated with anti-ALK (mAb30 plus mAb49) or a negative control murine IgG1. Cell growth was monitored by Real Time Cell Electronic Sensing (RT-CES) impedance measurement. Growth inhibition of SY5Y cells treated with indicated amounts of anti-ALK as compared to control Ig.
Figure 18B:
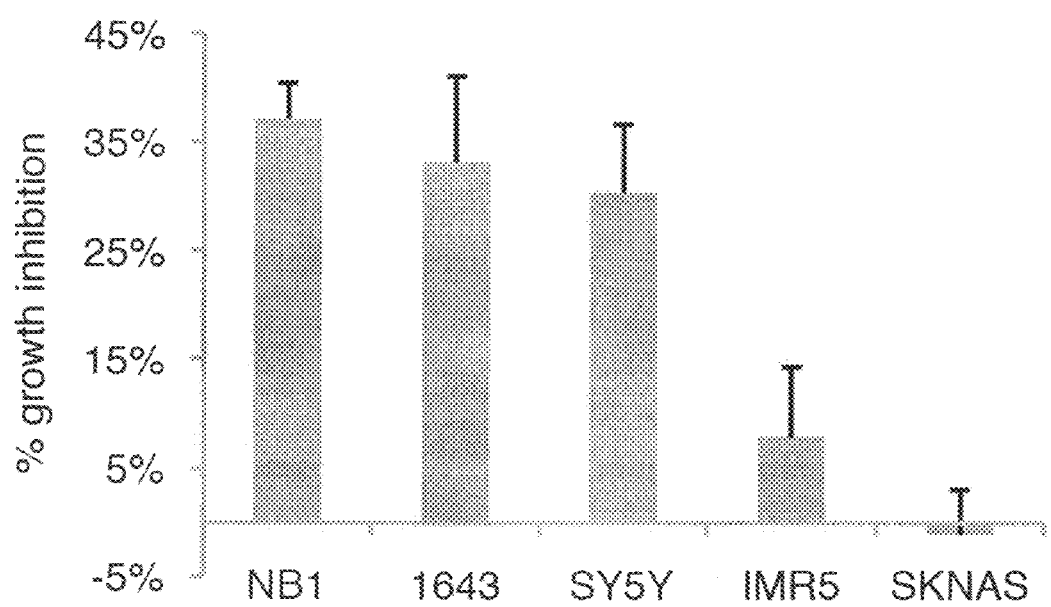
FIG. 18B shows the indicated cell lines were treated with 10 μg/ml ALK antibody and growth inhibition was measured after 144 hours.
Figure 18C:
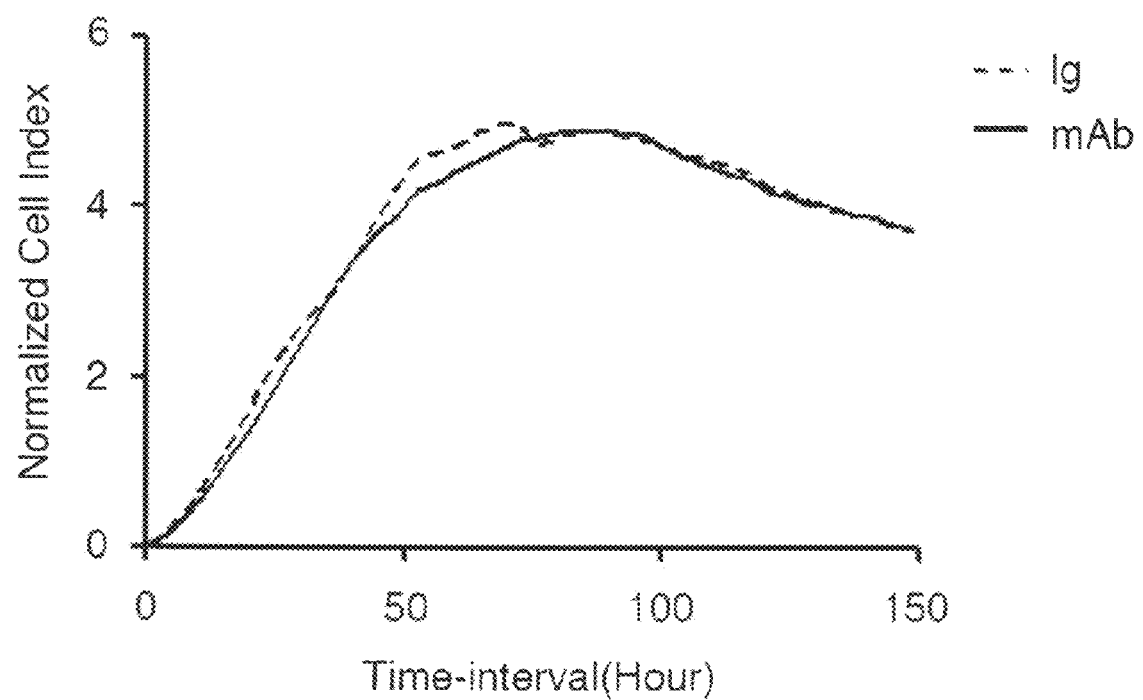
FIG. 18C provides a graph showing the effect of anti-ALK antibody on RPE1 cell growth. ALK-negative RPE-1 cells were plated in 96-well plates and treated with either 10 μg/ml anti-ALK antibody or murine immunoglobulin. Shown is cell growth for each condition as measured by RT-CES.

Having established that extracellular ALK antigens are accessible at the surface of neuroblastoma cell lines, it was then determined whether an antagonistic ALK monoclonal antibody identified by Moog-Lutz et al. (J. Biol. Chem. (2005) 280:26039-48) can inhibit growth of a neuroblastoma cell line driven by expression of activated ALK. First SY5Y cells (which express F1174L-mutated ALK) were treated with a 3-log dose range of a mixture of two ALK antibodies (mAb30 and mAb49), and growth was measured over 152 hours relative to control-treated cells (FIG. 18A). Although SY5Y cells express high levels of phospho-ALK, they are relatively insensitive to growth inhibition by crizotinib. However, treatment with the ALK antibody resulted in significant dose-dependent growth inhibition as compared to cells treated with control immunoglobulin. To assess whether this effect is general, a panel of well-characterized neuroblastoma cell line models harboring wild-type ALK (IMR5), mutated ALK (1643 and SY5Y), amplified ALK (NB1), or undetectable ALK (SKNAS) were treated with a fixed concentration of mAb30 and mAb49 (10 µg/ml total). As shown in FIG. 18B, there was a direct correlation between ALK expression levels and antibody-induced cytotoxicity, with the ALK amplified line NB1 showing the greatest sensitivity to antibody treatment, and the ALK-negative cell line SKNAS showing no growth inhibition. As an additional negative control, retinal pigmented epithelial cells (RPE-1)—a non-neuroblastoma, ALK-negative, neural crest-derived cell line—was treated with 10 µg/ml ALK antibody or murine immunoglobulin as above, and saw no growth inhibition (FIG. 18C). Importantly, given their variable sensitivity to ALK-targeted TKIs, cell lines expressing mutated ALK (1643 and SY5Y) showed significant degrees of antibody-induced cytotoxicity.

Figure 18D:
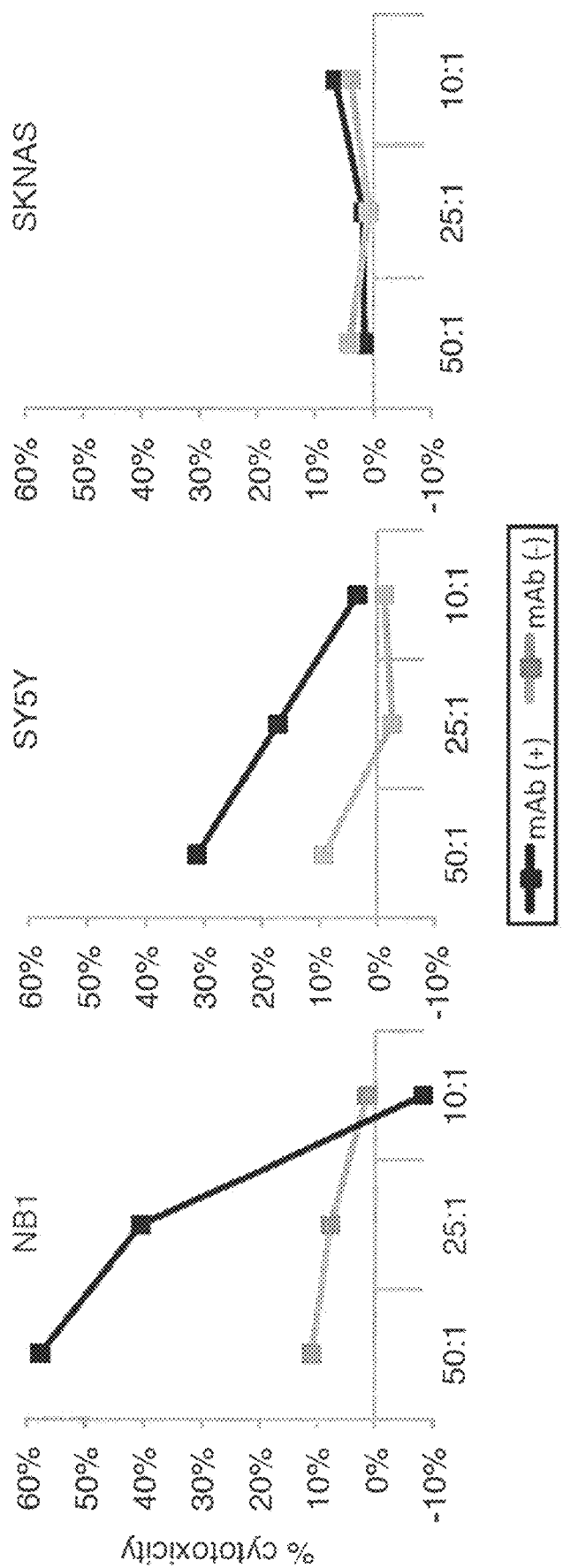
In FIG. 18D, ADCC was measured using an in vitro assay in which normal donor peripheral blood lymphocytes (PBL), pre-incubated overnight with IL-2, were co-incubated for four hours with neuroblastoma cells in the presence (black line) or absence (grey line) of 1 μg/ml ALK antibody. Shown are % cytotoxicity at the indicated effector:target ratios when NB1 cells (left panel), SY5Y cells (middle panel), or ALK-negative SKNAS cells (right panel) were used as targets.

Immune cell-mediated ADCC has been shown to be important for the mechanism of action of the GD2 antibody in neuroblastoma, and this effect is substantially enhanced in the presence of interleukin-2 (IL-2) (Hank et al. (1990) Cancer Res., 50:5234-9). To explore whether an ALK antibody is also capable of inducing an immune-mediated anti-tumor response in neuroblastoma, in vitro ADCC assays were conducted in which normal donor peripheral blood lymphocytes (PBL) were used as effectors, and neuroblastoma cell lines used as targets. Lymphocytes pre-incubated with IL-2 induced substantially higher levels of cytotoxicity in NB1 cells treated with anti-ALK mAb30 and mAb49 than in untreated cells (FIG. 18D, left panel). F1174L-expressing SY5Y cells also showed cytotoxicity in this assay (FIG. 18D, middle panel), although less than seen for NB1 cells, possibly because of the lower cell surface ALK levels seen by flow cytometry (FIG. 17E). No ADCC was detected when SKNAS cells (untreated or antibody-treated) were used as targets (FIG. 18D, right panel), consistent with their lack of ALK expression. Thus, targeting ALK with an antagonistic antibody can effectively inhibit growth and induce cytotoxicity of neuroblastoma cell lines harboring either wild-type or mutated forms of activated ALK.

Crizotinib Treatment Induces Cell Surface Accumulation of ALK

Treatment with a combination of TKIs and therapeutic antibodies that both target the same tumor antigen, such as EGFR (Regales et al. (2009) J. Clin. Invest., 119:3000-10) or HER2 (Scaltriti et al. (2009) Oncogene 28:803-14), has been shown to enhance the degree of tumor growth inhibition and cytotoxicity that can be elicited by either agent alone. One possible mechanism for this is increased cell surface accumulation of the targeted RTK that results from RTK stabilization upon TKI binding (Bougherara et al. (2009) Mol. Cancer Res., 7:1525-33; Tabone-Eglinger et al. (2008) Clin. Cancer Res., 14:2285-94). Certain activating RTK mutations, including several in c-Kit, may destabilize the RTK and cause intracellular (likely endoplasmic reticulum) accumulation that can be reversed by TKI treatment—leading to increased cell surface expression (Bougherara et al. (2009) Mol. Cancer Res., 7:1525-33; Tabone-Eglinger et al. (2008) Clin. Cancer Res., 14:2285-94). The relatively reduced sensitivity of F1174L ALK expressing SY5Y cells to ALK antibody treatment (FIG. 18B, 18D) prompted us to investigate a similar possibility for ALK.

Figure 19A:
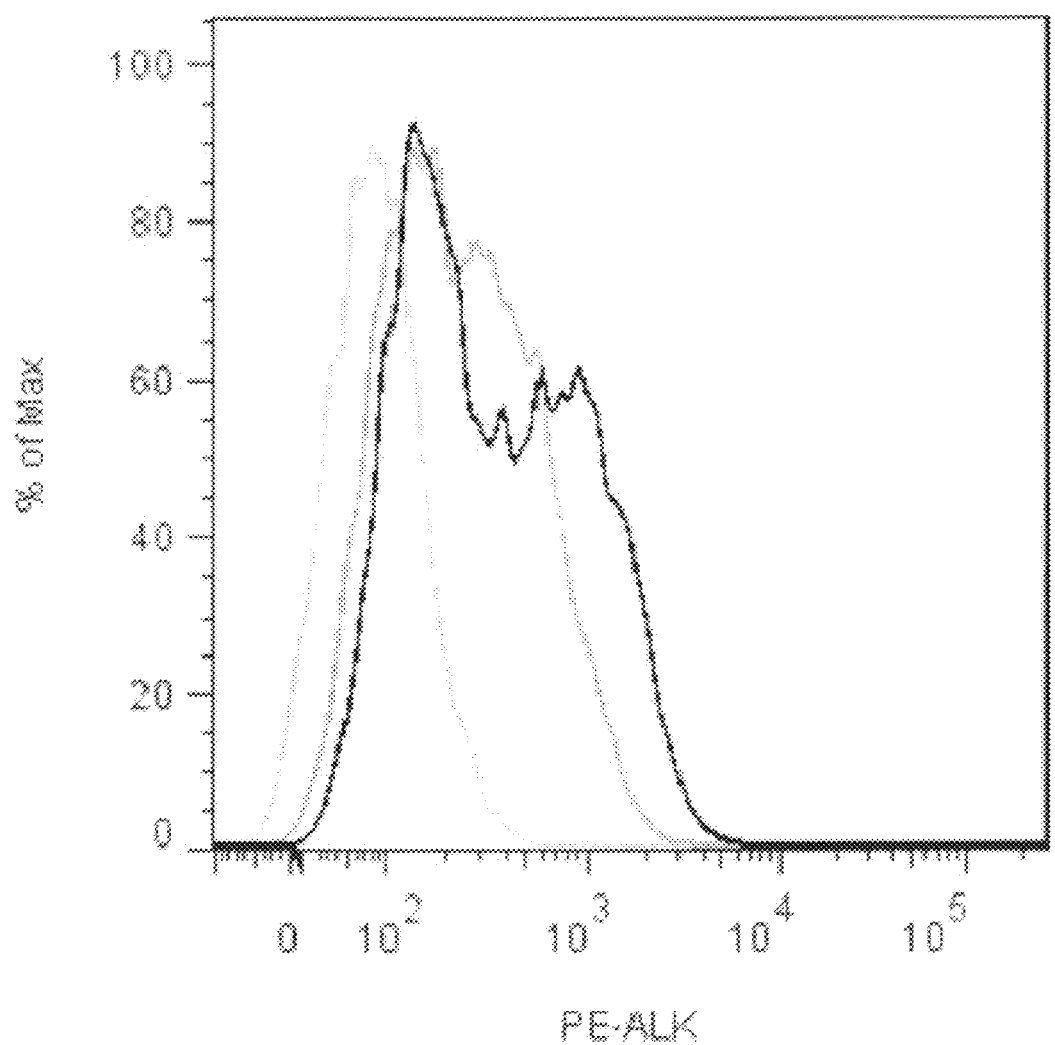
FIG. 19A shows the effect of crizotinib on cell surface ALK expression. SY5Y cells were incubated with crizotinib or vehicle, harvested and stained for cell surface ALK with mAb14. ViaProbe viability stain was used to exclude non-viable cells. A representative flow cytometry result is shown for SY5Y cells incubated for 72 hours with either vehicle (medium gray line) or 1000 nM crizotinib (black line). The single-peaked light grey line represents the isotype control.
Figure 19B:
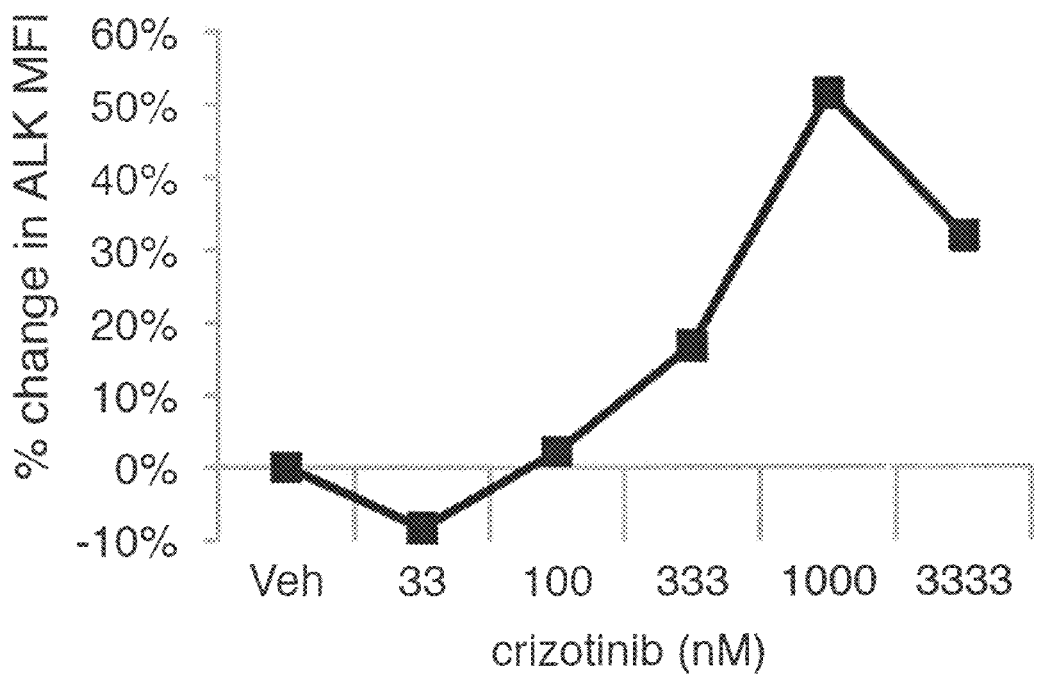
FIG. 19B shows the concentration dependence of the percent change in cell surface ALK, as measured by Mean Fluorescence Intensity (MFI), for cells incubated for 72 hours with varying concentrations of crizotinib as compared to vehicle.
Figure 19C:
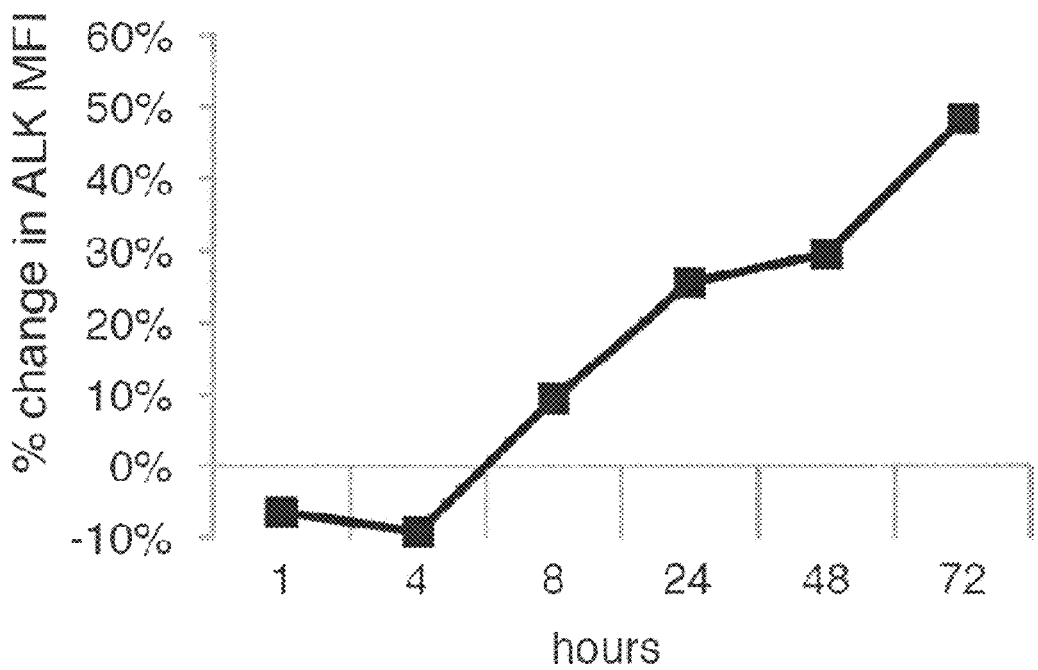
FIG. 19C provides a time course of percentage change in cell surface ALK levels (over that seen for vehicle treatment) when cells were incubated with 1000 nM crizotinib.
Figure 19D:
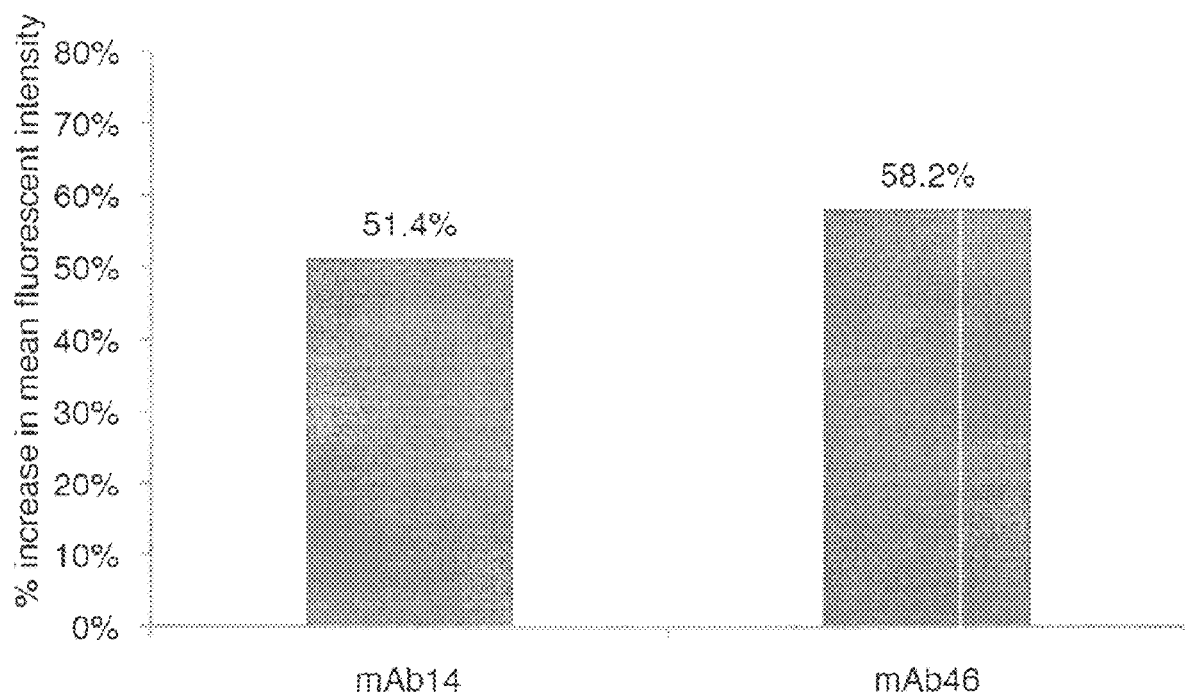
FIG. 19D shows a comparison of ALK antibodies for flow cytometry. SY5Y cells were treated with 1000 nM crizotinib or vehicle, harvested 72 hours later, and stained for flow cytometry. Shown is the percent increase in ALK MFI for crizotinib versus vehicle treated cells using either the mAb14 or mAB46 anti-ALK antibodies.

To explore the effects of TKIs on surface ALK levels in neuroblastoma cells, SY5Y cells were treated with a range of crizotinib doses (or vehicle). After 72 hours, cells were harvested and analyzed for cell surface ALK expression by flow cytometry. As shown in FIG. 19A, treatment with 1000 nM crizotinib resulted in a substantial increase in cell surface ALK levels for SY5Y cells, with a 51.4% increase in mean fluorescence intensity for cells treated with 1000 nM crizotinib (MFI=636) compared with vehicle treated SY5Y (MFI=420), or isotype control-stained (MFI=90). The enhancement in cell surface ALK levels was dose dependent (FIG. 19B), and increased with the time of crizotinib exposure (FIG. 19C). Up-regulation of cell surface ALK levels in crizotinib-treated cells was first evident at approximately 8 hours post-treatment, and continued to increase over the 72 hour period tested. The possibility that crizotinib binding might induce conformational changes in ALK that could stabilize or expose the epitope to which the staining antibody was binding—increasing antibody binding and thus the fluorescence signal in flow cytometry—was also considered. To control for this possibility, the experiment was repeated using a second anti-ALK antibody (mAb46) known to bind to an epitope distant from that of mAb14 (Moog-Lutz et al. (2005) J. Biol. Chem., 280:26039-48). Crizotinib-induced enhancement of cell surface ALK levels was also observed in this experiment (FIG. 19D), indicating that crizotinib promotes cell surface accumulation of its target RTK.

Crizotinib Sensitizes Cells to Growth Inhibition by ALK Antibody Treatment

Figure 20A:
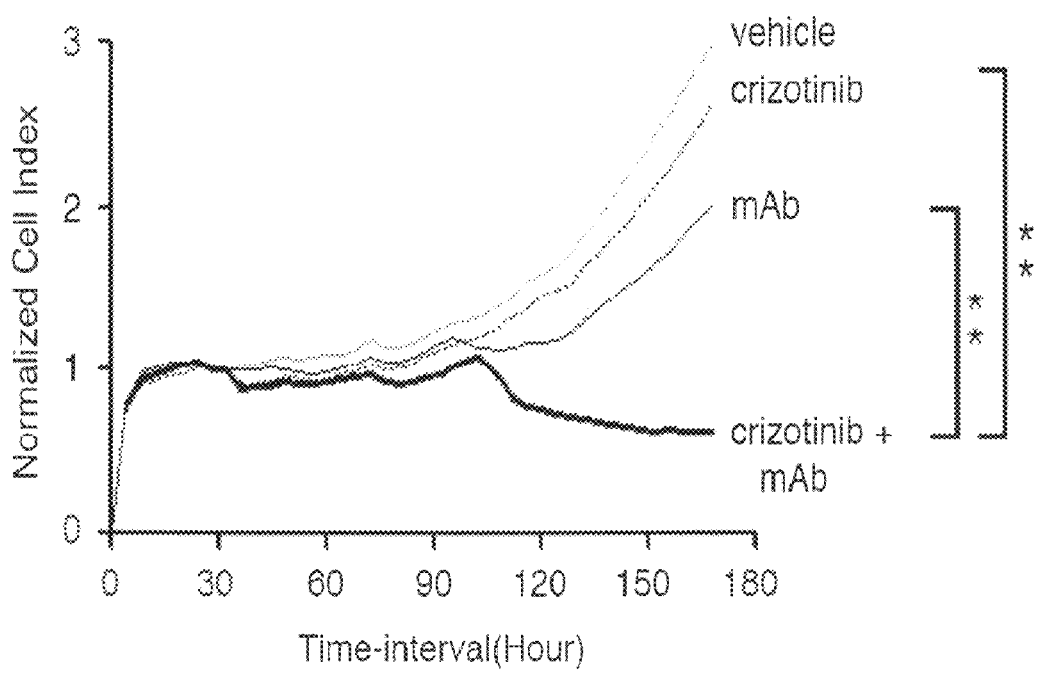
FIGS. 20A-20C show dual antibody/TKI targeting of ALK. SY5Y cells were treated with either 333 nM crizotinib or 10 μg/ml anti-ALK antibody (mAb30+mAb49), or both. As negative control, cells were treated with equal volumes of DMSO and 10 μg/ml IgG1.
Figure 20B:
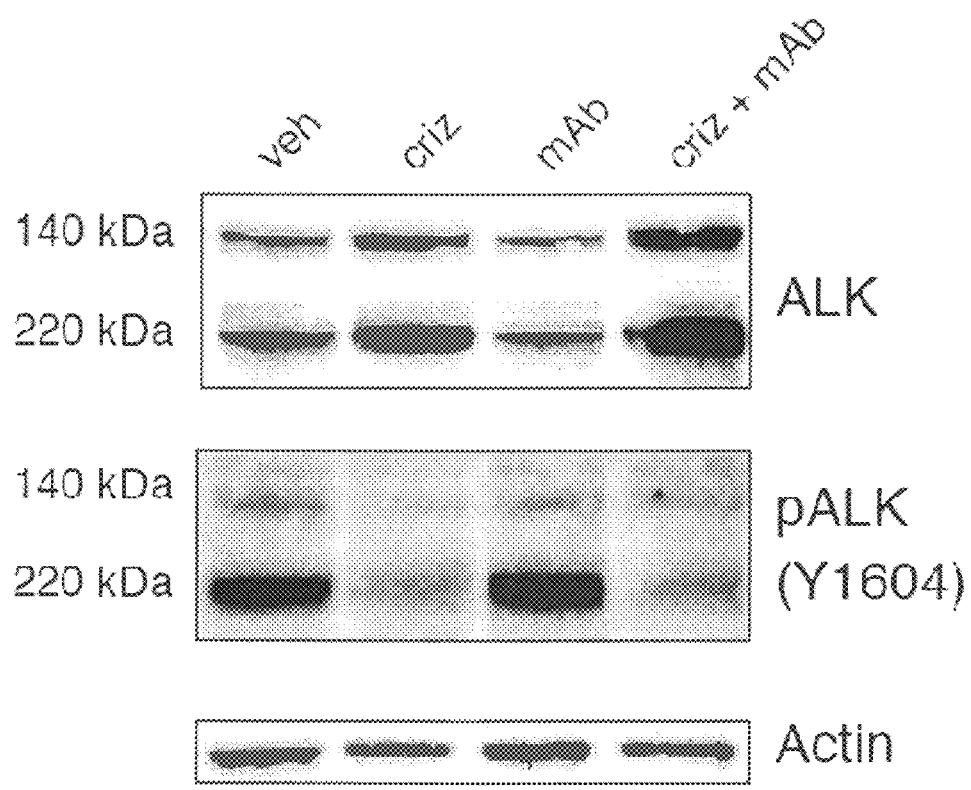
Figure 20C:
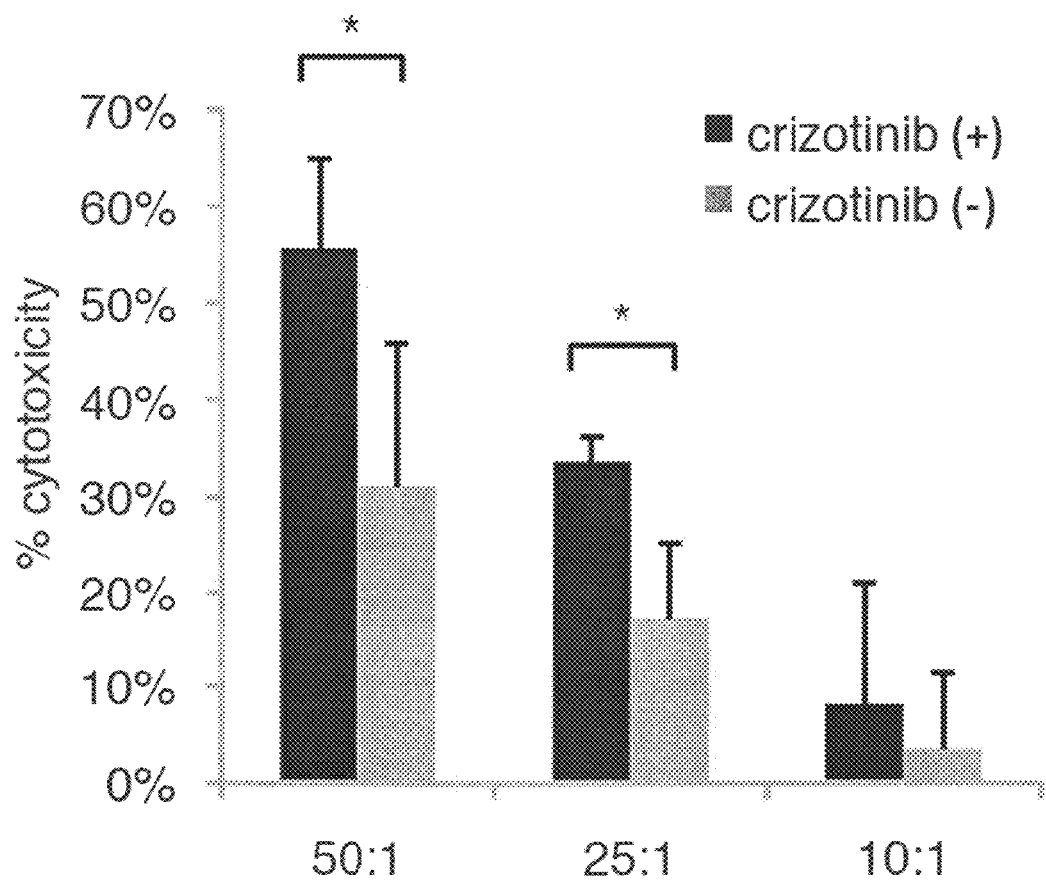

To test the hypothesis that crizotinib-induced accumulation of cell surface ALK sensitizes cells to ALK antibody treatment, the ability of the antagonist ALK antibody to inhibit growth of SY5Y cells alone or in combination with crizotinib was compared. As shown in FIG. 20A, treatment with either crizotinib alone (at a sub-$IC_{50}$ dose of 333 nM) or ALK antibody alone (at 10 μg/ml) led to measurable growth inhibition. However, combined treatment with both TKI and ALK antibody had a significantly larger inhibitory effect as compared to TKI alone ($p<0.0001$) or antibody alone ($p<0.001$), leading to almost complete growth inhibition of SY5Y cells in vitro. Increases in total ALK levels were also seen by Western blotting (FIG. 20B) in cells treated with crizotinib (alone or in combination with ALK antibody), consistent with the flow cytometry results shown in FIG. 19. On the other hand, levels of phosphorylated ALK were substantially diminished by treatment with crizotinib, either alone or together with antibody (FIG. 20B), suggesting that the TKI stabilizes ALK while simultaneously blocking its activation. It also considered whether crizotinib-induced up-regulation of cell surface ALK might promote ADCC-mediated effects of the ALK antibody. To address this, the in vitro ADCC assays was repeated using lymphocytes as effectors and SY5Y cells pre-incubated with crizotinib or vehicle as targets. As shown in FIG. 20C, crizotinib pre-incubation significantly increased ADCC at effector to target ratios of 50:1 (crizotinib-treated mean=55.7±9.3%; vehicle-treated mean=31.1±14.7%; p=0.0331) and 25:1 (crizotinib-treated mean=33.7±2.5%; vehicle-treated mean=17.3%±7.9%; p=0.0262), providing further evidence for the ability of crizotinib to sensitize ALK-mutated neuroblastoma cells to ALK antibody treatment.

ALK Antibody Improves Sensitivity to a Broad Range of Crizotinib Doses

Figure 21A:
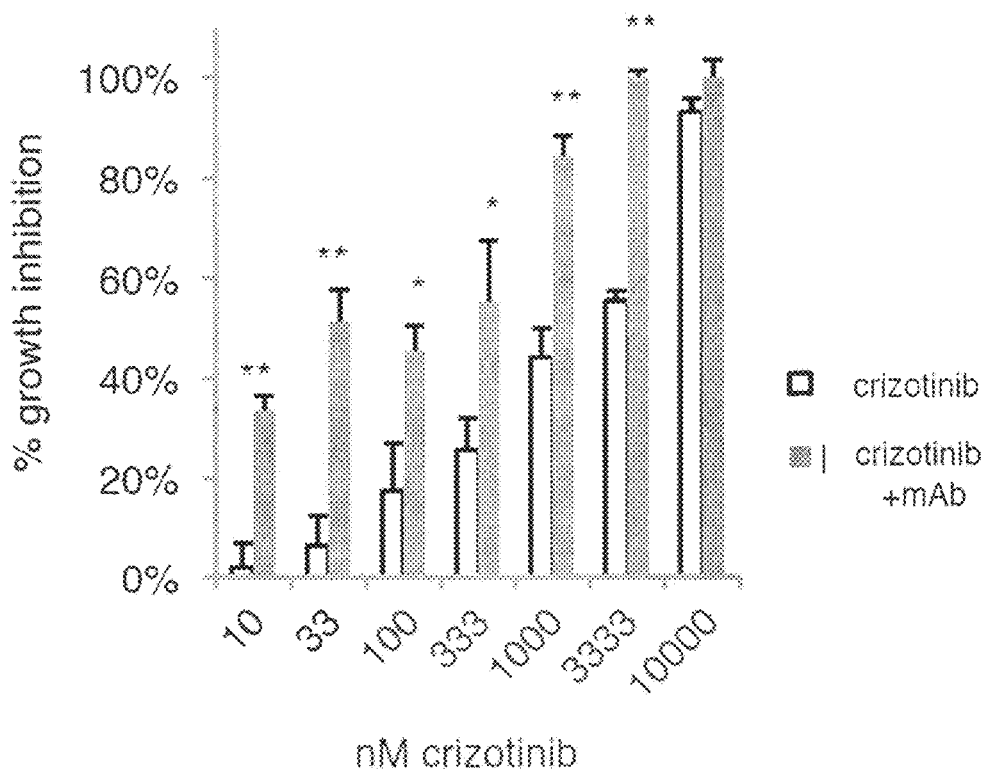
FIGS. 21A-21B show the effects of an antagonist ALK antibody on crizotinib dose-response curve. SY5Y cells were treated with crizotinib at the indicated doses either alone or in combination with 10 μg/ml (total) ALK antibody mAb30 and mAb49. Cell growth was measured at day 7 using RT-CES.
Figure 21B:
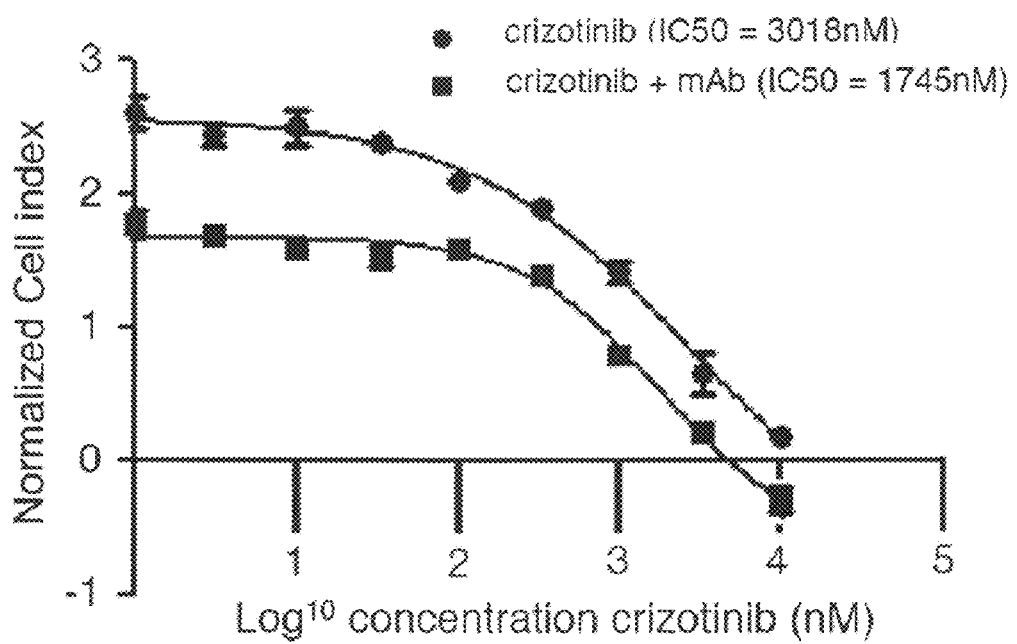

Since the previous experiments were conducted at a fixed dose of crizotinib, it was then explored whether ALK antibody treatment could improve sensitivity of neuroblastoma cells to crizotinib treatment across a range of doses. SY5Y cells were treated with a 4-log range of crizotinib doses in the presence or absence of ALK antibody. As shown in FIG. 21A, the addition of ALK antibody significantly enhanced growth inhibition at all crizotinib doses except for the highest dose of 10,000 nM, a supra-lethal dose at which the majority of TKI effect is likely to be off-target. Moreover, these data reveal that combining the ALK antibody shifts the dose-response curve for crizotinib so that a low dose (10 nM) of crizotinib in combination with anti-ALK induces more growth inhibition (mean=33.7±2.8%) than seen with 333 nM crizotinib alone (mean=25.7%, SD=6.5%). As suggested by this finding, antibody treatment reduced the $IC_{50}$ for crizotinib treatment of SY5Y cells from 3018 nM (crizotinib alone) to 1745 nM for dual therapy (FIG. 21B).

Dual ALK Targeting Enhances Programmed Cell Death

Figure 22A:
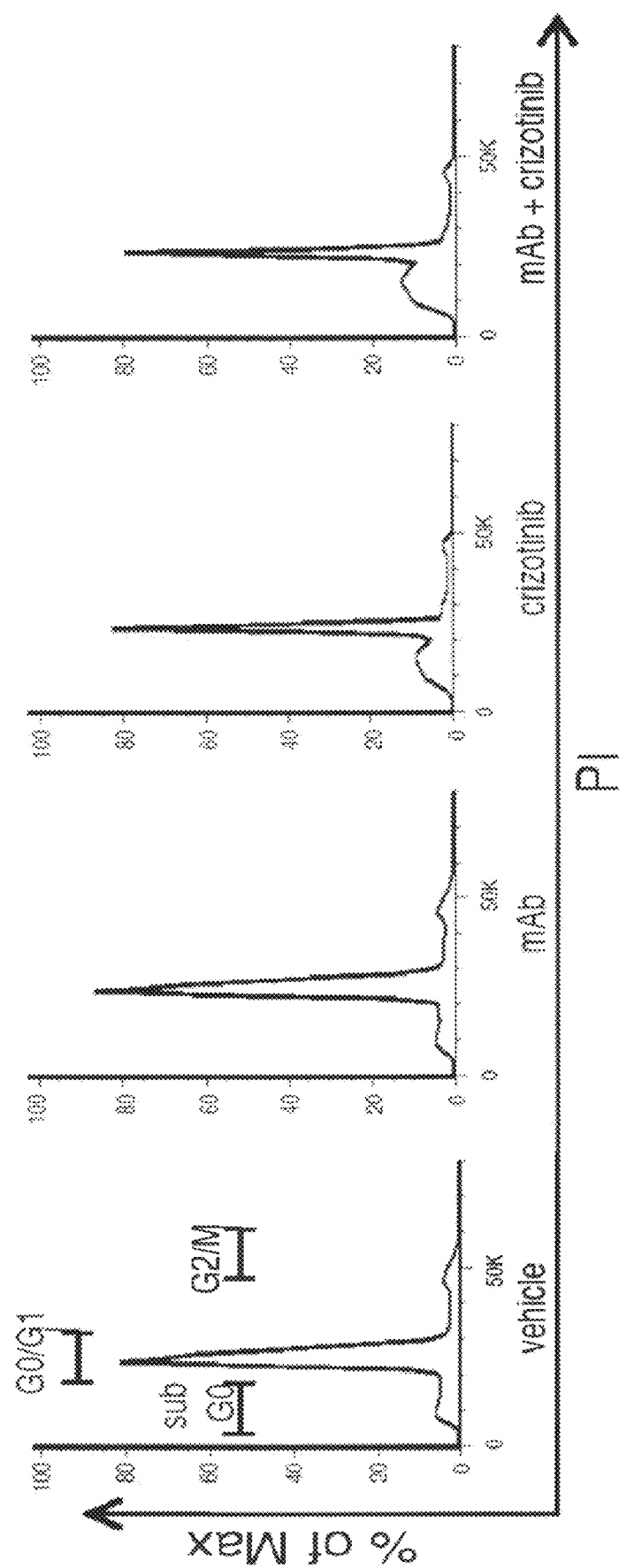
FIGS. 22A-22B shows the cell cycle analysis of inhibitor-treated cells. SY5Y cells were treated with 1000 nM crizotinib, 10 μg/ml antibody, both, or vehicle/IgG1, and were then harvested, fixed, stained with propidium iodide, and analyzed by flow cytometry.
Figure 22B:
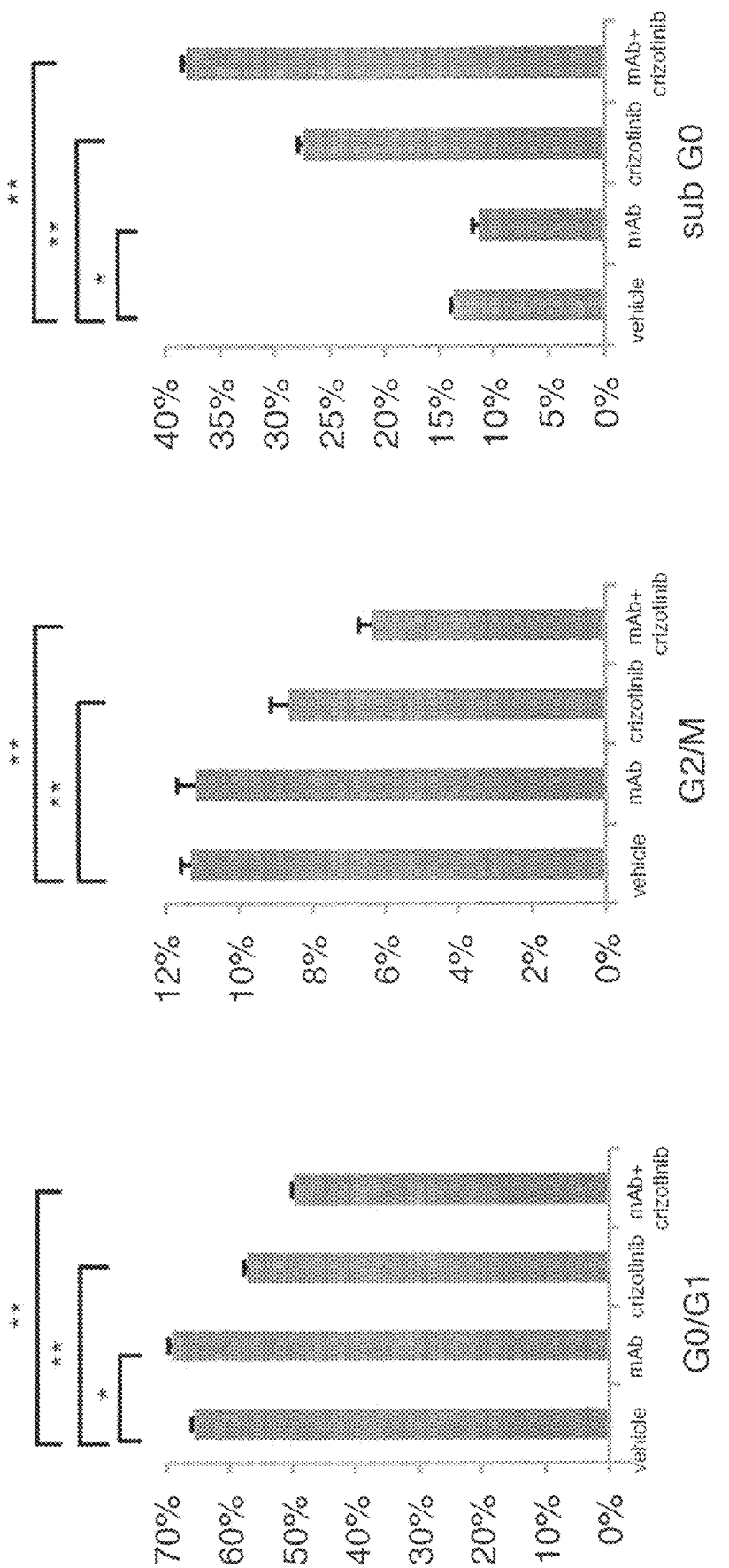

To determine the effect of crizotinib and ALK antibody treatment on cell cycle progression, the impact of TKI and/or antibody exposure on SY5Y cellular DNA content was analyzed by flow cytometry. As shown in FIG. 22A, and quantified in FIG. 22B, treatment with antibody alone led to a small, but significant, increase in the G0/G1 fraction (antibody-treated mean=69.2±0.5%; vehicle-treated mean=65.7±0.3%) and a small but significant decrease in the sub G0 fraction (antibody treated mean=11.4±0.3%; vehicle-treated mean=13.7±0.2%), suggesting that the main mechanism of antibody action may be G1 arrest. On the other hand, dual antibody and TKI ALK targeting led to large and significant increases in the sub G0 fraction (mAb+crizotinib–treated mean=38.0±0.4%), suggesting induction of programmed cell death as the dominant mechanism of dual ALK targeting. Treatment with crizotinib alone also increased the sub G0 fraction, but to a smaller extent than seen with dual treatment, consistent with the findings above that anti-ALK potentiates crizotinib effects.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for inhibiting neuroblastoma in a subject comprising:
   administering to said subject at least one composition comprising crizotinib and at least one pharmaceutically acceptable carrier, thereby increasing neuroblastoma cell surface anaplastic lymphoma kinase (ALK) expression, and
   administering to said subject at least one composition comprising at least one antibody immunologically specific for ALK and at least one pharmaceutically acceptable carrier, wherein said ALK antibody is immunologically specific for the extracellular domain of ALK, and wherein said ALK antibody induces antibody-dependent cellular cytotoxicity (ADCC) of the cell.

2. The method of claim 1, wherein said neuroblastoma is resistant to at least one ALK inhibitor.

3. The method of claim 1, wherein said neuroblastoma is resistant to crizotinib.

4. The method of claim 1, wherein said wherein said ALK antibody is a monoclonal antibody.

5. The method of claim 1, wherein said neuroblastoma has a mutation in ALK, and wherein at least one of the amino acids of the group consisting of P36, P157, V198, G640, L684, G718, G718, D993, L1204, 11170, A1200, L1204, F1245, G1128, R1192, R1275, D1091, M1166, 11171, F1174, F1245, and 11250 is mutated.

6. The method of claim 5, wherein at least R1275 or F1174 is mutated.

7. The method of claim 5, wherein the ALK comprises the R1275Q mutation.

8. The method of claim 5, wherein the ALK comprises the F1174L mutation.

9. The method of claim 1, wherein said neuroblastoma has an amplification in the ALK copy number.

* * * * *

SEQUENCE LISTING

```
<160> NUMBER OF SEQ ID NOS: 6

<210> SEQ ID NO 1
<211> LENGTH: 21
<212> TYPE: RNA
<213> ORGANISM: Artificial Sequence
<220> FEATURE:
<223> OTHER INFORMATION: siRNA sense strand

<400> SEQUENCE: 1
gggccuguau accggauaau u                                                 21

<210> SEQ ID NO 2
<211> LENGTH: 21
<212> TYPE: RNA
<213> ORGANISM: Artificial Sequence
<220> FEATURE:
<223> OTHER INFORMATION: siRNA sense strand

<400> SEQUENCE: 2
gugccaugcu gccaguuaau u                                                 21
```

<210> SEQ ID NO 3
<211> LENGTH: 21
<212> TYPE: RNA
<213> ORGANISM: Artificial Sequence
<220> FEATURE:
<223> OTHER INFORMATION: siRNA sense strand

<400> SEQUENCE: 3
ccgcuuugcc gauagaauau u        21

<210> SEQ ID NO 4
<211> LENGTH: 21
<212> TYPE: RNA
<213> ORGANISM: Artificial Sequence
<220> FEATURE:
<223> OTHER INFORMATION: siRNA sense strand

<400> SEQUENCE: 4
ggagccaccu acguauuuau u        21

<210> SEQ ID NO 5
<211> LENGTH: 1620
<212> TYPE: PRT
<213> ORGANISM: Homo sapiens

<400> SEQUENCE: 5

Met Gly Ala Ile Gly Leu Leu Trp Leu Leu Pro Leu Leu Leu Ser Thr
1               5                   10                  15

Ala Ala Val Gly Ser Gly Met Gly Thr Gly Gln Arg Ala Gly Ser Pro
            20                  25                  30

Ala Ala Gly Pro Pro Leu Gln Pro Arg Glu Pro Leu Ser Tyr Ser Arg
        35                  40                  45

Leu Gln Arg Lys Ser Leu Ala Val Asp Phe Val Val Pro Ser Leu Phe
    50                  55                  60

Arg Val Tyr Ala Arg Asp Leu Leu Leu Pro Pro Ser Ser Ser Glu Leu
65                  70                  75                  80

Lys Ala Gly Arg Pro Glu Ala Arg Gly Ser Leu Ala Leu Asp Cys Ala
                85                  90                  95

Pro Leu Leu Arg Leu Leu Gly Pro Ala Pro Gly Val Ser Trp Thr Ala
            100                 105                 110

Gly Ser Pro Ala Pro Ala Glu Ala Arg Thr Leu Ser Arg Val Leu Lys
        115                 120                 125

Gly Gly Ser Val Arg Lys Leu Arg Arg Ala Lys Gln Leu Val Leu Glu
    130                 135                 140

Leu Gly Glu Glu Ala Ile Leu Glu Gly Cys Val Gly Pro Pro Gly Glu
145                 150                 155                 160

Ala Ala Val Gly Leu Leu Gln Phe Asn Leu Ser Glu Leu Phe Ser Trp
                165                 170                 175

Trp Ile Arg Gln Gly Glu Gly Arg Leu Arg Ile Arg Leu Met Pro Glu
            180                 185                 190

Lys Lys Ala Ser Glu Val Gly Arg Glu Gly Arg Leu Ser Ala Ala Ile
        195                 200                 205

Arg Ala Ser Gln Pro Arg Leu Leu Phe Gln Ile Phe Gly Thr Gly His
    210                 215                 220

Ser Ser Leu Glu Ser Pro Thr Asn Met Pro Ser Pro Ser Pro Asp Tyr
225                 230                 235                 240

Phe Thr Trp Asn Leu Thr Trp Ile Met Lys Asp Ser Phe Pro Phe Leu

```
            245                 250                 255
Ser His Arg Ser Arg Tyr Gly Leu Glu Cys Ser Phe Asp Phe Pro Cys
            260                 265                 270

Glu Leu Glu Tyr Ser Pro Pro Leu His Asp Leu Arg Asn Gln Ser Trp
            275                 280                 285

Ser Trp Arg Arg Ile Pro Ser Glu Glu Ala Ser Gln Met Asp Leu Leu
            290                 295                 300

Asp Gly Pro Gly Ala Glu Arg Ser Lys Glu Met Pro Arg Gly Ser Phe
305                 310                 315                 320

Leu Leu Leu Asn Thr Ser Ala Asp Ser Lys His Thr Ile Leu Ser Pro
                325                 330                 335

Trp Met Arg Ser Ser Glu His Cys Thr Leu Ala Val Ser Val His
                340                 345                 350

Arg His Leu Gln Pro Ser Gly Arg Tyr Ile Ala Gln Leu Leu Pro His
                355                 360                 365

Asn Glu Ala Ala Arg Glu Ile Leu Leu Met Pro Thr Pro Gly Lys His
            370                 375                 380

Gly Trp Thr Val Leu Gln Gly Arg Ile Gly Arg Pro Asp Asn Pro Phe
385                 390                 395                 400

Arg Val Ala Leu Glu Tyr Ile Ser Ser Gly Asn Arg Ser Leu Ser Ala
                405                 410                 415

Val Asp Phe Phe Ala Leu Lys Asn Cys Ser Glu Gly Thr Ser Pro Gly
                420                 425                 430

Ser Lys Met Ala Leu Gln Ser Ser Phe Thr Cys Trp Asn Gly Thr Val
                435                 440                 445

Leu Gln Leu Gly Gln Ala Cys Asp Phe His Gln Asp Cys Ala Gln Gly
                450                 455                 460

Glu Asp Glu Ser Gln Met Cys Arg Lys Leu Pro Val Gly Phe Tyr Cys
465                 470                 475                 480

Asn Phe Glu Asp Gly Phe Cys Gly Trp Thr Gln Gly Thr Leu Ser Pro
                485                 490                 495

His Thr Pro Gln Trp Gln Val Arg Thr Leu Lys Asp Ala Arg Phe Gln
                500                 505                 510

Asp His Gln Asp His Ala Leu Leu Leu Ser Thr Thr Asp Val Pro Ala
            515                 520                 525

Ser Glu Ser Ala Thr Val Thr Ser Ala Thr Phe Pro Ala Pro Ile Lys
            530                 535                 540

Ser Ser Pro Cys Glu Leu Arg Met Ser Trp Leu Ile Arg Gly Val Leu
545                 550                 555                 560

Arg Gly Asn Val Ser Leu Val Leu Val Glu Asn Lys Thr Gly Lys Glu
                565                 570                 575

Gln Gly Arg Met Val Trp His Val Ala Ala Tyr Glu Gly Leu Ser Leu
                580                 585                 590

Trp Gln Trp Met Val Leu Pro Leu Leu Asp Val Ser Asp Arg Phe Trp
                595                 600                 605

Leu Gln Met Val Ala Trp Trp Gly Gln Gly Ser Arg Ala Ile Val Ala
            610                 615                 620

Phe Asp Asn Ile Ser Ile Ser Leu Asp Cys Tyr Leu Thr Ile Ser Gly
625                 630                 635                 640

Glu Asp Lys Ile Leu Gln Asn Thr Ala Pro Lys Ser Arg Asn Leu Phe
                645                 650                 655

Glu Arg Asn Pro Asn Lys Glu Leu Lys Pro Gly Glu Asn Ser Pro Arg
                660                 665                 670
```

```
Gln Thr Pro Ile Phe Asp Pro Thr Val His Trp Leu Phe Thr Thr Cys
            675                 680                 685

Gly Ala Ser Gly Pro His Gly Pro Thr Gln Ala Gln Cys Asn Asn Ala
690                 695                 700

Tyr Gln Asn Ser Asn Leu Ser Val Glu Val Gly Ser Glu Gly Pro Leu
705                 710                 715                 720

Lys Gly Ile Gln Ile Trp Lys Val Pro Ala Thr Asp Thr Tyr Ser Ile
                725                 730                 735

Ser Gly Tyr Gly Ala Ala Gly Gly Lys Gly Gly Lys Asn Thr Met Met
                740                 745                 750

Arg Ser His Gly Val Ser Val Leu Gly Ile Phe Asn Leu Glu Lys Asp
                755                 760                 765

Asp Met Leu Tyr Ile Leu Val Gly Gln Gln Gly Glu Asp Ala Cys Pro
770                 775                 780

Ser Thr Asn Gln Leu Ile Gln Lys Val Cys Ile Gly Glu Asn Asn Val
785                 790                 795                 800

Ile Glu Glu Glu Ile Arg Val Asn Arg Ser Val His Glu Trp Ala Gly
                805                 810                 815

Gly Gly Gly Gly Gly Gly Ala Thr Tyr Val Phe Lys Met Lys Asp
                820                 825                 830

Gly Val Pro Val Pro Leu Ile Ile Ala Ala Gly Gly Gly Gly Arg Ala
                835                 840                 845

Tyr Gly Ala Lys Thr Asp Thr Phe His Pro Glu Arg Leu Glu Asn Asn
850                 855                 860

Ser Ser Val Leu Gly Leu Asn Gly Asn Ser Ala Ala Gly Gly Gly
865                 870                 875                 880

Gly Gly Trp Asn Asp Asn Thr Ser Leu Leu Trp Ala Gly Lys Ser Leu
                885                 890                 895

Gln Glu Gly Ala Thr Gly Gly His Ser Cys Pro Gln Ala Met Lys Lys
                900                 905                 910

Trp Gly Trp Glu Thr Arg Gly Phe Gly Gly Gly Gly Gly Cys
                915                 920                 925

Ser Ser Gly Gly Gly Gly Gly Tyr Ile Gly Gly Asn Ala Ala Ser
            930                 935                 940

Asn Asn Asp Pro Glu Met Asp Gly Glu Asp Gly Val Ser Phe Ile Ser
945                 950                 955                 960

Pro Leu Gly Ile Leu Tyr Thr Pro Ala Leu Lys Val Met Glu Gly His
                965                 970                 975

Gly Glu Val Asn Ile Lys His Tyr Leu Asn Cys Ser His Cys Glu Val
                980                 985                 990

Asp Glu Cys His Met Asp Pro Glu Ser His Lys Val Ile Cys Phe Cys
                995                 1000                1005

Asp His Gly Thr Val Leu Ala Glu Asp Gly Val Ser Cys Ile Val Ser
            1010                1015                1020

Pro Thr Pro Glu Pro His Leu Pro Leu Ser Leu Ile Leu Ser Val Val
1025                1030                1035                1040

Thr Ser Ala Leu Val Ala Ala Leu Val Leu Ala Phe Ser Gly Ile Met
                1045                1050                1055

Ile Val Tyr Arg Arg Lys His Gln Glu Leu Gln Ala Met Gln Met Glu
                1060                1065                1070

Leu Gln Ser Pro Glu Tyr Lys Leu Ser Lys Leu Arg Thr Ser Thr Ile
                1075                1080                1085
```

```
Met Thr Asp Tyr Asn Pro Asn Tyr Cys Phe Ala Gly Lys Thr Ser Ser
    1090                1095                1100

Ile Ser Asp Leu Lys Glu Val Pro Arg Lys Asn Ile Thr Leu Ile Arg
1105                1110                1115                1120

Gly Leu Gly His Gly Ala Phe Gly Glu Val Tyr Glu Gly Gln Val Ser
            1125                1130                1135

Gly Met Pro Asn Asp Pro Ser Pro Leu Gln Val Ala Val Lys Thr Leu
        1140                1145                1150

Pro Glu Val Cys Ser Glu Gln Asp Glu Leu Asp Phe Leu Met Glu Ala
            1155                1160                1165

Leu Ile Ile Ser Lys Phe Asn His Gln Asn Ile Val Arg Cys Ile Gly
1170                1175                1180

Val Ser Leu Gln Ser Leu Pro Arg Phe Ile Leu Leu Glu Leu Met Ala
1185                1190                1195                1200

Gly Gly Asp Leu Lys Ser Phe Leu Arg Glu Thr Arg Pro Arg Pro Ser
            1205                1210                1215

Gln Pro Ser Ser Leu Ala Met Leu Asp Leu Leu His Val Ala Arg Asp
        1220                1225                1230

Ile Ala Cys Gly Cys Gln Tyr Leu Glu Glu Asn His Phe Ile His Arg
            1235                1240                1245

Asp Ile Ala Ala Arg Asn Cys Leu Leu Thr Cys Pro Gly Pro Gly Arg
        1250                1255                1260

Val Ala Lys Ile Gly Asp Phe Gly Met Ala Arg Asp Ile Tyr Arg Ala
1265                1270                1275                1280

Ser Tyr Tyr Arg Lys Gly Gly Cys Ala Met Leu Pro Val Lys Trp Met
            1285                1290                1295

Pro Pro Glu Ala Phe Met Glu Gly Ile Phe Thr Ser Lys Thr Asp Thr
        1300                1305                1310

Trp Ser Phe Gly Val Leu Leu Trp Glu Ile Phe Ser Leu Gly Tyr Met
            1315                1320                1325

Pro Tyr Pro Ser Lys Ser Asn Gln Glu Val Leu Glu Phe Val Thr Ser
        1330                1335                1340

Gly Gly Arg Met Asp Pro Pro Lys Asn Cys Pro Gly Pro Val Tyr Arg
1345                1350                1355                1360

Ile Met Thr Gln Cys Trp Gln His Gln Pro Glu Asp Arg Pro Asn Phe
            1365                1370                1375

Ala Ile Ile Leu Glu Arg Ile Glu Tyr Cys Thr Gln Asp Pro Asp Val
        1380                1385                1390

Ile Asn Thr Ala Leu Pro Ile Glu Tyr Gly Pro Leu Val Glu Glu Glu
        1395                1400                1405

Glu Lys Val Pro Val Arg Pro Lys Asp Pro Glu Gly Val Pro Pro Leu
1410                1415                1420

Leu Val Ser Gln Gln Ala Lys Arg Glu Glu Glu Arg Ser Pro Ala Ala
1425                1430                1435                1440

Pro Pro Pro Leu Pro Thr Thr Ser Ser Gly Lys Ala Ala Lys Lys Pro
            1445                1450                1455

Thr Ala Ala Glu Ile Ser Val Arg Val Pro Arg Gly Pro Ala Val Glu
            1460                1465                1470

Gly Gly His Val Asn Met Ala Phe Ser Gln Ser Asn Pro Pro Ser Glu
            1475                1480                1485

Leu His Lys Val His Gly Ser Arg Asn Lys Pro Thr Ser Leu Trp Asn
        1490                1495                1500

Pro Thr Tyr Gly Ser Trp Phe Thr Glu Lys Pro Thr Lys Lys Asn Asn
```

```
1505                1510                1515                1520
Pro Ile Ala Lys Lys Glu Pro His Asp Arg Gly Asn Leu Gly Leu Glu
            1525                1530                1535
Gly Ser Cys Thr Val Pro Pro Asn Val Ala Thr Gly Arg Leu Pro Gly
            1540                1545                1550
Ala Ser Leu Leu Leu Glu Pro Ser Ser Leu Thr Ala Asn Met Lys Glu
            1555                1560                1565
Val Pro Leu Phe Arg Leu Arg His Phe Pro Cys Gly Asn Val Asn Tyr
            1570                1575                1580
Gly Tyr Gln Gln Gln Gly Leu Pro Leu Glu Ala Ala Thr Ala Pro Gly
            1585                1590                1595                1600
Ala Gly His Tyr Glu Asp Thr Ile Leu Lys Ser Lys Asn Ser Met Asn
            1605                1610                1615
Gln Pro Gly Pro
            1620

<210> SEQ ID NO 6
<211> LENGTH: 4863
<212> TYPE: DNA
<213> ORGANISM: Homo sapiens

<400> SEQUENCE: 6
```

| | | | | | |
|---|---|---|---|---|---|
| atgggagcca | tcgggctcct | gtggctcctg | ccgctgctgc | tttccacggc | agctgtgggc | 60 |
| tccgggatgg | ggaccggcca | gcgcgcgggc | tccccagctg | cggggccgcc | gctgcagccc | 120 |
| cgggagccac | tcagctactc | cgcctgcag | aggaagagtc | tggcagttga | cttcgtggtg | 180 |
| ccctcgctct | tccgtgtcta | cgcccgggac | ctactgctgc | caccatcctc | ctcggagctg | 240 |
| aaggctggca | ggcccgaggc | ccgcggctcg | ctagctctgg | actgcgcccc | gctgctcagg | 300 |
| ttgctgggc | cggcgccggg | ggtctcctgg | accgccggtt | caccagcccc | ggcagaggcc | 360 |
| cggacgctgt | ccagggtgct | gaagggcggc | tccgtgcgca | agctccggcg | tgccaagcag | 420 |
| ttggtgctgg | agctgggcga | ggaggcgatc | ttggagggtt | gcgtcgggcc | ccccggggag | 480 |
| gcggctgtgg | ggctgctcca | gttcaatctc | agcgagctgt | tcagttggtg | gattcgccaa | 540 |
| ggcgaagggc | gactgaggat | ccgcctgatg | cccgagaaga | aggcgtcgga | agtgggcaga | 600 |
| gagggaaggc | tgtccgcggc | aattcgcgcc | tcccagcccc | gccttctctt | ccagatcttc | 660 |
| gggactggtc | atagctcctt | ggaatcacca | acaaacatgc | cttctccttc | tcctgattat | 720 |
| tttacatgga | atctcacctg | gataatgaaa | gactccttcc | ctttcctgtc | tcatcgcagc | 780 |
| cgatatggtc | tggagtgcag | ctttgacttc | ccctgtgagc | tggagtattc | ccctccactg | 840 |
| catgacctca | ggaaccagag | ctggtcctgg | cgccgcatcc | cctccgagga | ggcctcccag | 900 |
| atggacttgc | tggatgggcc | tggggcagag | cgttctaagg | agatgccag | aggctccttt | 960 |
| ctccttctca | acacctcagc | tgactccaag | cacaccatcc | tgagtccgtg | atgaggagc | 1020 |
| agcagtgagc | actgcacact | ggccgtctcg | gtgcacaggc | acctgcagcc | ctctggaagg | 1080 |
| tacattgccc | agctgctgcc | ccacaacgag | gctgcaagag | agatcctcct | gatgcccact | 1140 |
| ccagggaagc | atggttggac | agtgctccag | ggaagaatcg | ggcgtccaga | caacccattt | 1200 |
| cgagtggccc | tggaatacat | ctccagtgga | aaccgcagct | gtctgcagt | ggacttcttt | 1260 |
| gccctgaaga | actgcagtga | aggaacatcc | ccaggctcca | agatggccct | gcagagctcc | 1320 |
| ttcacttgtt | ggaatgggac | agtcctccag | cttgggcagg | cctgtgactt | ccaccaggac | 1380 |
| tgtgcccagg | gagaagatga | gagccagatg | tgccggaaac | tgcctgtggg | tttttactgc | 1440 |

```
aactttgaag atggcttctg tggctggacc caaggcacac tgtcacccca cactcctcaa   1500
tggcaggtca ggaccctaaa ggatgcccgg ttccaggacc accaagacca tgctctattg   1560
ctcagtacca ctgatgtccc cgcttctgaa agtgctacag tgaccagtgc tacgtttcct   1620
gcaccgatca agagctctcc atgtgagctc cgaatgtcct ggctcattcg tggagtcttg   1680
aggggaaacg tgtccttggt gctagtggag aacaaaaccg ggaaggagca aggcaggatg   1740
gtctggcatg tcgccgccta tgaaggcttg agcctgtggc agtggatggt gttgcctctc   1800
ctcgatgtgt ctgacaggtt ctggctgcag atggtcgcat ggtggggaca aggatccaga   1860
gccatcgtgg cttttgacaa tatctccatc agcctggact gctacctcac cattagcgga   1920
gaggacaaga tcctgcagaa tacagcaccc aaatcaagaa acctgtttga gagaaaccca   1980
aacaaggagc tgaaacccgg ggaaaattca ccaagacaga cccccatctt tgaccctaca   2040
gttcattggc tgttcaccac atgtggggcc agcgggcccc atggcccacc caggcacag   2100 tgcaacaacg cctaccagaa ctccaacctg agcgtggagg tggggagcga ggcccctg    2160 aaaggcatcc agatctggaa ggtgccagcc accgacacct acagcatctc gggctacgga   2220
gctgctggcg ggaaaggcgg gaagaacacc atgatgcggt cccacggcgt gtctgtgctg   2280
ggcatcttca acctggagaa ggatgacatg ctgtacatcc tggttgggca gcagggagag   2340
gacgcctgcc ccagtacaaa ccagttaatc cagaaagtct gcattggaga gaacaatgtg   2400
atagaagaag aaatccgtgt gaacagaagc gtgcatgagt gggcaggagg cggaggagga   2460
gggggtggag ccacctacgt atttaagatg aaggatggag tgccggtgcc cctgatcatt   2520
gcagccgagg gtggtggcag ggcctacggg gccaagacag acacgttcca cccagagaga   2580
ctggagaata actcctcggt tctagggcta aacggcaatt ccggagccgc aggtggtgga   2640
ggtggctgga atgataacac ttccttgctc tgggccggaa aatctttgca ggagggtgcc   2700
accggaggac attcctgccc ccaggccatg aagaagtggg ggtgggagac aagaggggt   2760 ttcggagggg gtggaggggg gtgctcctca ggtggaggag gcgaggata tataggcggc   2820 aatgcagcct caaacaatga ccccgaaatg gatggggaag atggggtttc cttcatcagt   2880
ccactgggca tcctgtacac cccagcttta aaagtgatgg aaggccacgg ggaagtgaat   2940
attaagcatt atctaaactg cagtcactgt gaggtagacg aatgtcacat ggaccctgaa   3000
agccacaagg tcatctgctt ctgtgaccac gggacggtgc tggctgagga tggcgtctcc   3060
tgcattgtgt cacccacccc ggagccacac ctgccactct cgctgatcct ctctgtggtg   3120
acctctgccc tcgtggccgc cctggtcctg gctttctccg gcatcatgat tgtgtaccgc   3180
cggaagcacc aggagctgca agccatgcag atggagctgc agagccctga gtacaagctg   3240
agcaagctcc gcacctcgac catcatgacc gactacaacc caactactg ctttgctggc   3300 aagacctcct ccatcagtga cctgaaggag gtgccgcgga aaaacatcac cctcattcgg   3360
ggtctgggcc atggcgcctt tggggaggtg tatgaaggcc aggtgtccgg aatgcccaac   3420
gacccaagcc ccctgcaagt ggctgtgaag acgctgcctg aagtgtgctc tgaacaggac   3480
gaactggatt tcctcatgga agccctgatc atcagcaaat tcaaccacca gaacattgtt   3540
cgctgcattg gggtgagcct gcaatccctg ccccggttca tcctgctgga gctcatggcg   3600
gggggagacc tcaagtcctt cctccgagag acccgccctc gcccgagcca gccctcctcc   3660
ctggccatgc tggaccttct gcacgtggct cgggacattg cctgtggctg tcagtatttg   3720
gaggaaaacc acttcatcca ccgagacatt gctgccagaa actgcctctt gacctgtcca   3780
ggccctggaa gagtggccaa gattggagac ttcgggatgg cccgagacat ctacagggcg   3840
```

```
agctactata gaaagggagg ctgtgccatg ctgccagtta agtggatgcc cccagaggcc    3900
ttcatggaag gaatattcac ttctaaaaca gacacatggt cctttggagt gctgctatgg    3960
gaaatctttt ctcttggata tatgccatac cccagcaaaa gcaaccagga agttctggag    4020
tttgtcacca gtggaggccg gatggaccca cccaagaact gccctgggcc tgtataccgg    4080
ataatgactc agtgctggca acatcagcct gaagacaggc ccaactttgc catcattttg    4140
gagaggattg aatactgcac ccaggacccg gatgtaatca acaccgcttt gccgatagaa    4200
tatggtccac ttgtggaaga ggaagagaaa gtgcctgtga ggcccaagga ccctgagggg    4260
gttcctcctc tcctggtctc tcaacaggca aaacgggagg aggagcgcag cccagctgcc    4320
ccaccacctc tgcctaccac ctcctctggc aaggctgcaa agaaacccac agctgcagag    4380
atctctgttc gagtccctag agggccggcc gtggaagggg gacacgtgaa tatggcattc    4440
tctcagtcca accctccttc ggagttgcac aaggtccacg gatccagaaa caagcccacc    4500
agcttgtgga acccaacgta cggctcctgg tttacagaga aacccaccaa aaagaataat    4560
cctatagcaa agaaggagcc acacgacagg ggtaacctgg ggctggaggg aagctgtact    4620
gtcccaccta acgttgcaac tgggagactt ccgggggcct cactgctcct agagccctct    4680
tcgctgactg ccaatatgaa ggaggtacct ctgttcaggc tacgtcactt cccttgtggg    4740
aatgtcaatt acggctacca gcaacagggc ttgcccttag aagccgctac tgcccctgga    4800
gctggtcatt acgaggatac cattctgaaa agcaagaata gcatgaacca gcctgggccc    4860
tga                                                                 4863
```